United States Patent
Manoharan et al.

(10) Patent No.: US 6,642,373 B2
(45) Date of Patent: Nov. 4, 2003

(54) ACTIVATORS FOR OLIGONUCLEOTIDE SYNTHESIS

(75) Inventors: Muthia Manoharan, Carlsbad, CA (US); Vasulinga T. Ravikumar, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/318,628

(22) Filed: Dec. 12, 2002

(65) Prior Publication Data

US 2003/0191304 A1 Oct. 9, 2003

Related U.S. Application Data

(62) Division of application No. 09/708,224, filed on Nov. 8, 2000, which is a division of application No. 09/177,953, filed on Oct. 23, 1998, now Pat. No. 6,274,725.

(60) Provisional application No. 60/087,757, filed on Jun. 2, 1998.

(51) Int. Cl.[7] .......................... C07H 21/00; C07H 21/04
(52) U.S. Cl. .................. 536/25.34; 536/22.1; 536/23.1; 536/25.3; 536/25.33; 536/25.4; 536/25.41; 536/26.26; 536/26.7; 536/26.8; 536/27.6; 536/27.81; 536/28.5; 536/28.53; 536/28.54
(58) Field of Search .............................. 536/22.1, 23.2, 536/25.3, 25.33, 25.34, 25.4, 25.41, 26.26, 26.7, 26.8, 27.6, 27.81, 28.5, 28.53, 28.54

(56) References Cited

U.S. PATENT DOCUMENTS

| | | | |
|---|---|---|---|
| 3,687,808 A | 8/1972 | Merigan et al. ............. 195/28 |
| 4,415,732 A | 11/1983 | Caruthers et al. ............. 536/27 |
| 4,458,066 A | 7/1984 | Caruthers et al. ............. 536/27 |
| 4,500,707 A | 2/1985 | Caruthers et al. ............. 536/27 |
| 4,668,777 A | 5/1987 | Caruthers et al. ............. 536/27 |
| 4,725,677 A | 2/1988 | Koster et al. ................. 536/27 |
| 4,760,137 A | 7/1988 | Robins et al. ................ 536/24 |
| 4,973,679 A | 11/1990 | Caruthers et al. ............. 536/27 |
| 4,997,926 A | 3/1991 | Haertle et al. ............... 536/24 |
| 5,132,418 A | 7/1992 | Caruthers et al. ............. 536/27 |
| RE34,069 E | 9/1992 | Koster et al. ................. 536/27 |
| 5,208,327 A | 5/1993 | Chen .......................... 536/46 |
| 6,166,197 A | 12/2000 | Cook et al. ................. 536/24.5 |

OTHER PUBLICATIONS

Agrawal, S., "Antisense Oligonucleotides: Towards Clinical Trials," TIBTECH, Oct. 1996, 14, 376–387.

Agrawal, et al., "Methods of Molecular Biology", *Protocols for Oligonucleotide Conjugates*, Eds, Humana Press; New Jersey, 1994; 26, 1–72.

(List continued on next page.)

*Primary Examiner*—James O. Wilson
*Assistant Examiner*—Josephine Young
(74) *Attorney, Agent, or Firm*—Woodcock Washburn LLP

(57) ABSTRACT

The present invention relates to improved methods for the preparation of nucleoside phosphoramidites and oligonucleotides. In one aspect, the methods of the invention are used to prepare phosphitylating reagents using pyridinium salts as activators. In a further aspect, the methods of the invention are used to prepare internucleoside linkages using activators which include at least one pyridinium salt and at least one substituted imidazole. In a further aspect, methods are provided preparation of internucleoside linkages between nucleosides having 2'-substituents using imidazolium or benzimidazolium salts as an activator. In a further aspect, methods are provided preparation of internucleoside linkages between nucleosides having bioreversible protecting group that confers enhanced chemical and biophysical properties, without exocyclic amine protection, using imidazolium or benzimidazolium salts as an activator.

71 Claims, 5 Drawing Sheets

OTHER PUBLICATIONS

Alul, R.H. et al., "Oxalyl–CPG: a labile support for synthesis of sensitive oligonucleotide derivatives", *Nucl. Acid Res.*, 1991, 19, 1527.

Bannwarth, W., "Synthesis of Oligodeoxynucleotides by the Phosphite–Triester Method Using Dimer Units and Different Phosphorous–Protecting Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311.

Beaucage, S.L. et al., "Deoxynucleoside Phosphoramidites—A New Class of Key Intermediates for Deoxypolynucleotide Synthesis", *Tetrahedron Letts.*, 1981, 22, 1859–1862.

Beaucage, S. L., "Oligodeoxyribonucleotides Synthesis: Phosphoramidite Approach," *Methods in Molecular Biology*, 1993, 20, Chap. 3, Agrawal, S., ed., Humana Press Inc., Totowa, NJ, 33–61.

Beier, M. et al., "Phthaloyl Strategy—A New Approach Towards Oligodeoxyribonucleotide Synthesis," *Nucleosides & Nucleotides*, 1997, 16(7–9), 1621–1624.

Bhan, P. et al., "Inhibition of 5–a–Reductase (Type–II) Expression by Antisense 3'–Deoxy–(2',5') Oligonucleotide Chimeras," *Nucleosides & Nucleotides*, 1997, 16, 1195–1199.

Bonora et al., "Large Scale, liquid phase synthesis of oligonucleotides by the phosphoramidite approach," *Nucl. Acids Res.*, 1993, 21, 1213–1217.

Brill, W.K.D. et al., "Synthesis of Deoxydinucleoside Phosphorodithioates", *J. Am. Chem. Soc.*, 1991, 113, 3972–3980.

Brown, T. et al., "Modern machine–aided methods of oligodeoxyribonucleotide synthesis", *Oligonucleotides and Analogs a Practical Approach*, 1991, Chapter 1, Ekstein, F., ed., IRL Press, Oxford, 1–24.

Cook, P.D., "Medicinal Chemistry of Antisense Oligonucleotides—future opportunities", *Anti–Cancer Drug Des.*, 1991, 6, 585–607.

Crooke et al., "Antisense Therapeutics," *Biotechnology and Genetic Engineering Reviews*, Apr. 1998, 15, 121–157.

Dabkowski, W., et al., "Trimethylchlorosilane: A Novel Activating Reagent in Nucleotide Synthesis Via the Phosphoramidite Route," *Chem. Comm.*, 1997, 877–878.

Dahl, B.H. et al., "Mechanistic studies on the phosphoramidite coupling reaction in oligonucleotide synthesis. I. Evidence for nucleophilic catalysis by tetrazole and rate variations with the phosphorus substituents", *Nucl. Acids Res.*, 1987, 15, 1729–1743.

Delgado, C. et al., "The Uses and Properties of PEG–Linked Proteins", *Crit. Rev. in Therapeutic Drug Carrier Sys.*, 1992, 9, 249–304.

Dell'Aquila, C. et al., "Photolabile Linker for the SolidPhase Synthesis of Base–Sensitive Oligonucleotides," *Tetrahedron Letts.*, 1997, 38, 5289–5292.

Efimov, V.A. et al., "New efficient sulfurizing reagents for the preparation of oligodeoxyribonucleotide phosphorothioate analogues", *Nucl. Acids Res.*, 1995, 23, 4029–4033.

Englisch, U. et al., "Chemically Modified Oligonucleotides as Probes and Inhibitors", *Angew. Chem. Int. Ed. Eng.*, 1991, 30, 613–629.

Filippov et al., "A Study Towards Total Synthesis of Antibiotic Agrocin 84," *Nucleosides & Nucleotides*, 1997, 16(7–9), 1403–1406.

Fourrey, J. et al., "Improved Procedure for the Preparation of Deoxynucleoside Phosphoramidites Arylphosphoramidites as New Convenient Intermediates for Oligodeoxynucleotide Synthesis," *Tetrahedron Letts.*, 1984, 25(40), 4511–4514.

Green and Wuts, *Protective Groups in Organic Synthesis*, $2^{nd}$ edition, John Wiley & Sons, New York, 1991.

Greenberg, M. M. et al., "Photochemical Cleavage of Oligonucleotides From Solid Phase Supports," *Tetrahedron Letts.*, 1993, 34, 251–254.

Greene, T. W. et al., "Protection for the Amino Group," *Protective Groups in Organic Synthesis*, 1991, Chapter 7, John Wiley & Sons, 308–405.

Gryaznov, S. M. et al., "Selective O–phosphitilation with the Nucleoside Phosphoramidite Reagents," *Nucl. Acids Res.*, 1992, 20(8), 1879–1881.

Hayakawa, Y. et al., "A Facile Nucleotide Synthesis via the Phosphoramidite Method Using Imidazolium Triflate as the Promoter," *Nucl. Acids and Related Macromolecules Synthesis, Structure, Function and Applications*, Sep. 4–9 1997, Ulm, Germany, 1 page.

Hayakawa, Y. et al., "Benzimidazolium Triflate as an Efficient Promoter for Nucleotide Synthesis via the Phosphoramidite Method," *J. Org. Chem.*, 1996, 61, 7996–7997.

Holmes, C. P., et al., "Model Studies for New o–Nitrobenzyl Photolabile Linkers: Substituent Effects on the Rates of Photochemical Cleavage," *J. Org. Chem.*, 1997, 62, 2370–2380.

Iyer, R. P. et al., "3H–1,2–Benzodithiole–3–one 1,1–Dioxide as an Improved Sulfurizing Reagent in the Solid–Phase Synthesis of Oligodeoxyribonucleoside Phosphorothioates," *J. Org. Chem. Soc.*, 1990, 112, 1253–1254.

Iyer, R. P. et al., "The Automated Synthesis of Sulfur–Containing Oligodeoxyribonucleotides Using 3H–1,2–Benzodithiol–3–one 1,1–Dioxide as a Sulfur–Transfer Reagent," *J. Org. Chem.*, 1990, 55, 4693–4699.

Kamer, P. C. J. et al., "An Efficient Approach Toward the Synthesis of Phosphorothioate Diesters via the Schonberg Reaction," *Tetrahedron Letts.*, 1989, 30, 6757–6760.

Kataoka, M. et al., "Imidazolium Triflate as an Efficient Promoter for O–selective Phoshitylation of N–unprotected Nucleosides via the Phosphoramidite Approach," *Nucl. Acids*, 1997, 21–22.

Kroschwitz, J.I., "Polynucleotides," *Concise Encyclopedia of Polymer Science and Engineering*, 1990, John Wiley & Sons, New York, 858–859.

Krotz et al., "On the Formation of Longmers in Phosphorothioate Oligodeozyribnucleotide Synthesis," *Tetrahedron Letts.*, 1997, 38, 3875–3878.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912.

Limbach, A., et al., "Summary: the modified nucleosides of RNA," *Nucl. Acids Res.*, 1994, 22, 2183–2196.

Marr, J., "Ribozymes as therapeutic agents," *Drug Disc. Today*, Mar. 1996, 1(3), 94–102.

Miura, K. et al., "Blockwise Mechanical Synthesis of Oligonucleotides by the Phosphoramidite Method", *Chem Pharm. Bull.*, 1987, 35, 833–836.

Mullah, B. and Andrus, A., "Automated Synthesis of Double Dye–Labeled Oligonucleotides using Tetramethylrhodamine (TAMRA) Solid Supports," *Tetrahedron Letts.*, 1997, 38(33), 5751–5754.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Pon, R. T., "Enhanced Coupling Efficiency Using 4–Dimethylaminopyridine (DMAP) and Either Tetrazole, 5–(o–Nitrophenyl) Tetrazole, or 5–(p–Nitrophenyl) Tetrazole in the Solid Phase Synthesis of Oligoribonucleotides by the Phosphoramidite Procedure," *Tetrahedron Letts.*, 1987, 28, 3643–3546.

Pon, R. T. et al., "Hydroquinone–O, O–diacetic acid ('Q–linker') as a replacement for succinyl and oxalyl linker arms in solid phase oligonucleotide synthesis," *Nucl. Acid Res.*, 1997, 25(18), 3629–3635.

Rao, M.V. et al., "Dibenzoyl Tetrasulphide—A Rapid Sulphur Transfer Agent in the Synthesis of Phosphorothioate Analogues of Oligonucleotides", *Tetrahedron Letts.*, 1992, 33, 4839–4842.

Ravasio, N. et al., "Selective Hydrogenations Promoted by Copper Catalysts. 1. Chemoselectivity, Regioselectivity and Stereoselectivity in the Hydrogenation of 3–Substituted Steroids", *J. Org. Chem.*, 1991, 56, 4329–4333.

Roush, W., "Antisense Aims for a Renaissance" *Science*, 1997, 276, 1192–1193.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Schlienger et al., "The Pronucleotide Approach.II: Synthesis and Preliminary Stability Studies of Mononucleoside Glycosyl Phosphotriester Derivatives," *Nucleosides & Nucleotides*, 1997, 16, 1325–1329.

Secrist, J.A. et al., "Synthesis and Biological Activity of 4'–Thionucleosides", 10th International Roundtable: *Nucleosides, Nucleotides and their Biological Applications*, Sep. 16–20, 1992, Abstract 21, Park City, Utah, 40.

Stec, W.J. et al., "Bis (O,O–Diisopropoxy Phosphinothioyl) Disulfide—A Highly Efficient Sulfurizing Reagent for Cost-Effective Synthesis of Oligo(Nucleoside Phosphorothioate)s", *Tetrahedron Letts.*, 1993, 34, 5317–5320.

Tosquellas, G. et al., "The pro–oligonucleotide approach: solid phase synthesis and preliminary evaluation of model pro–dodecathymidylates," *Nucl. Acid Res.*, 1998, 26(9), 2069–2074.

Vargeese, C. et al. "Efficient Activation of Nucleoside Phosphoramidites with 4,5–dicyanoimidazole during Oligonucleotide Synthesis," *Nucl. Acids Res.*, 1998, 26(4), 1046–1050.

Vinayak et al., "Automated Chemical Synthesis of PNA and PNA–DNA Chimera on a Nucleic Acid Synthesizer," *Nucleosides & Nucleotides, 1997*, 16(7–9), 1653–1656.

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.*, 1991, 32, 3005–3008.

Wagner S.et al., "Synthesis of Copper–64 and Technetium–99M Labeled Oligonucleotides with Macrocyclic Ligands," *Nucleosides & Nucleotides*, 1997, 16(7–9), 1789–1792.

Wagner, T.et al., "An Inverse Approach in Oligodeoxyribonucleotide Synthesis," *Nucleosides & Nucleotides*, 1997, 16(7–9), 1657–1660.

Wincott, F., et al., "Synthesis, deprotection, analysis and purification of RNA and ribozymes," *Nucl. Acids Res.*, 1995, 23 (14), 2677–2684.

Wolfgang, K., et al., "Synthesis of Deoxydinucleoside Phosphorodithioates," *J. Am. Chem. Soc.*, 1991, 113, 3972–3980.

Wolter, A. et al., "Polymer Support Oligonucleotide Synthesis XX: Synthesis of a Henhectacosa Deoxynucleotide by use of a Dimeric Phosphoramidite," *Nucleosides & Nucleotides*, 1986, 5, 65–77.

Wright, P. et al., "Large Scale Synthesis of Oligonucleotides via phosphoramidite Nucleosides and a High–loaded Polystyrene Support", *Tetrahedron Letts.*, 1993, 34, 3373–3376.

Xu, Q. et al., "Efficient introduction of phosphorothioates into RNA oligonucleotides by 3–ethoxy–1,2, 4–dithiazoline–5–one (EDITH)", *Nucl. Acids Res.*, 1996, 24, 3643–3644.

Xu, Q. et al., "Use of 1,2,4–dithiazoline (DtsNH) and 3–ethoxy–1,2,4–dithiazolidine–5–one (EDITH) for synthesis of phosphorothioate–containing oligodeoxyribonucleotides", *Nucl. Acids Res.*, 1996, 24, 1602–1607.

Gryaznov, et al., "Synthesis of oligonucleotides via monomers with unprotected bases," *J. Am. Chem. Soc.*, 1991, 113, 5876–5877.

Chen. J.T., et al., "Synthesis and separation of diastereomers of deoxynucleoside 5'–0–(1–thio) triphosphates," *Nucleic Acids Research*,1983, 11, 3737–3751.

SEQUENCE LISTING

<160> NUMBER OF SEQ ID NOS: 47

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
tcccgcctgt gacatgcatt                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
gcccaagctg gcatccgtca                                                    20

<210> SEQ ID NO 3
<211> LENGTH: 21
<212> TYPE: DNA
<213> ORGANISM: Artificial Sequence
<220> FEATURE:
<223> OTHER INFORMATION: Synthetic construct

<400> SEQUENCE: 3
gcgtttgctc ttcttcttgc g                                                  21

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
gttctcgctg gtgagtttca                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
tccgtcatcg ctcctcaggg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(20)
<223> OTHER INFORMATION: 2' methoxyethyl

<400> SEQUENCE: 6
tcccgcctgt gacatgcatt                                                    20

```
<210> SEQ ID NO 7
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(20)
<223> OTHER INFORMATION: 2' methyoxyethyl

<400> SEQUENCE: 7
tcccgcctgt gacatgcatt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: 5 methyl C
<220> FEATURE:
<221> NAME/KEY: misc_feature
<222> LOCATION: (8)..(8)
<223> OTHER INFORMATION: 5 methyl C
<220> FEATURE:
<221> NAME/KEY: misc_feature
<222> LOCATION: (12)..(12)
<223> OTHER INFORMATION: 5 methyl C
<220> FEATURE:
<221> NAME/KEY: misc_feature
<222> LOCATION: (13)..(20)
<223> OTHER INFORMATION: 2' methoxyethyl
<220> FEATURE:
<221> NAME/KEY: misc_feature
<222> LOCATION: (14)..(16)
<223> OTHER INFORMATION: 5 methyl U
<220> FEATURE:
<221> NAME/KEY: misc_feature
<222> LOCATION: (18)..(19)
<223> OTHER INFORMATION: 5 methyl U

<400> SEQUENCE: 8
gcccaagctg gcauccguca                                               20

<210> SEQ ID NO 9
<211> LENGTH: 19
<212> TYPE: DNA
<213> ORGANISM: Artificial Sequence
<220> FEATURE:
<223> OTHER INFORMATION: Synthetic construct

<400> SEQUENCE: 9
tggtggtggt ggtggtggt                                                19

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
tcccgcctgt gacatgcatt                                               20

<210> SEQ ID NO 11
```

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gcccaagctg gcatccgtca                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic construct

<400> SEQUENCE: 12
gcgtttgctc ttcttcttgc g                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
gttctcgctg gtgagtttca                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
tccgtcatcg ctcctcaggg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(20)
<223> OTHER INFORMATION: 2' O MOE

<400> SEQUENCE: 15
tcccgcctgt gacatgcatt                                              20

<210> SEQ ID NO 16
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(21)
<223> OTHER INFORMATION: 2' O MOE

<400> SEQUENCE: 16
gcccaagctg gcatcccgtc a                                            21
```

```
<210> SEQ ID NO 17
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: 5 methyl C
<220> FEATURE:
<221> NAME/KEY: misc_feature
<222> LOCATION: (8)..(8)
<223> OTHER INFORMATION: 5 methyl C
<220> FEATURE:
<221> NAME/KEY: misc_feature
<222> LOCATION: (12)..(12)
<223> OTHER INFORMATION: 5 methyl C
<220> FEATURE:
<221> NAME/KEY: misc_feature
<222> LOCATION: (13)..(20)
<223> OTHER INFORMATION: 2' O MOE
<220> FEATURE:
<221> NAME/KEY: misc_feature
<222> LOCATION: (14)..(16)
<223> OTHER INFORMATION: 5 methyl U
<220> FEATURE:
<221> NAME/KEY: misc_feature
<222> LOCATION: (18)..(19)
<223> OTHER INFORMATION: 5 methyl U

<400> SEQUENCE: 17
gcccaagctg gcauccguca                                           20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: 2' O MOE and phosphorothioate
      internucleotide linkages
<220> FEATURE:
<221> NAME/KEY: misc_feature
<222> LOCATION: (6)..(13)
<223> OTHER INFORMATION: phosphorothioate internucleotide linkages
<220> FEATURE:
<221> NAME/KEY: misc_feature
<222> LOCATION: (14)..(20)
<223> OTHER INFORMATION: 2' O MOE, phosphorothioate internucleotide
      linkages
<220> FEATURE:
<221> NAME/KEY: misc_feature
<222> LOCATION: (20)..(20)
<223> OTHER INFORMATION: 2' O MOE, phosphorothioate internucleotide
      linkages
<220> FEATURE:
<221> NAME/KEY: misc_feature
<222> LOCATION: (20)..(20)
<223> OTHER INFORMATION: 2' O MOE linkage

<400> SEQUENCE: 18
ttctcgcccg ctcctcctcc                                           20

<210> SEQ ID NO 19
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: (1)..(6)
<223> OTHER INFORMATION: 2' O MOE, phosphorothioate internucleotide
      linkages
<220> FEATURE:
<221> NAME/KEY: misc_feature
<222> LOCATION: (6)..(15)
<223> OTHER INFORMATION: phosphorothioate internucleotide linkages
<220> FEATURE:
<221> NAME/KEY: misc_feature
<222> LOCATION: (15)..(19)
<223> OTHER INFORMATION: 2' O MOE, phosphorothioated internucleotide
      linkages
<220> FEATURE:
<221> NAME/KEY: misc_feature
<222> LOCATION: (19)..(19)
<223> OTHER INFORMATION: 2' O MOE linkages

<400> SEQUENCE: 19
ttctcgctgg tgagtttca                                               19

<210> SEQ ID NO 20
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: 2' O MOE, phosphodiester internucleotide
      linkages
<220> FEATURE:
<221> NAME/KEY: misc_feature
<222> LOCATION: (5)..(6)
<223> OTHER INFORMATION: 2' O MOE, phosphorothioate internucleotide
      linkages
<220> FEATURE:
<221> NAME/KEY: misc_feature
<222> LOCATION: (6)..(14)
<223> OTHER INFORMATION: phosphorothioate internucleotide linkages
<220> FEATURE:
<221> NAME/KEY: misc_feature
<222> LOCATION: (14)..(20)
<223> OTHER INFORMATION: 2' O MOE, phosphodiester internucleotide
      linkages
<220> FEATURE:
<221> NAME/KEY: misc_feature
<222> LOCATION: (20)..(20)
<223> OTHER INFORMATION: 2' O MOE linkage

<400> SEQUENCE: 20
ttctcgcccg ctcctcctcc                                              20

<210> SEQ ID NO 21
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: 2' O MOE, phosphodiester internucleotide
      linkages
<220> FEATURE:
<221> NAME/KEY: misc_feature
<222> LOCATION: (5)..(6)
<223> OTHER INFORMATION: 2' O MOE, phosphorothioate internucleotide
      linkages
<220> FEATURE:
<221> NAME/KEY: misc_feature
<222> LOCATION: (6)..(15)
<223> OTHER INFORMATION: phosphorothioate internucleotide
      linkages
<220> FEATURE:
```

```
<221> NAME/KEY: misc_feature
<222> LOCATION: (15)..(19)
<223> OTHER INFORMATION: 2' MOE linkage

<400> SEQUENCE: 21
ttctcgctgg tgagtttca                                                       19

<210> SEQ ID NO 22
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: 2' O MOE, phosphorothioate linkage
<220> FEATURE:
<221> NAME/KEY: misc_feature
<222> LOCATION: (20)..(20)
<223> OTHER INFORMATION: 2' O MOE linkage

<400> SEQUENCE: 22
tctgagtagc agaggagctc                                                      20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: 2' O MOE linkage

<400> SEQUENCE: 23
tctgagtagc agaggagctc                                                      20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
tcccgcctgt gacatgcatt                                                      20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
gcccaagctg gcatccgtca                                                      20

<210> SEQ ID NO 26
<211> LENGTH: 21
<212> TYPE: DNA
<213> ORGANISM: Artificial Sequence
<220> FEATURE:
<223> OTHER INFORMATION: Synthetic construct

<400> SEQUENCE: 26
gcgtttgctc ttcttcttgc g                                                    21
```

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
gttctcgctg gtgagtttca                                        20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
tccgtcatcg ctcctcaggg                                        20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
tcccgcctgt gacatgcatt                                        20

<210> SEQ ID NO 30
<211> LENGTH: 21
<212> TYPE: DNA
<213> ORGANISM: Artificial Sequence
<220> FEATURE:
<223> OTHER INFORMATION: Synthetic construct

<400> SEQUENCE: 30
gcccaagctg gcatcccgtc a                                      21

<210> SEQ ID NO 31
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: 5 methyl C
<220> FEATURE:
<221> NAME/KEY: misc_feature
<222> LOCATION: (8)..(8)
<223> OTHER INFORMATION: 5 methyl C
<220> FEATURE:
<221> NAME/KEY: misc_feature
<222> LOCATION: (12)..(12)
<223> OTHER INFORMATION: 5 methyl C
<220> FEATURE:
<221> NAME/KEY: misc_feature
<222> LOCATION: (13)..(20)
<223> OTHER INFORMATION: 5 methyl C
<220> FEATURE:
<221> NAME/KEY: misc_feature
<222> LOCATION: (14)..(16)
<223> OTHER INFORMATION: 2' O MOE
<220> FEATURE:
<221> NAME/KEY: misc_feature
<222> LOCATION: (18)..(19)

<223> OTHER INFORMATION: 2' O MOE

<400> SEQUENCE: 31
gcccaagctg gcauccguca                                           20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct

<400> SEQUENCE: 32
tcccgcctgt gacatgcatt                                           20

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
gcccaagctg gcatccgtca                                           20

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
gcgtttgctc ttcttcttgc g                                         21

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
gttctcgctg gtgagtttca                                           20

<210> SEQ ID NO 36
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(21)
<223> OTHER INFORMATION: 2' O MOE

<400> SEQUENCE: 36
gcccaagctg gcatcccgtc a                                         21

<210> SEQ ID NO 37
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature

```
<222> LOCATION: (13)..(20)
<223> OTHER INFORMATION: 2' O MOE

<400> SEQUENCE: 37
tcccgcctgt gacatgcatt                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic construct

<400> SEQUENCE: 38
gcccaagctg gcauccguca                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: 5 methyl C
<220> FEATURE:
<221> NAME/KEY: misc_feature
<222> LOCATION: (8)..(8)
<223> OTHER INFORMATION: 5 methyl C
<220> FEATURE:
<221> NAME/KEY: misc_feature
<222> LOCATION: (12)..(12)
<223> OTHER INFORMATION: 5 methyl C
<220> FEATURE:
<221> NAME/KEY: misc_feature
<222> LOCATION: (13)..(20)
<223> OTHER INFORMATION: 2' O MOE
<220> FEATURE:
<221> NAME/KEY: misc_feature
<222> LOCATION: (14)..(16)
<223> OTHER INFORMATION: 5 methyl U
<220> FEATURE:
<221> NAME/KEY: misc_feature
<222> LOCATION: (18)..(19)
<223> OTHER INFORMATION: 5 methyl U

<400> SEQUENCE: 39
tcccgcctgt gacatgcatt                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic construct

<400> SEQUENCE: 40
gcccaagctg gcatccgtca                                          20

<210> SEQ ID NO 41
<211> LENGTH: 21
<212> TYPE: DNA
<213> ORGANISM: Artificial Sequence
<220> FEATURE:
<223> OTHER INFORMATION: Synthetic construct

<400> SEQUENCE: 41
gcgtttgctc ttcttcttgc g                                        21
```

-continued

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
gttctcgctg gtgagtttca                                           20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
tccgtcatcg ctcctcaggg                                           20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (13)..(20)
<223> OTHER INFORMATION: 2' O MOE

<400> SEQUENCE: 44
tcccgcctgt gacatgcatt                                           20

<210> SEQ ID NO 45
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (12)..(21)
<223> OTHER INFORMATION: 2' O MOE

<400> SEQUENCE: 45
gcccaagctg gcatcccgtc a                                         21

<210> SEQ ID NO 46
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: 5 Methyl C
<220> FEATURE:
<221> NAME/KEY: misc_feature
<222> LOCATION: (8)..(8)
<223> OTHER INFORMATION: 5 Methyl C
<220> FEATURE:
<221> NAME/KEY: misc_feature
<222> LOCATION: (12)..(12)
<223> OTHER INFORMATION: 5 Methyl C
<220> FEATURE:
<221> NAME/KEY: misc_feature
<222> LOCATION: (13)..(20)
<223> OTHER INFORMATION: 2' O MOE

```
<220> FEATURE:
<221> NAME/KEY: misc_feature
<222> LOCATION: (14)..(16)
<223> OTHER INFORMATION: 5 Methyl U
<220> FEATURE:
<221> NAME/KEY: misc_feature
<222> LOCATION: (19)..(19)
<223> OTHER INFORMATION: 5 Methyl U

<400> SEQUENCE: 46
gcccaagctg gcauccguca                                                   20

<210> SEQ ID NO 47
<211> LENGTH: 24
<212> TYPE: DNA
<213> ORGANISM: Artificial Sequence
<220> FEATURE:
<223> OTHER INFORMATION: Synthetic construct

<400> SEQUENCE: 47
gcgtttgctg ctcttcttct tgcg                                              24
```

ACTIVATORS FOR OLIGONUCLEOTIDE SYNTHESIS

CROSS REFERENCE TO RELATED APPLICATIONS

This is a divisional application of Ser. No. 09/708,224, filed Nov. 8, 2000, which is a divisional application of Ser. No. 09/177,953, filed Oct. 23, 1998, now U.S. Pat. No. 6,274,725, which claims benefit of U.S. provisional application No. 60/087,757, filed Jun. 2, 1998, the contents of which are hereby incorporated by reference in their entirety.

FIELD OF THE INVENTION

The present invention relates to improved methods for the preparation of oligonucleotides and nucleoside phosphoramidites. More particularly, the methods utilize activators that have certain advantages over conventional activators used in the preparation of nucleoside phosphoramidites, and in their coupling to form oligomers. More specific objectives and advantages of the invention will hereinafter be made clear or become apparent to those skilled in the art during the course of explanation of preferred embodiments of the invention.

BACKGROUND OF THE INVENTION

The study of oligonucleotides has become a key area of interest for many reasons including potential uses in therapeutic and diagnostic applications (Agrawal, S., TIBTECH, 1996, 14, 375–382; Marr, J., *Drug Discovery Today*, 1996, 1, 94–102; Rush, W., *Science*, 1997, 276, 1192–1193). One of the more interesting applications of oligonucleotides is the ability to modulate gene and protein function in a sequence specific manner. A direct result of studying oligonucleotides including their analogs in variety of applications is the need for large quantities of compounds having high purity. Presently, the synthesis of oligonucleotides and their analogs remains a tedious and costly process. There remains an ongoing need in this area for developing improved synthetic processes that facilitate the synthesis of oligonucleotides.

Phosphoramidites are important building blocks for the synthesis of oligonucleotides. The most commonly used process in oligonucleotide synthesis using solid phase chemistries is the phosphoramidite approach. In a similar process the support used is a soluble support (Bonora et al., *Neucleic Acids Res.*, 1993, 21, 1213–1217). The phosphoramidite approach is also widely used in solution phase chemistries for oligonucleotide synthesis. Deoxyribo-nucleoside phosphoramidite derivatives (Becaucage et al., *Tetrahedron Lett.*, 1981, 22, 1859–1862) have also been used in the synthesis of oligonucleotides.

Phosphoramidites for a variety of nucleosides are commercially available through a myriad of vendors. 3'-O-phosphoramidites are the most widely used amidites but the synthesis of oligonucleotides can involve the use of 5'-O-and 2'-O-phosphoramidites (Wagner et al., *Neuclosides & Neuclotides*, 1997, 17, 1657–1660; Bhan et al., *Neuclosides & Neuclotides*, 1997, 17, 1195–1199). There are also many phosphoramidites available that are not nucleosides (Cruachem Inc., Dulles, Va.; Clontech, Palo Alto, Calif.).

One of the steps in the phosphoramidite approach to oligonucleotide synthesis is the 3'-O-phosphitylation of 5'-O-protected nucleosides. Additionally, exocyclic amino groups and other functional groups present on nucleobase moieties are normally protected prior to phosphitylation.

Traditionally phosphitylation of nucleosides is performed by treatment of the protected nucleosides with a phosphitylating reagent such as chloro-(2-cyanoethoxy)-N,N-diisopropylaminophosphine which is very reactive and does not require an activator or 2-cyanoethyl-N,N,N',N'-tetraisopropylphosphorodiamidite (bis amidite reagent) which requires an activator. After preparation the nucleoside 3'-O-phosphoramidite is coupled to a 5'-OH group of a nucleoside, nucleotide, oligonucleoside or oligonucleotide.

The activator most commonly used in phosphitylation reactions is 1H-tetrazole. There are inherent problems with the use of 1H-tetrazole, especially when performing larger scale syntheses. For example, 1H-tetrazole is known to be explosive. According to the material safety data sheet (MSDS) 1H-tetrazole (1H-tetrazole, 98%) can be harmful if inhaled, ingested or absorbed through the skin. The MSDS also states that 1H-tetrazole can explode if heated above its melting temperature of 155° C. and may form very sensitive explosive metallic compounds. In addition, 1H-tetrazole is known to Hence 1H-tetrazole requires special handling during its storage, use, and disposal.

Aside from its toxicity and explosive nature 1H-tetrazole is acidic and can cause deblocking of the 5'-O-protecting group and can also cause depurination during the phosphitylation step of amidite synthesis (Krotz et al., *Tetrahedron Lett.*, 1997, 38, 3875–3878). Inadvertent deblocking of the 5'-O-protecting group is also a problem when chloro-(2-cyanoethoxy)-N,N-diisopropylaminophosphine is used. Recently, trimethylchlorosilane has been used as an activator in the phosphitylation of 5'-O-DMT nucleosides with bis amidite reagent but this reagent is usually contaminated with HCl which leads to deprotection and formation of undesired products (Dabkowski, W., et al. *Chem. Comm.*, 1997, 877). The results for this phosphitylation are comparable to those for 1H-tetrazole.

Activators with a higher pKa (i.e., less acidic) than 1H-tetrazole (pKa 4.9) such as 4,5-dicyanoimidazole (pKa 5.2) have been used in the phosphitylation of 5'-O-DMT thymidine (Vargeese, C., *Neucleic Acids Res.*, 1998, 26, 1046–1050).

A variety of activators have been used in the coupling of phosphoramidites in addition to 1H-tetrazole. 5-Ethylthio-1H-tetrazole (Wincott, F., et al., *Nucleic Acids Res.* 1995, 23, 2677) and 5-(4-nitrophenyl)-1H-tetrazole (Pon, R. T., *Tetrahedron Lett.*, 1987, 28, 3643) have been used for the coupling of sterically crowded ribonucleoside monomers e.g. for RNA-synthesis. The pKa's for theses activators are 4.28 and 3.7 (1:1 ethanol:water), respectively. The use of pyridine hydrochloride/imidazole (pKa 5.23 (water)) as an activator for coupling of monomers was demonstrated by the synthesis of a dimer (Gryaznov, S. M., Letsinger, L. M., *Neucleic Acids Res.*, 1992, 20, 1879). Benzimidazolium triflate (pKa 4.5 (1:1 ethanol:water)) (Hayakawa et al., *J. Org. Chem.*, 1996, 61, 7996–7997) has been used as an activator for the synthesis of oligonucleotides having bulky or sterically crowded phosphorus protecting groups such as aryloxy groups. The use of imidazolium triflate (pKa 6.9 (water)) was demonstrated for the synthesis of a dimer in solution (Hayakawa, Y.; Kataoka, M., *Nucleic Acids and Related Macromolecules: Synthesis, Structure, Function and Applications*, Sep. 4–9, 1997, Ulm, Germany). The use of 4,5-dicyanoimidazole as an activator for the synthesis of nucleoside phosphoramidite and several 2'-modified oligonucleotides including phosphorothioates has also been reported (Vargeese, supra.).

Another disadvantage to using 1H-tetrazole is the cost of the reagent. The 1997 Aldrich Chemical Company catalog lists 1H-tetrazole at over ten dollars a gram for 98% material. The 99+% pure material lists for over forty seven dollars per gram. This reagent is used in excess of the stoichiometric amount of nucleoside present in the reaction mixture resulting in considerable cost especially during large scale syntheses.

The solubility of 1H-tetrazole is also a factor in the large scale synthesis of phosphoramidites, oligonucleotides and their analogs. The solubility of 1H-tetrazole is about 0.5 M in acetonitrile. This low solubility is a limiting factor on the volume of solvent that is necessary to run a phosphitylation reaction. An activator having higher solubility would be preferred to allow the use of minimum volumes of reactions thereby also lowering the cost and the production of waste effluents. Furthermore, commonly used 1H-tetrazole (0.45 M solution) for oligonucleotide synthesis precipitates 1H-tetrazole when the room-temperature drops below 20° C. Thus, blocking the lines on the automated synthesizer.

Due to ongoing clinical demand (See, for example, Crooke et al., *Biotechnology and Genetic Engineering Reviews*, 1998, 15, 121–157) the synthesis of oligonucleotides and their analogs is being performed utilizing increasingly larger scale reactions than in the past. One of the most common processes used in the synthesis of these compounds utilizes phosphoramidites that are routinely prepared and used in conjunction with an activator. There exists a need for phosphitylation activators that poses less hazards, are less acidic, and less expensive than activating agents that are currently being used, such as 1H-tetrazole. This invention is directed to this, as well as other, important ends.

SUMMARY OF THE INVENTION

In one aspect, the present invention presents improved methods for preparing phosphitylated compounds comprising the steps of:
providing a compound having a hydroxyl group;
reacting said compound with a phosphitylating reagent in the presence of a pyridinium salt in a solvent under conditions of time, temperature and pressure effective to yield said phosphitylated compound.

In some preferred embodiments of the invention, the compound having a hydroxyl group is a nucleoside, preferably a 5'-protected nucleoside having a 3'-hydroxyl group. In further preferred embodiments, the compound is a nucleoside dimer having a 3' or 5'-hydroxyl group. In still further preferred embodiments, said compound is a nucleoside having a 5' or 2' hydroxyl group.

In further preferred embodiments, the compound having a free hydroxyl group is an oligonucleotide or oligonucleotide analog having a 3' or 5' hydroxyl group.

In some preferred embodiments of the invention, the phosphitylating reagent is bis amidite reagent (2-cyanoethyl-N,N,N',N'-tetraisopropylphosphorodiamidite), bis(N,N-diisopropylamino)-2-methyltrifluoroacetylaminoethoxyphosphine or bis(N,N-diisopropylamino)-2-diphenylmethylsilylethoxyphosphine.

In further preferred embodiments of the invention, the pyridinium salt is pyridinium hydrochloride, pyridinium trifluoroacetate or pyridinium dichloroacetate.

In further preferred embodiments of the invention, the solvent is dichloromethane, acetonitrile, ethyl acetate, tetrahydrofuran or a mixture thereof.

In further preferred embodiments, the activator is bound to a solid support. In Still further preferred embodiments, the activator is a polyvinyl pyridinium salt.

In a further aspect, the present invention provides improved methods for the preparation of intersugar linkages. In preferred embodiments, the methods of the invention are used in the preparation of oligonucleotides via standard solid phase oligonucleotide regimes.

In some preferred embodiments, the present invention presents methods for the preparation of a compound of Formula I:

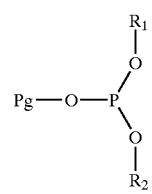

wherein:

R$_1$ is a mononucleoside or an oligonucleotide;

R$_2$ is a nucleoside linked to a solid support, or an oligonucleotide linked to a solid support;

Pg is a phosphorus protecting group; comprising:
providing a phosphoramidite of Formula II:

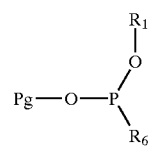

wherein R$_6$ is —N(R$_7$)$_2$ wherein R$_7$ is alkyl having from one to about six carbons; or R$_7$ is a heterocycloalkyl or heterocycloalkenyl ring containing from 4 to 7 atoms, and having up to 3 heteroatoms selected from nitrogen, sulfur, and oxygen;

and reacting said phosphoramidite with a hydroxyl group of a nucleoside linked to a solid support, or an oligonucleotide linked to a solid support;

said reaction being performed in the presence of an activating reagent, said activating reagent comprising at least one pyridinium salt and at least one substituted imidazole.

Also provided in accordance with the present invention are methods for the preparation of an oligonucleotide comprising the steps of:

providing a 3'-mononucleoside phosphoramidite or 3'-oligonucleotide phosphoramidite; and reacting said 3'-mononucleoside phosphoramidite or 3'-oligonucleotide phosphoramidite with the 5'-hydroxyl of a nucleoside, nucleotide, or oligonucleotide in the presence of an activating reagent;

said activating reagent comprising at least one pyridinium salt and at least one substituted imidazole.

In some preferred embodiments, the 3'-mononucleoside phosphoramidite or oligonucleotide phosphoramidite is reacted with the 5'-hydroxyl of a solid-support bound nucleoside, nucleotide or oligonucleotide.

In further preferred embodiments of the foregoing methods of the invention, the oligonucleotide comprises phosphorothioate intersugar linkages.

The present invention also provides synthetic methods comprising: providing a phosphoramidite of Formula II:

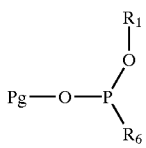

II wherein
R₁ is a mononucleoside or an oligonucleotide;
Pg is a phosphorus protecting group;
R₆ is —N(R₇)₂ wherein R₇ is alkyl having from one to about six carbons; or R₇ is a heterocycloalkyl or heterocycloalkenyl ring containing from 4 to 7 atoms, and having up to 3 heteroatoms selected from nitrogen, sulfur, and oxygen; and
reacting said phosphoramidite with a hydroxyl group of a nucleoside linked to a solid support, or an oligonucleotide linked to a solid support, to form a compound of Formula I:

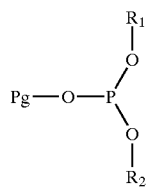

I said reaction being performed in the presence of an activating reagent, said activating reagent comprising at least one pyridinium salt and at least one substituted imidazole; and
oxidizing or sulfurizing said compound to form a compound of Formula III:

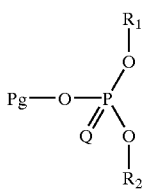

III wherein Q is O or S, with S being preferred.

In some preferred embodiments of the forgoing methods, the substituted imidazole is 1-methylimidazole.

In further preferred embodiments of the foregoing methods, the pyridinium salt has the formula

where X⁻ is trifluoroacetate, ⁻O-mesyl, ⁻O-tosyl, ⁻Br, ⁻O-trifluorosulfonyl, hexafluorophosphate or tetrafluoroborate, with trifluoroacetate being preferred.

In a further aspect of the invention, synthetic methods are provided comprising:

providing a compound of Formula X:

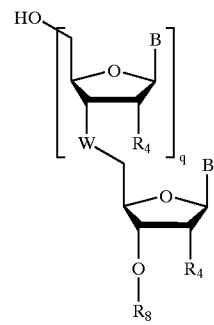

X wherein:
B is a nucleobase;
R₈ is H, a hydroxyl protecting group, or a linker connected to a solid support;
W is an optionally protected internucleoside linkage;
q is 0 to about 50;
R₄ is H, F, O—R, S—R or N—R (R₁₀);
R is H, a protecting group, or has one of the formulas:

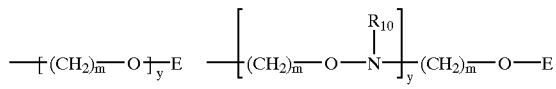

where
each m is independently from 1 to 10;
y is from 0 to 10;
E is H, a hydroxyl protecting group, C₁–C₁₀ alkyl, N(R₁₀)(R₁₁) or N=C(R₁₀)(R₁₁); substituted or unsubstituted C₁–C₁₀ alkyl, C₂–C₁₀ alkenyl, C₂–C₁₀ alkynyl, wherein the substitutions are selected from one or several halogen, cyano, carboxy, hydroxy, nitro and mercapto residues;
each R₁₀ or R₁₁ is, independently, H, substituted or unsubstituted C₁–C₁₀ alkyl, C₂–C₁₀ alkenyl, C₂–C₁₀ alkynyl, wherein the substitutions are selected from one or several halogen, cyano, carboxy, hydroxy, nitro and mercapto residues; alkylthioalkyl, a nitrogen protecting group, or R₁₀ and R₁₁, together, are a nitrogen protecting group or wherein R₁₀ and R₁₁ are joined in a ring structure that can include at least one heteroatom selected from N and O;
or R is —CH₂—CH₂—O—CH₂—CH₂—N(R₁₀)(R₁₁);

reacting the compound of Formula X in the presence of an activating reagent with a compound of Formula XI:

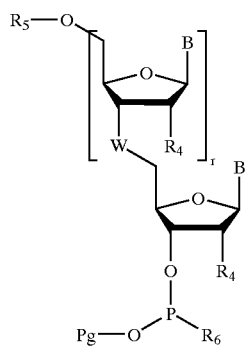

where r is 0 to about 50;
R$_5$ is a hydroxyl protecting group;
R$_6$ is —N(R$_7$)$_2$ wherein R$_7$ is alkyl having from one to about six carbons; or R$_7$ is a heterocycloalkyl or heterocycloalkenyl ring containing from 4 to 7 atoms, and having up to 3 heteroatoms selected from nitrogen, sulfur, and oxygen;
to form a compound of Formula XII:

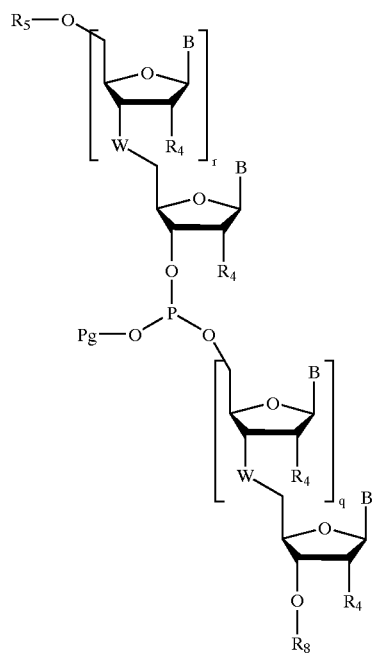

wherein said activating reagent comprises at least one pyridinium salt and one substituted imidazole.

In some preferred embodiments, the pyridinium salt has the formula:

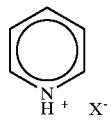

where X$^-$ is trifluoroacetate, $^-$O-mesyl, $^-$O-tosyl, $^-$Br, $^-$O-trifluorosulfonyl, hexafluorophosphate, or tetrafluoroborate, with trifluoroacetate being preferred.

In further preferred embodiments, the substituted imidazole is 1-methylimidazole.

In some preferred embodiments, R$_8$ is a linker connected to a solid support.

In further preferred embodiments, R$_4$ is —O—R wherein R has the formula —[—(CH$_2$)$_m$—O—]$_y$—E; m is 2, y is 1; and E is CH$_3$, —N(R$_{10}$)(R$_{11}$), or —CH$_2$—CH$_2$—N(R$_{10}$)(R$_{11}$).

In further preferred embodiments, r is 0. In still further preferred embodiments, R$_6$ is diisopropylamino.

Preferably, Pg is —CH$_2$CH$_2$CN, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, or —CH$_2$CH$_2$N(CH$_3$)COCF$_3$. with —CH$_2$CH$_2$CN being more preferred.

Some preferred embodiment of the methods further comprising oxidizing or sulfurizing the compound of Formula XII to form a compound of Formula XIII:

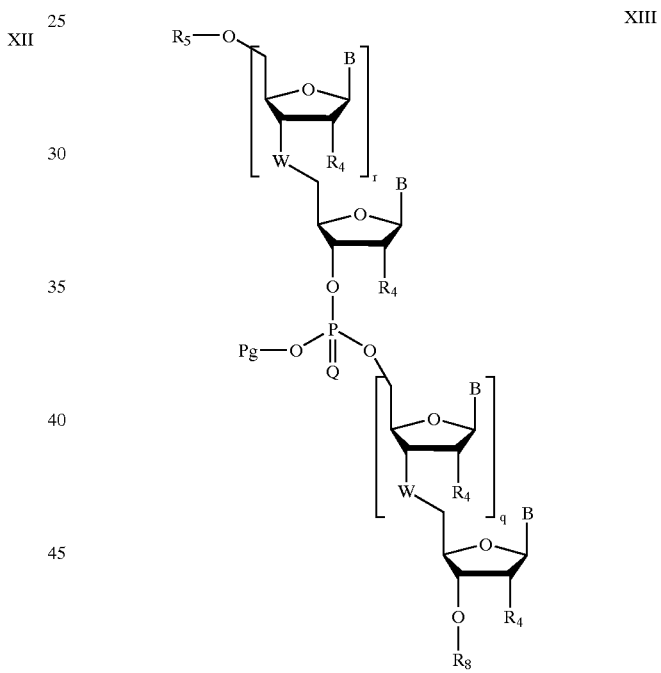

where Q is O or S, with S being preferred.

Some further preferred embodiments of the methods further comprising a capping step, which is preferably performed prior to oxidation.

Some further preferred embodiments further comprising the step of cleaving the oligomeric compound to produce a further compound of formula X.

In a further aspect of the invention, methods are provided for the preparation of internucleoside linkages between nucleosides having 2'-substituents, using an activating reagent that is preferably an imidazolium triflate. In some preferred embodiments, these methods comprise: providing a compound of Formula X:

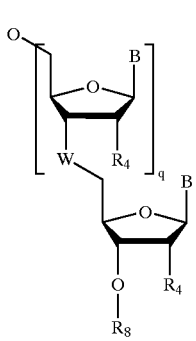

X wherein:

B is a nucleobase;

$R_8$ is H, a hydroxyl protecting group, or a linker connected to a solid support;

W is an optionally protected internucleoside linkage;

q is 0 to about 50;

$R_4$ is H, F, O—R, S—R or N—R($R_{10}$);

R is H, a protecting group, or has one of the formulas:

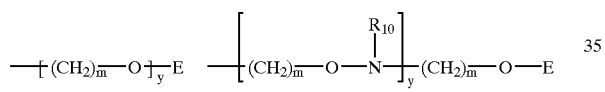

where each m is independently from 1 to 10;

y is from 0 to 10;

E is H, a hydroxyl protecting group, $C_1$–$C_{10}$ alkyl, N($R_{10}$)($R_{11}$) or N=C($R_{10}$)($R_{11}$); substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and each $R_{10}$ or $R_{11}$ is, independently, H, substituted or unsubstituted $C_1$–$C_{10}$ alkyl, $C_2$–$C_{10}$ alkenyl, $C_2$–$Cl_0$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$, are joined in a ring structure that can include at least one heteroatom selected from N and O;

or R is —$CH_2$—$CH_2$—O—$CH_2$—$CH_2$—N($R_{10}$)($R_{11}$);

provided that $R_{14}$ is not H or OH;

reacting the compound of Formula X in the presence of an activator with a compound of Formula XI:

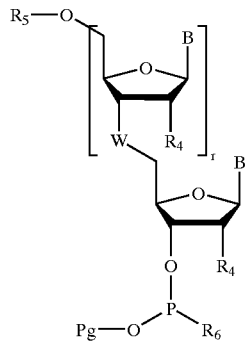

XI where r is 0 to about 50;

$R_5$ is a hydroxyl protecting group;

$R_6$ is —N($R_7$)$_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen; to form a compound of Formula XII:

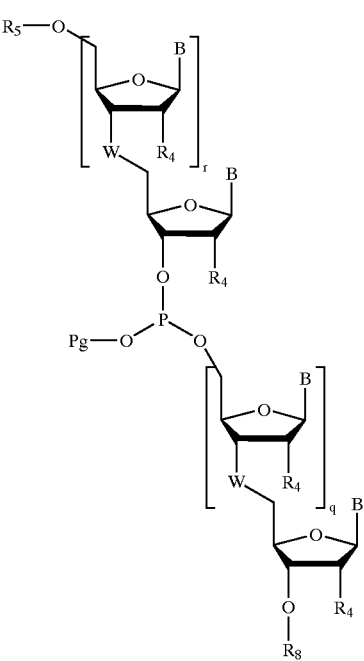

XII wherein the activator has the formula $G^+U^-$, where $G^+$ is selected from the group consisting of pyridinium, imidazolium, and benzimidazolium; and $U^-$ is selected from the group consisting of hexafluorophosphate, tetrafluoroborate, triflate, hydrochloride, trifluoroacetate, dichloroacetate, $^-$O-mesyl, $^-$O-tosyl, $^-$Br, and $^-$O-trifluorosulfonyl.

Preferably, the activator is imidazolium triflate.

In some preferred embodiments, $R_8$ is a linker connected to a solid support. In further preferred embodiments, $R_4$ is is —O—R wherein R has the formula —[—($CH_2$)$_m$—O—]$_y$—E; m is 2, y is 1; and E is $CH_3$, —N($R_{10}$)($R_{11}$), or —$CH_2$—$CH_2$—N($R_{10}$)($R_{11}$).

In further preferred embodiments, r is 0. In still further preferred embodiments, $R_6$ is diisopropylamino.

Preferably, Pg is —$CH_2CH_2CN$, —$CH_2CH$=$CHCH_2CN$, para—$CH_2C_6H_4CH_2CN$, —$(CH_2)_{2-5}N(H)COCF_3$, —$CH_2CH_2Si(C_6H_5)_2CH_3$, or —$CH_2CH_2N(CH_3)COCF_3$, with —$CH_2CH_2CN$ being more preferred.

Some further preferred embodiments further comprise oxidizing or sulfurizing the compound of Formula XII to form a compound of Formula XIII:

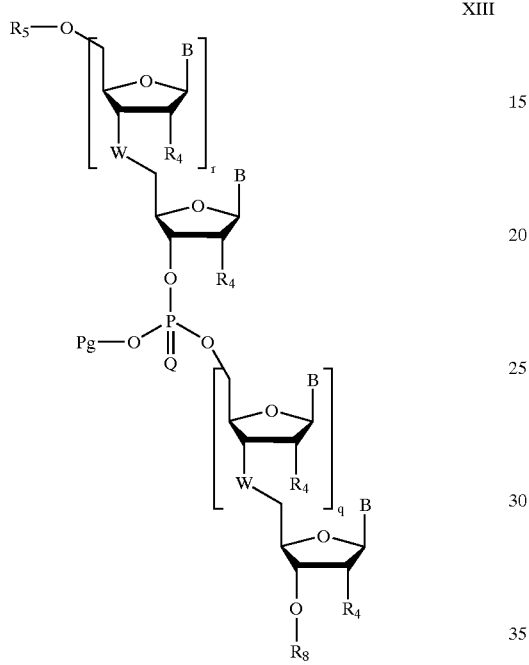

XIII where Q is O or S, with S being preferred.

Some further preferred embodiments of the methods further comprising a capping step, which is preferably performed prior to oxidation.

Some further preferred embodiments further comprising the step of cleaving the oligomeric compound to produce a further compound of formula X.

In a further aspect of the invention, synthetic methods are provided comprising:
providing a compound of Formula XX:

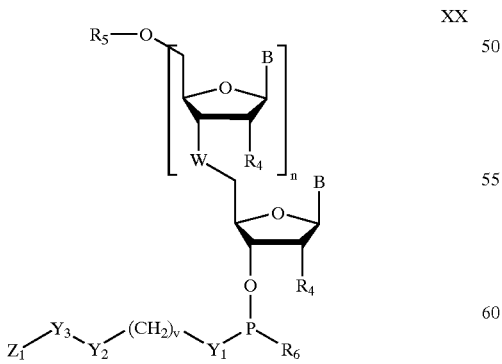

XX wherein:
$R_4$ is H, F, O—R, S—R or N—R $(R_{10})$;
R is H, a protecting group, or has one of the formulas:

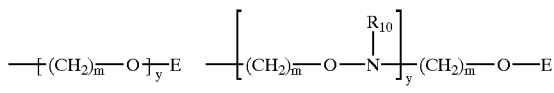

where
each m is independently from 1 to 10;
y is from 0 to 10;
E is H, a hydroxyl protecting group, $C_1$–$C_{10}$ alkyl, $N(R_{10})(R_{11})$ or N=C $(R_{10})(R_{11})$; substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; alkylthioalkyl, a nitrogen protecting group, or R and $R_{10}$, together, are a nitrogen protecting group or wherein R and $R_2$ are joined in a ring structure that can include at least one heteroatom selected from N and O;
or R is —$CH_2$—$CH_2$—O—$CH_2$—$CH_2$—$N(R_{10})$ $(R_{11})$;
$R_5$ is a hydroxyl protecting group;
$Z_1$ is aryl having 6 to about 14 carbon atoms or alkyl having from one to about six carbon atoms;
$Y_1$ is O or S;
$Y_2$ is O or S;
$Y_3$ is C(=O) or S;
v is 2 to about 4;
B is a nucleobase;
$R_6$ is —$N(R_7)_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen;

reacting said compound of Formula XX with a compound of Formula XXI:

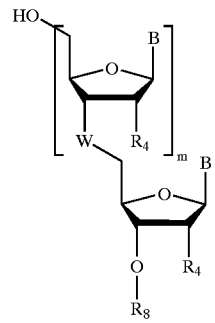

XXI wherein:
$R_8$ is H, a hydroxyl protecting group, or a linker connected to a solid support;
in the presence of an activator to form a compound of Formula XXII:

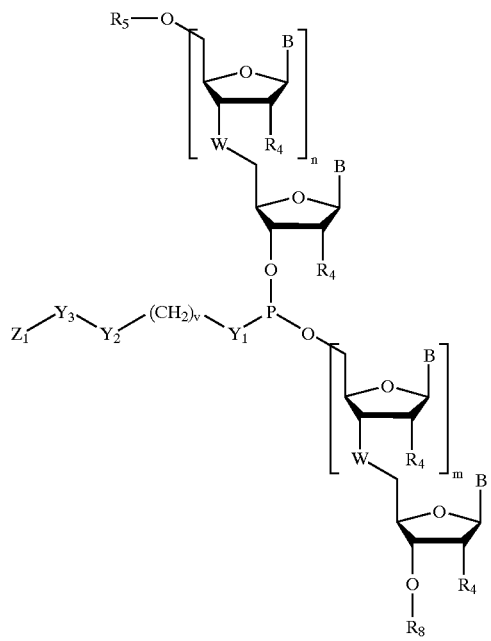

XXII

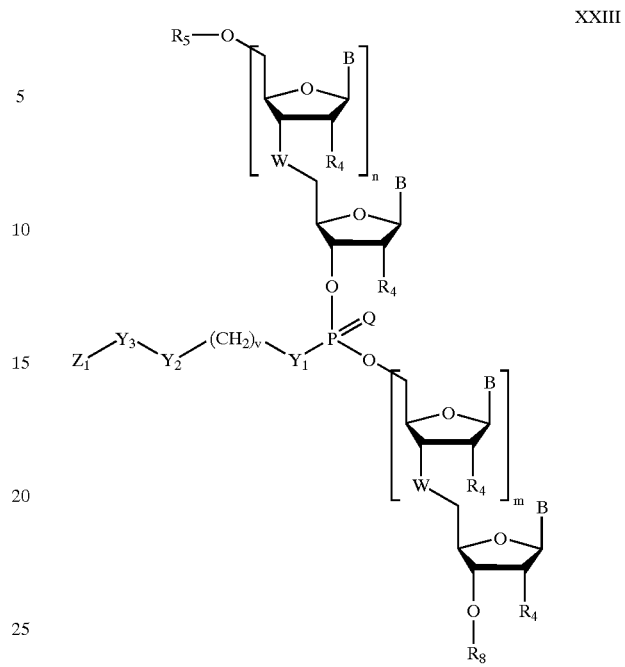

XXIII wherein the activator has the formula $G^+U^-$, where
G⁻ is selected from the group consisting of pyridinium, imidazolium, and benzimidazolium; and U⁻ is selected from the group consisting of hexafluorophosphate, tetrafluoroborate, triflate, hydrochloride, trifluoroacetate, dichloroacetate, ⁻O-mesyl, ⁻O-tosyl, ⁻Br, and ⁻O-trifluorosulfonyl;

or said activator is a substituted imidazolium triflate.

Preferably, the activator is imidazolium triflate.

In some preferred embodiments, v is 2; and $Y_3$ is C(=O). In further preferred embodiments, Z is methyl, phenyl or t-butyl, with t-butyl being preferred.

In some preferred embodiments, n is 0. In further preferred embodiments, $R_8$ is a linker to a solid support.

In some preferred embodiments, $Y_1$ and $Y_2$ are each O. I other preferred embodiments, $Y_1$ and $Y_2$ are each S. In still further preferred embodiments, $Y_1$ is O and $Y_2$ is S.

Preferably, each $R_7$ is isopropyl.

In some preferred embodiments, n is 0; $R_3$ is H, $R_6$ is diisopropylamino; $Y_1$ is O; $Y_2$ is S; and Z is methyl or t-butyl, with t-butyl being preferred.

In some preferred embodiments of each of the foregoing methods, each constituent nucleobase "B" is devoid of exocyclic amine protection.

Preferably, W is an optionally protected phosphodiester, phosphorothioate, phosphorodithioate, or alkyl phosphonate internucleotide linkage.

Some preferred embodiments of the foregoing methods further comprise oxidizing or sulfurizing the compounds of Formula XXII to form a compound of Formula XXIII:

where Q is O or S.

Some further preferred embodiments of the methods further comprising a capping step, which is preferably performed prior to oxidation.

Some further preferred embodiments further comprising the step of cleaving the oligomeric compound to produce a further compound of formula XXI.

In some preferred embodiments, G⁺ is pyridinium and U⁻ is hexafluorophosphate or tetrafluoroborate, with hexafouoroborate being preferred.

In further preferred embodiments, G⁺ is imidazolium or benzimidazolium and U⁻ is selected from the group consisting of triflate, hydrochloride, trifluoroacetate, dichloroacetate, ⁻O-mesyl, ⁻O-tosyl, ⁻Br, and ⁻O-trifluorosulfonyl.

In other preferred embodiments, G⁺ is imidazolium or benzimidazolium and U⁻ is selected from the group consisting of hexafluorophosphate, tetrafluoroborate, and triflate.

In further preferred embodiments, G⁺ is imidazolium or benzimidazolium and U⁻ is selected from the group consisting of hydrochloride, trifluoroacetate, dichloroacetate, ⁻O-mesyl, ⁻O-tosyl, ⁻Br, and ⁻O-trifluorosulfonyl.

In still further preferred embodiments, G⁺ is imidazolium and U⁻ is selected from the group consisting of hexafluorophosphate, tetrafluoroborate, triflate, hydrochloride, trifluoroacetate, dichloroacetate, ⁻O-mesyl, ⁻O-tosyl, ⁻Br, and ⁻O-trifluorosulfonyl.

In still further preferred embodiments, U⁻ is selected from the group consisting of hexafluorophosphate, tetrafluoroborate, and triflate.

In further preferred embodiments, U⁻ is selected from the group consisting of hydrochloride, trifluoroacetate, dichloroacetate, ⁻O-mesyl, ⁻O-tosyl, ⁻Br, and ⁻O-trifluorosulfonyl.

In further preferred embodiments, G⁺ is benzimidazolium and U⁻ is selected from the group consisting of hexafluorophosphate, tetrafluoroborate, triflate, hydrochloride, trifluoroacetate, dichloroacetate, ⁻O-mesyl, ⁻O-tosyl, ⁻Br, and ⁻O-trifluorosulfonyl.

In further preferred embodiments, G⁺ is benzimidazolium and U⁻ is hexafluorophosphate, tetrafluoroborate, or triflate.

In further preferred embodiments, G⁺ is benzimidazolium and U⁻ is selected from the group consisting of hydrochloride, trifluoroacetate, dichloroacetate, ⁻O-mesyl, ⁻O-tosyl, ⁻Br, and ⁻O-trifluorosulfonyl.

In some prefered embodiments, the activator is substituted or unsubstituted imidazolium triflate, with unsubstituted imidazolium triflate being preferred.

DESCRIPTION OF PREFERRED EMBODIMENTS

Figure 1:
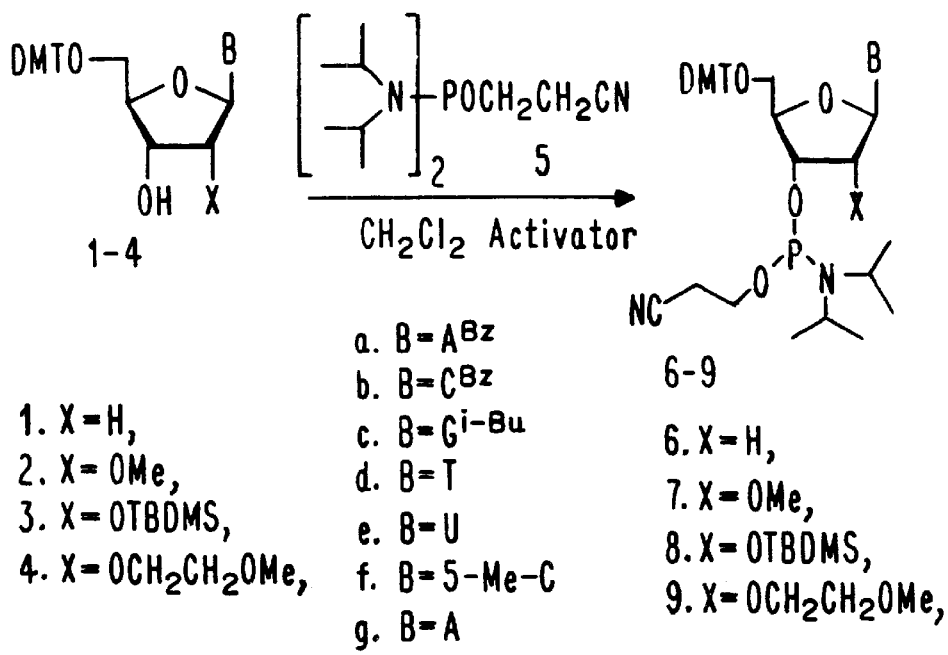
FIG. 1 is a scheme showing intermediates and products in a series of phosphitylation reactions according to the invention.
Figure 1:
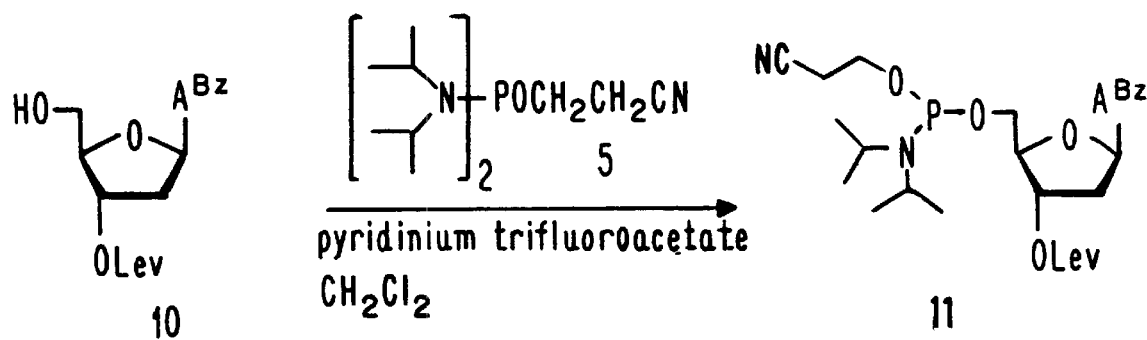

The present invention describes improved methods for, inter alia, phosphitylating compounds having a free ("unblocked") hydroxyl group. In some preferred embodiments, the compound to be phosphitylated is a mononucleoside, an oligonucleotide, or analog thereof.

A large number of compounds are amenable to the improved process of the present invention. A general scheme utilizing some preferred starting materials is illustrated below:

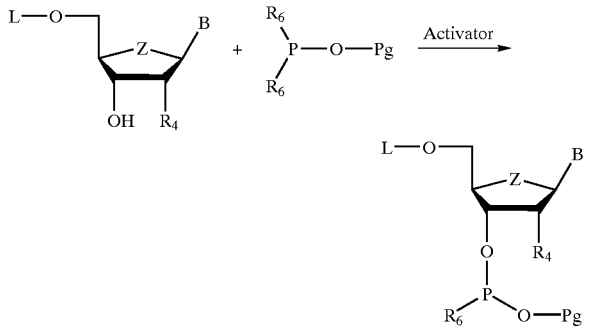

wherein
L is a hydroxyl protecting group, a nucleotide, a nucleoside, an oligonucleotide or and oligonucleoside;
Z is O, S, $CH_2$ or $NR_{10}$;
B is a nucleobase or a modified nucleobase;
Pg is a phosphorus protecting group that is preferably $-CH_2CH_2CN$, $-CH_2CH=CHCH_2CN$, para-$CH_2C_6H_4CH_2CN$, $-(CH_2)_{2-5}N(H)COCF_3$, $-CH_2CH_2Si(C_6H_5)_2CH_3$, or $-CH_2CH_2N(CH_3)COCF_3$;
$R_4$ is H, F, O—R, S—R or N—$R(R_{10})$;

R is H, a protecting group, or has one of the formulas:

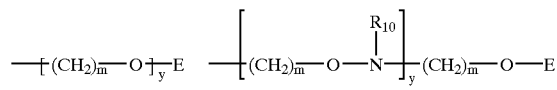

where
each m is independently from 1 to 10;
y is from 0 to 10;
E is H, a hydroxyl protecting group, $C_1$–$C_{10}$ alkyl, $N(R_{10})(R_{11})$ or $N=C(R_{10})(R_{11})$; substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$, are joined in a ring structure that can include at least one heteroatom selected from N and O; or R is $-CH_2-CH_2-O-CH_2-CH_2-N(R_{10})(R_{11})$.

The initial step in the phosphitylation scheme illustrated above is the activation of the phosphorus atom of the phosphitylating reagent via protonation. The activator donates a proton to the phosphorus atom of the phosphitylating reagent (i.e., a $P^{III}$ compound having at least one phosphorus/oxygen bond) thereby activating the reagent. The activation involves formation of a salt with the corresponding anion of the activator. When the phosphitylating reagent is activated the phosphorus atom undergoes nucleophilic attack by a free hydroxyl group displacing a diisopropylamino group which forms a salt with the anion of the activator. As depicted above the free hydroxyl group is a 3' hydroxyl group but the attacking nucleophile could alternatively be a 5' hydroxyl group (Wagner, T., and Pfleiderer, W., *Neuclosides & Nucleotides*, 1997, 16, 1657–1660) or a 2' hydroxyl group (Bhan et al., *Neuclosides & Neuclotides*, 1997, 16, 1195–1199). The nucleophilic attack results in the formation of a stable phosphoramidite ($P^{III}$)) compound.

In addition to phosphitylation of 3' hydroxyl positions of nucleosides or larger oligomeric structures the present invention is also amenable to phosphitylation of 5', 2', and 1' hydroxyl positions. The present process is also amenable to compounds other than nucleosides. All that is required is that the compound have an unblocked hydroxyl group and be inert to the reaction conditions of phosphitylation, or, for example, be rendered inert to the reaction conditions by addition of appropriate protecting groups if necessary. There are numerous examples in the literature of phosphitylation of non-nucleosidic compounds such as for example: alkyl groups (Filippov et al., *Neuclosides & Neuclotides*, 1997, 16, 1403–1406); cyclohexoses (Schlienger et al., *Neuclosides & Nucleotides*, 1997, 16, 1325–1329); peptide nucleic acid (Vinayak et al., *Neuclosides & Neuclotides*, 1997, 16, 1653–1656); macrocyclic ligands (Wagner et al., *Neuclosides & Neuclotides*, 1997, 17, 1789–1792), European Patent Application no. EP 0 816 368 Al, entitled "Chemical Phosphorylation of oligonucleotides and Reactants used therefor, filed Jul. 2, 1997, published Jan. 7, 1998.

In preferred embodiments, the methods of the present invention use pyridinium salts as activators during the synthesis of phosphoramidites. Thus, the methods of the invention possess significant advantages over conventional phosphitylation processes. For example, the activators of the present invention can be generated in situ by mixing equal molar amounts of the base pyridine and an acid such as for example HCl, $CF_3COOH$, $CHCl_2COOH$ or $CF_3SO_3H$ (trifluoro-methylsulfonic acid). The in situ preparation of activators is quick, easy and provides significant benefit in the performance synthesis of phosphoramidites on a large scale. Particularly, at the oligonucleotide manufacturing site, where pyridine and $CHCl_2COOH$ both are used as synthesis reagents, are also useful for the preparation of activator.

The mechanism of phosphoramidite activation has been studied (Vargeese, supra; Dahl et al., *Nucleic Acids Research*, 1987, 15, 1729–1743). The first step is the protonation of the trivalent phosphorus. The next step which is slower is the displacement of N,N-diisopropylamine by an activator such as 1-H tetrazole. Typically, in the phosphitylation step of amidite based oligonucleotide synthesis, the 1-H tetrazole first participates as an acid, and then as a nucleophile.

Although not wanting to be bound by theory it is thought that the mechanism of phosphitylation observed for the preferred pyridinium salts of the invention are not the same as when 1-H tetrazole is employed. As illustrated in the series of experiments of Example 12, the first step is seen as protonation of the phosphitylating reagent via proton transfer from the activator. The second step is seen as the reaction of the activated phosphitylating species directly with the 3'-hydroxyl group of the nucleoside. Hence, the pyridine is not seen as a nucleophilic participant in the reaction scheme.

Pyridinium salts are non-explosive which make them substantially easier to store, use and dispose of relative to conventional activators such as 1H-tetrazole. Pyridinium salts and the starting materials necessary to generate them in situ., are safely stored in large quantities. The removal of pyridinium ion from reaction mixtures is easily performed by conversion to pyridine which is easily removed by evaporation. Furthermore, the cost of pyridinium salt is only $0.10/gram compared to $47.00/gram for 1H-tetrazole. This cost differential results in substantive cost-savings for large scale manufacture of oligonucleotide drugs.

Another advantage that pyridinium salts have over conventional activators is their solubility in organic solvents. The solubility of pyridinium salts is significantly higher in solvents such as acetonitrile, dichloromethane, and ethyl acetate than 1H-tetrazole. For example the of pyridinium trifloroacetate in acetonitrile is greater than 1 molar which is more than twice the solubility of 1H-tetrazole in acetonitrile which is about 0.5 molar under identical conditions. As a result of this increased solubility the volume of solvents used during phosphitylation can be greatly reduced. Another result of the increased solubility is that other solvent systems can be used giving enhanced results that are not feasible with activators such as 1H-tetrazole. The improved process of the present invention is performed using a solvent that can dissolve protected nucleosides. Preferred solvents include dichloromethane, dichloroethane, acetonitrile, tetrahydrofuran, ethyl acetate and mixtures thereof. In a preferred embodiment the improved process is performed using dichloromethane.

The use of pyridinium salts as activators improves the purity of the final phosphitylated material relative to conventional activators such as 1H-tetrazole. This improved purity results from a less acidic reaction medium when pyridinium salts are used. Pyridinium salts also provide a less acidic reaction environment than is observed when using more reactive phosphitylating reagents such as chloro-(2-cyanoethoxy)-N,N-diisopropylaminophosphine. This reduction in acidity leads to no loss of 5'-O-protection (see Example 9) which is always a problem with conventional more acidic activators. There is also no depurination seen (see Example 11) with the use of pyridinium activators. The fact that there are less undesired products as a result of depurination and deprotection simplifies purification of desired phosphoramidites.

A number of chemical functional groups present in the nucleosidic compounds of the invention can be protected and subsequently deblocked to the deprotected form. In general, a blocking group renders a chemical functionality of a molecule inert to specific reaction conditions and can later be removed from such functionality in a molecule without substantially damaging or altering the remainder of the molecule (Green and Wuts, Protective Groups in Organic Synthesis, 2d edition, John Wiley & Sons, New York, 1991). Common protecting groups that are routinely used during oligonucleotide synthesis are disclosed in Agrawal, et al., Protocols for Oligonucleotide Conjugates, Eds, Humana Press; New Jersey, 1994; Vol. 26 pp. 1–72.

Nucleosidic compounds according to the present invention include monomeric and linked nucleosides. The term "nucleoside" is intended to include naturally occurring nucleosides and nucleosides having modified nucleobases and/or modified sugar moieties. Internucleoside linkages between linked nucleosides comprise native phosphodiester linkages as well as modified linkages such as phosphorothioate linkages. Other internucleoside linkages as is known in the art are also amenable to the present invention.

As used in the present application the term "nucleobase" is intended to include naturally occurring nucleobases such as for example adenine, guanine, cytosine, uridine, and thymine, as well as nucleobases that are modified such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-aza uracil, cytosine and thymine, 5-uracil (pseudo uracil), 4-thio uracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch et al., *Angewandte Chemie, International Edition* 1991, 30, 613, Limbach, A., et al., *Nucleic Acids Research*, 1994, 22, 2183–2196.

Sugar modifications are known in the prior art and include for example 2' substituents such as F and 2'-O-substituents such as substituted or unsubstituted $C_1$–$C_{10}$ alkyl, $C_2$–$C_{10}$ alkenyl, $C_2$–$C_{10}$ alkynyl, ethers and polyethers wherein the substitutions are selected from one or several halogen, cyano, carboxy, hydroxy, nitro and mercapto residues.

Modified internucleoside linkages are known in the prior art and include for example methylphosphonates, monothiophosphates, dithiophosphates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives.

Phosphitylating reagents that are amenable to the present invention require an activating agent prior to being susceptible to nucleophilic attack from an unprotected 2', 3' or 5' hydroxyl group. Included in this group are phos-phitylating reagents having the formula below:

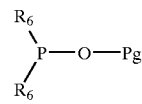

wherein the constituent variables are as defined above.

A more preferred group of phosphitylating reagents includes bis amidite reagent, bis(N,N-diisopropylamino)-2-methyltrifluoroacetylaminoethoxyphosphine and bis(N,N-diiso-propylamino)-2-diphenylmethylsilylethoxyphosphine, and bis(N,N-diisopropylamino)-2-(2'-acetoyloxy) phenylethoxy-phosphine.

In a preferred embodiment of the present invention pyridinium salts used as activators are selected to have Pka's of from about 5.2 to about 5.9. Preferred pyridinium salts in this group include pyridine hydorchloride, pyridinium trifluoroacetate and pyridinium dichloroacetate.

A summary of some phosphitylation activators, their optimal ratio, and exemplary choice of solvent is presented in Table 3 below. Several activators were studied based on their pKa properties, steric bulk/size, cost, safety and scalability during manufacture of phosphoramidites. Also, the activator must act as an acid and have the capacity to transfer a proton to the phosphitylating reagent in an efficient manner. In addition, when phosphitylating 5'-O-DMT-nucleosides the activator should be sufficiently mild to not cause destruction of the acid labile DMT protecting. Activators with pKa between 4.5–7 (see FIG. 2) were chosen and studied herein. One preferred activator is the pyrimidine derivative 2-amino-4,6-dimethylpyrimidine trifluoroacetate.

Some activators reported in the literature, for example 1-H tetrazole and diisopropylammonium tetrazolide, were judged unsuitable due to their high cost, safety in handling, explosive nature, and poor solubility in solvent of choice. Preferred are those derived from pyridinium salts (pyridine hydrochloride, pyridinium trifluoroacetate, pyridinium triflate and pyridinium dichloroacetate) with a common pKa of 5.2. In further preferred embodiments, pyridinium hydrochloride and pyridinium triflate have been shown to be particularly amenable to the methods of the invention, despite the hygroscopic nature of these salts. In particularly preferred embodiments, pyridinium trifluoroacetate activators are employed in the methods of the invention, because they possess an excellent safety profile, low cost, and greater solubility in a range of solvents. Furthermore, the activator pyridinium trifluoroacetate was used to phosphitylate a variety of nucleoside derivatives (1–4, FIG. 1) to provide excellent yields. In further preferred embodiments, pyridinium dichloroacetate (see Example 8) also is useful as an activator in the methods of the invention, and may have an advantage over pyridinium trifluoroacetate because pyridine and dichloroacetic acid is also used as a deblocking solution during oligonucleotide manufacturing, thus avoiding the storage and handling of an addition reagent.

In a further aspect, the present invention provides novel methods for the preparation of covalent intersugar linkages. In some preferred embodiments, the current invention presents methods for the preparation of a compound of Formula I:

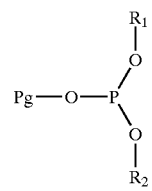

wherein:
R$_1$ is a nucleoside or an oligonucleotide;
R$_2$ is a nucleoside linked to a solid support, or an oligonucleotide linked to a solid support;
Pg is a phosphorus protecting group; comprising:
providing a phosphoramidite of Formula II:

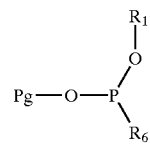

wherein R$_6$ is —N(R$_7$)$_2$ wherein R$_7$ is alkyl having from one to about six carbons; or R$_7$ is a heterocycloalkyl or heterocycloalkenyl ring containing from 4 to 7 atoms, and having up to 3 heteroatoms selected from nitrogen, sulfur, and oxygen;
and reacting said phosphoramidite with a hydroxyl group of a nucleoside linked to a solid support, or an oligonucleotide linked to a solid support;
said reaction being performed in the presence of an activating reagent, said activating reagent comprising at least one pyridinium salt and at least one substituted imidazole.

The methods of the invention are applicable to the reparation of intersugar linkages including those represented by Formula I above. According to some preferred embodiments of the methods of the invention, a protected phosphoramidite having Formula II is reacted with a hydroxyl group of a sugar moiety of a nucleoside or oligonucleotide. In more preferred embodiments, the nucleoside or oligonucleotide are linked to a solid support, as in, for example, standard solid phase oligonucleotide synthetic regimes.

In the methods of the invention, the reaction of the phosphoramidite and the hydroxyl group is performed in the presence of an activating reagent. As used herein, the term "activating reagent" is intended to mean a reagent that, at a minimum, includes at least one pyridinium salt. It is preferred that the activating reagent also contain at least one imidazole or substituted imidazole, in addition to the pyridinium salt.

The reaction of the phosphoramidite and the hydroxyl group in the presence of the activating reagent can be performed in a solvent, such as acetonitrile.

Also provided in accordance with the present invention are methods for the preparation of an oligonucleotide comprising the steps of:
providing a 3'-mononucleoside phosphoramidite or 3'-oligonucleotide phosphoramidite; and
reacting said 3'-mononucleoside phosphoramidite or 3'-oligonucleotide phosphoramidite with the 5'-hydroxyl of a nucleoside, nucleotide, or oligonucleotide in the presence of an activating reagent;
said activating reagent comprising at least one pyridinium salt and at least one substituted imidazole.

In some preferred embodiments, the 3'-mononucleoside phosphoramidite or oligonucleotide phosphoramidite is reacted with the 5'-hydroxyl of a solid-support bound nucleoside, nucleotide or oligonucleotide.

In further preferred embodiments of the methods of the invention, the oligonucleotide comprises phosphorothioate intersugar linkages.

The present invention also provides synthetic methods comprising:

providing a phosphoramidite of formula:

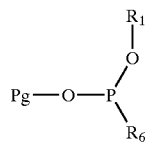

wherein:
$R_6$ is morpholino or dialkylamino;
Pg is a phosphorus protecting group;
and reacting said phosphoramidite with a hydroxyl group of a nucleoside linked to a solid support, or an oligonucleotide linked to a solid support, to form a compound of formula:

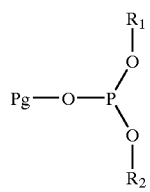

wherein:
$R_1$ is a mononucleoside or an oligonucleotide;
$R_2$ is a nucleoside linked to a solid support, or an oligonucleotide linked to a solid support;
said reaction being performed in the presence of an activating reagent, said activating reagent comprising at least one pyridinium salt and at least one substituted imidazole; and
oxidizing or sulfurizing said compound to form a compound of formula:

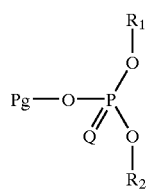

wherein Q is O or S.

In some preferred embodiments of the forgoing methods, the substituted imidazole is 1-methylimidazole.

In further preferred embodiments, the pyridinium salt has the formula

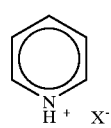

where $X^-$ is an anion such as, for example, trifluoroacetate, $^-$O-mesyl, $^-$O-tosyl, $^-$Br, $^-$O-trifluorosulfonyl, hexafluorophosphate, or tetrafouoroborate, with trifluoroacetate being preferred.

In some preferred embodiments, the compound is a single nucleoside or a nucleoside that is part of a larger molecule such as an oligonucleotide or an oligonucleotide analog. The improved process of the present invention offers significant advantages over traditionally used processes.

In a further aspect of the invention, synthetic methods are provided comprising:

providing a compound of Formula X:

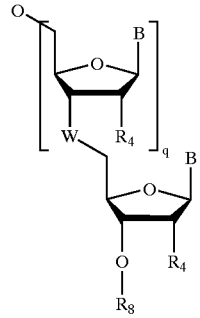

wherein:
B is a nucleobase;
$R_8$ is H, a hydroxyl protecting group, or a linker connected to a solid support;
W is an optionally protected internucleoside linkage;
q is 0 to about 50;
$R_4$ is H, F, O—R, S—R or N—R($R_{10}$);
R is H, a protecting group, or has one of the formulas:

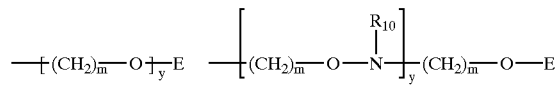

where
each m is independently from 1 to 10;
y is from 0 to 10;
E is H, a hydroxyl protecting group, $C_1$–$C_{10}$ alkyl, N($R_{10}$)($R_{11}$) or N=C($R_{10}$)($R_{11}$); substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$ are joined in a ring structure that can include at least one heteroatom selected from N and O;
or R is —$CH_2$—$CH_2$—O—$CH_2$—$CH_2$—N($R_{10}$)($R_{11}$);
reacting the compound of Formula X in the presence of an activating reagent with a compound of Formula XI:

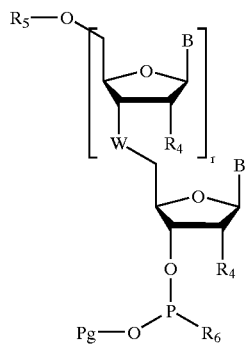

XI where r is 0 to about 50;

$R_5$ is a hydroxyl protecting group;

$R_6$ is $-N(R_7)_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen;

to form a compound of Formula XII:

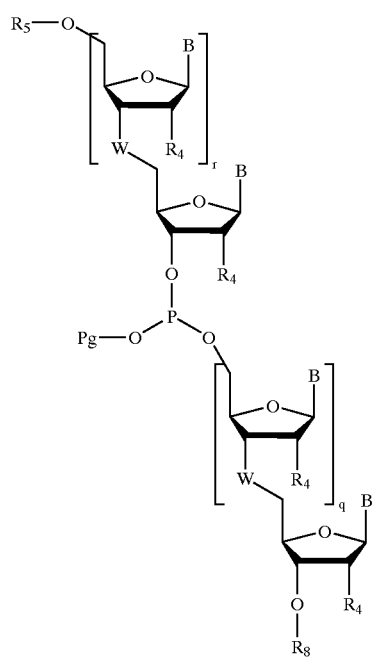

XII wherein said activating reagent comprises at least one pyridinium salt and one substituted imidazole.

Preferably, the activator has the formula $G^+U^-$, where $G^+$ is selected from the group consisting of pyridinium, imidazolium, and benzimidazolium; and $U^-$ is selected from the group consisting of hexafluorophosphate, tetrafluoroborate, triflate, hydrochloride, trifluoroacetate, dichloroacetate, $^-$O-MESYl, $^-$O-tosyl, $^-$Br, and $^-$O-trifluorosulfonyl.

Preferably, the compound of Formula XII can then be oxidized or sulfurized to form a compound of Formula XIII:

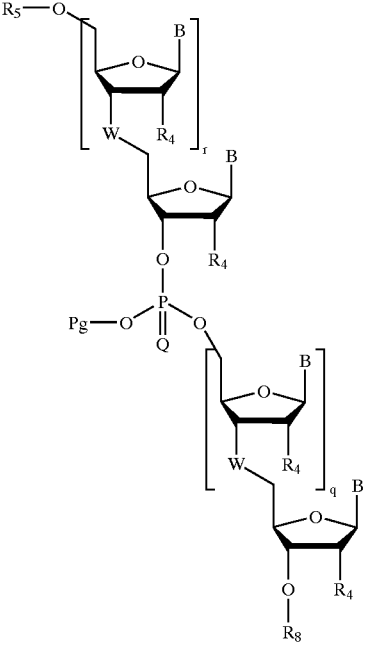

XIII where Q is O or S.

After completion of synthetic regime, the final product is then cleaved from the solid support to produce a further compound of Formula X.

In a further aspect of the invention, methods are provided for the preparation of internucleoside linkages between nucleosides having 2'-substituents, using an imidazolium triflate activating reagent. As used herein, the term "an imidazolium triflate" denotes imidazolium triflate, as well as substituted imidazolium triflates wherein the substituents are one or more electron withdrawing groups such as, for example, halogen, nitro or cyano. Preferably, the activating reagent is unsubstituted imidazolium triflate. In some preferred embodiments, these methods comprise:

providing a compound of Formula X:

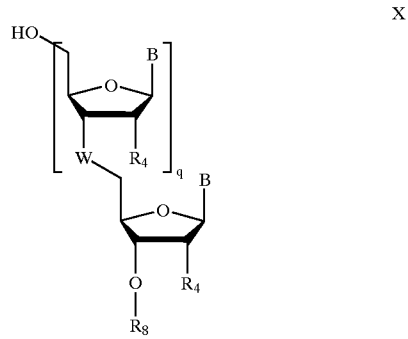

X wherein:

B is a nucleobase;

$R_8$ is H, a hydroxyl protecting group, or a linker connected to a solid support;

W is an optionally protected internucleoside linkage;

q is 0 to about 50;

$R_4$ is H, F, O—R, S—R or N—R($R_{10}$);

R is H, a protecting group, or has one of the formulas:

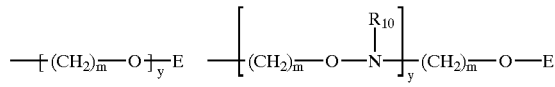

where
each m is independently from 1 to 10;
y is from 0 to 10;
E is H, a hydroxyl protecting group, $C_1$–$C_{10}$ alkyl, N($R_{10}$)($R_{11}$) or N=C($R_{10}$)($R_{11}$); substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and each $R_{10}$ or $R_{11}$ is, independently, H, substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$ are joined in a ring structure that can include at least one heteroatom selected from N and O;

or R is —$CH_2$—$CH_2$—O—$CH_2$—$CH_2$—N($R_{10}$)($R_{11}$);

provided that $R_{14}$ is not H or OH;

reacting the compound of Formula X in the presence of an activator with a compound of Formula XI:

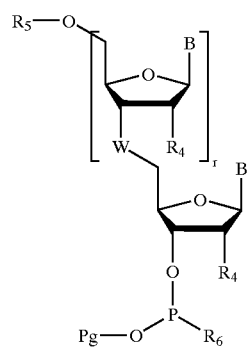

where r is 0 to about 50;
$R_8$ is a hydroxyl protecting group;
$R_6$ is —N($R_7$)$_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen; to form a compound of Formula XII:

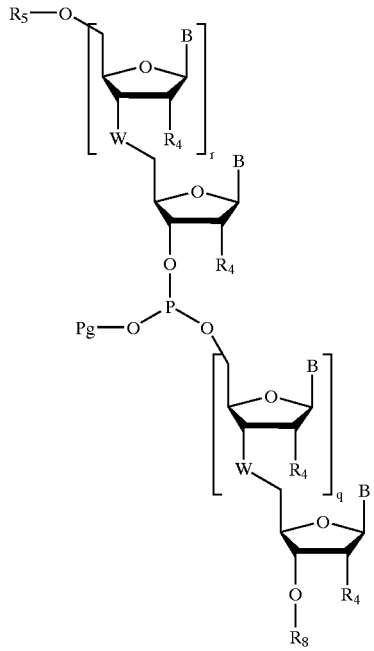

wherein the activator has the formula $G^+U^-$, where $G^+$ is selected from the group consisting of pyridinium, imidazolium, and benzimidazolium; and $U^-$ is selected from the group consisting of hexafluorophosphate, tetrafluoroborate, triflate, hydrochloride, trifluoroacetate, dichloroacetate, $^-$O-mesyl, $^-$O-tosyl, $^-$Br, and $^-$O-trifluorosulfonyl. Preferably, the activator is imidazolium triflate.

Some further preferred embodiments further comprise oxidizing or sulfurizing the compound of Formula XII to form a compound of Formula XIII:

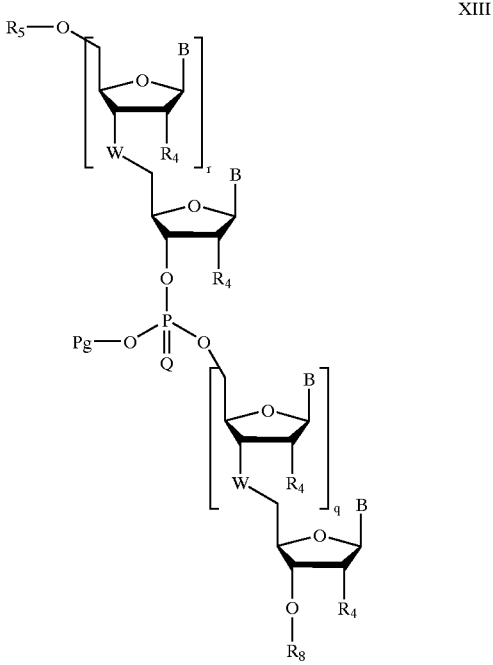

where Q is O or S.

Some further preferred embodiments of the methods further comprising a capping step, which is preferably performed prior to oxidation.

Some further preferred embodiments further comprising the step of cleaving the oligomeric compound to produce a further compound of formula X.

In a further aspect of the invention, synthetic methods are provided for the preparation of dimeric and higher order oligonucleotides having at least one bioreversible protecting group that confers enhanced chemical and biophysical properties. In some preferred embodiments, these methods comprise: providing a compound of Formula XX:

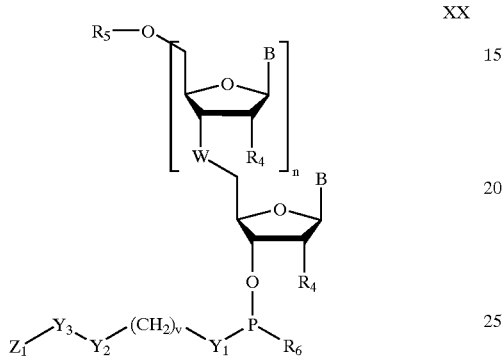

XX wherein:
$R_4$ is H, F, O—R, S—R or N—R($R_{10}$);
R is H, a protecting group, or has one of the formulas:

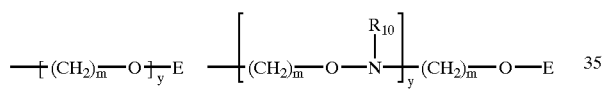

where
each m is independently from 1 to 10;
y is from 0 to 10;
E is H, a hydroxyl protecting group, $C_1$-$C_{10}$ alkyl, N($R_{10}$)($R_{11}$) or N=C($R_{10}$)($R_{11}$); substituted or unsubstituted $C_1$-$C_{10}$ alkyl, $C_2$-$C_{10}$ alkenyl, $C_2$-$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$-$C_{10}$ alkyl, $C_2$-$C_{10}$ alkenyl, $C_2$-$C_{10}$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$, are joined in a ring structure that can include at least one heteroatom selected from N and O;
or R is —$CH_2$—$CH_2$—O—$CH_2$—$CH_2$—N($R_{10}$)($R_{11}$);
$R_5$ is a hydroxyl protecting group;
$Z_1$ is aryl having 6 to about 14 carbon atoms or alkyl having from one to about six carbon atoms;
$Y_1$ is O or S;
$Y_2$ is O or S;
$Y_3$ is C(=O) or S;
v is 2 to about 4;
B is a nucleobase;

$R_6$ is —N($R_7$)$_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen;
reacting said compound of Formula XX with a compound of Formula XXI:

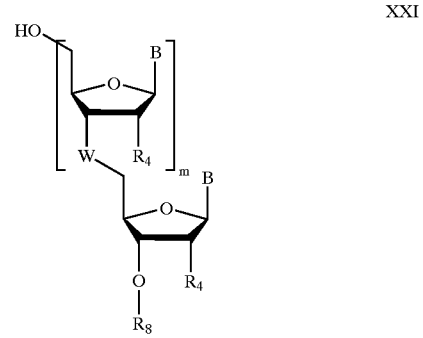

XXI wherein:
$R_8$ is H, a hydroxyl protecting group, or a linker connected to a solid support;
in the presence of an activator to form a compound of Formula XXII:

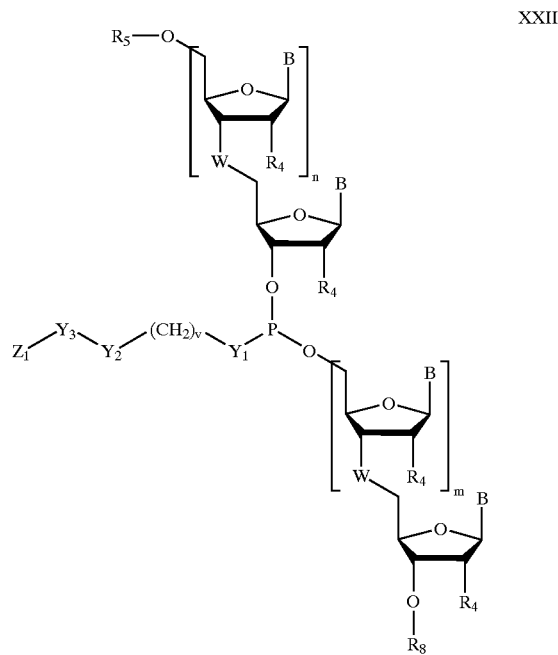

XXII wherein said activator has the formula $G^+U^-$, where $G^+$ is selected from the group consisting of pyridinium, imidazolium, and benzimidazolium; and $U^-$ is selected from the group consisting of hexafluorophosphate, tetrafluoroborate, triflate, hydrochloride, trifluoroacetate, dichloroacetate, $^-$O-MESYl, $^-$O-tosyl, $^-$Br, and $^-$O-trifluorosulfonyl. Preferably, the activator is an imidazolium triflate activator.

Some preferred embodiments of the foregoing methods further comprise oxidizing or sulfurizing the compounds of Formula XXII to form a compound of Formula XXIII:

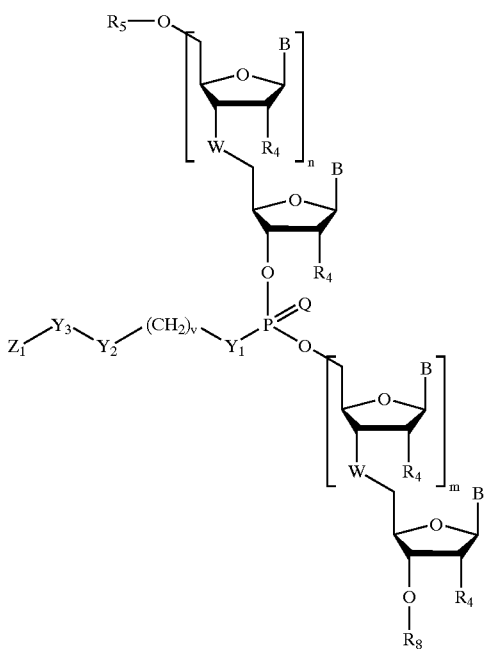

XXIII where Q is O or S.

Some further preferred embodiments of the methods further comprising a capping step, which is preferably performed prior to oxidation.

Some further preferred embodiments further comprising the step of cleaving the oligomeric compound to produce a further compound of formula XXI.

Methods for the preparation of compound XX can be found in copending application Ser. Nos. 09/066,638 and 09/095,822 filed Apr. 24, 1998 and Jun. 11, 1998, respectively, which are assigned to the assignee of the present application. The contents of the foregoing patent applications are hereby incorporated by reference in their entirety.

In further preferred embodiments, each of the foregoing methods, are performed iteratively to produce an oligonucleotide or analog thereof having a preselected nucleotide base sequence. In general, the phosphorus protecting groups, designated "Pg" in the formulas herein, are removed at the end of the synthetic regime, preferably at the time that the completed oligonucleotide or analog is cleaved form the solid support. However, in some preferred embodiments, the methods of the invention are beneficially employed to provide oligonucleotide analogs having at least one bioreversible protecting group that confers enhanced chemical and biophysical properties. See copending applications Ser. Nos. 09/066,638 and 09/095,822 filed Apr. 24, 1998 and Jun. 11, 1998, respectively. The bioreversible protecting groups further lend nuclease resistance to the oligonucleotides. The bioreversible protecting groups are removed in a cell, in the cell cytosol, or in vitro in cytosol extract, by endogenous enzymes. In certain preferred oligonucleotides of the invention the bioreversible protecting groups are designed for cleavage by carboxyesterases to yield unprotected oligonucleotides.

Preferably, the bioreversible protecting group has the Formula $Z_1-Y_3-Y_2-(CH_2)_v-Y_1-$, wherein the constituent variable are as defined above. In some preferred embodiments, $Y_1$ and $Y_2$ are each O, $Y_3$ is S, and Z is methyl or t-butyl, with t-butyl being preferred.

One particular advantage of the present invention is that the assembly of oligonucleotides and analogs thereof containing the bioreversible protecting group in accordance with the methods of the invention does not require protection for exocyclic nucleobase amino moieties, thus conferring significant benefit in expense, effort, and yield.

In preferred embodiments, the methods of the invention are used for the preparation of oligonucleotides and their analogs. As used herein, the term "oligonucleotide" is intended to include both naturally occurring and non-naturally occurring (i.e., "synthetic") oligonucleotides. Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in Antisense Research and Application, Ed. S. T. Crooke and B. Lebleu, CRC Press, 1993, in Englisch et al., Angewandte Chemie, International Edition, 1991, 30, 613–722 (see especially pages 622 and 623, and in the Concise Encyclopedia of Polymer Science and Engineering, J. I. Kroschwitz Ed., John Wiley & Sons, 1990, pages 858–859, Cook, Anti-Cancer Drug Design 1991, 6, 585–607, each of which are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2' sugar modifications (moiety $R_1$ in the formulas described herein) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)m, where m is 1 to about 10. Preferred among these polyethers are linear and cyclic polyethylene glycols (PEGs), and (PEG)-containing groups, such as crown ethers and those which are disclosed by Ouchi, et al., Drug Design and Discovery 1992, 9, 93, Ravasio, et al., J. Org. Chem. 1991, 56, 4329, and Delgardo et. al., Critical Reviews in Therapeutic Drug Carrier Systems 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, Sep. 16–20, 1992, hereby incorporated by reference in its entirety.

As used herein, the term "alkyl" includes but is. not limited to straight chain, branch chain, and alicyclic hydrocarbon groups. Alkyl -groups of the present invention may be substituted. Representative alkyl substituents are disclosed in U.S. Pat. No. 5,212,295, at column 12, lines 41–50, hereby incorporated by reference in its entirety.

"Aryl" groups are aromatic cyclic compounds including but not limited to phenyl, naphthyl, anthracyl, phenanthryl, pyrenyl, and xylyl.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention $R_8$ can be a linker connected to a solid support. Solid supports are substrates which are capable of serving as the solid phase in solid phase synthetic methodologies, such as those described in Caruthers U.S. Pat. Nos. 4,415,732; 4,458,066; 4,500, 707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1–23, hereby incorporated by reference in its entirety.

Preferred linkers for use in linking the growing oligonucleotide chain to the solid support in some preferred embodiments of the methods of the invention will be cleaved by reagents that do not result in removal of the $-Y_1-(CH_2)_q-Y_2-Y_2-Z$ protecting group. One such linker is the oxalyl linker (Alul, R. H., et al., *Nucl. Acids Res.* 1991, 19, 1527) between a LCAA-CPG solid support and the oligomer. Other photolabile supports have been reported (Holmes et al., *J. Org. Chem.* 1997, 62, 2370–2380; Greenberg et al., *Tetrahedron Lett.* 1993, 34, 251–254). The o-nitrobenzyl functionalized solid support has been previously reported (Dell'Aquila et al., *Tetrahedron Lett.* 1997, 38, 5289–5292). Another preferred method of cleavage without removal of internucleoside protecting groups is by irradiation with ultraviolet light in aqueous acetonitrile.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support, an aminopolyethyleneglycol derivatized support (see, e.g., Wright, et al., *Tetrahedron Letters* 1993, 34, 3373, hereby incorporated by reference in its entirety) and Poros, a copolymer of polystyrene/divinylbenzene.

In some preferred embodiments of the invention $R_5$ or $R_8$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups used for $R_5$ and $R_8$ include dimethoxytrityl (DMT), monomethoxytrityl, 9-phenylxanthen-9-yl (Pixyl) and 9-(p-methoxyphenyl)xanthen-9-yl (Mox). The $R_8$ or $R_8$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, et.al., *J. Chem. Soc.* 1990, 112, 1253–1254, and Iyer, et.al., *J. Org. Chem.* 1990, 55, 4693–4699); tetraethylthiuram disulfide (see e.g., Vu, et al., *Tetrahedron Lett.* 1991, 32, 3005–3008); dibenzoyl tetrasulfide (see e.g., Rao, et.al., *Tetrahedron Lett.* 1992, 33, 4839–4842); di(phenylacetyl)disulfide (see e.g., Kamer, *Tetrahedron Lett.* 1989, 30, 6757–6760); Bis(O,O-diisopropoxy phosphinothioyl)disulfide (see Stec et al., *Tetrahedron Lett.* 1993, 34, 5317–5320); 3-ethoxy-1,2,4-dithiazoline-5-one (see *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/ tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, et al., *Chem. Pharm. Bull.* 1987, 35, 833–836; Kumar, et al., *J. Org. Chem.* 1984, 49, 4905–4912; Bannwarth, *Helvetica Chimica Acta* 1985, 68, 1907–1913; Wolter, et al., *Nucleosides and Nucleotides* 1986, 5, 65–77, each of which are hereby incorporated by reference in their entirety.

The oligonucleotides produced by preferred embodiments of the methods of the invention having bioreversible protecting groups are also referred to in this specification as pro-oligonucleotides. Such pro-oligonucleotides are capable of improved cellular lipid bilayers penetrating potential as well as resistance to exo-and endonuclease degradation in vivo. In cells, the bioreversible protecting groups are removed in the cell cytosol by endogenous carboxyesterases to yield biologically active oligonucleotide compounds that are capable of hybridizing to and/or having an affinity for specific nucleic acid.

Additional advantages and novel features of this invention will become apparent to those skilled in the art upon examination of the examples thereof provided below, which should not be construed as limiting the appended claims.

PREPARATION OF PHOSPHORAMIDITES

EXAMPLE 1

General Phosphitylation Procedure using 2'-Deoxy-5'-O-DMT Nucleosides with Pyridinium Trifluoroacetate To a sample of 2'-deoxy-5'-O-DMT-nucleoside (2'-O-deoxy-5'-O-DMT-6-N-benzoyladenosine, 2'-O-deoxy-5'-O-DMT-4-N-benzoylcytidine, 2'-O-deoxy-5'-O-DMT-2-N-isobutyrylguanosine and 2'-O-deoxy-5'-O-DMT-thymidine) (1a–1d, FIG. 1, 10 mmol, 5.45–6.40 g) in dry dichloromethane (25 mL) was added bisamidite reagent (2-cyanoethyl-N,N,N',N'-tetraisopropylphosphorodiamidite, 5, FIG. 1, 3.81 mL, 3.62 g, 12 mmol) at ambient temperature under argon. Pyridinium trifluoroacetate (2.32 g, 12 mmol) was added and the reaction mixture was stirred at ambient temperature for 2–3 hours. The reaction was diluted with dichloromethane (35 mL), and washed with of saturated NaHCO$_3$/H$_2$O (30 mL). The organic layer was separated, dried (Na$_2$SO$_4$), evaporated, and purified on a short silica gel column. The amidite product was eluted with 60–80% EtOAc/hexanes (1% triethylamine) with the exact concentration dependent to the respective amidite being purified. The appropriate fractions were collected and evaporated to give the respective amidite product (6a–d, FIG. 1) as a white foam in ~80% yield.

EXAMPLE 2

General Phosphitylation Procedure Using 2'-O-Methyl-5'-O-DMT Nucleosides with Pyridinium Trifluoroacetate To a sample of 2'-O-methyl-5'-O-DMT-nucleoside (2'-O-methyl-5'-O-DMT-6-N-benzoyladenosine, 2'-O-methyl-5'-O-DMT-4-N-benzoylcytidine, 2'-O-methyl-5'-O-DMT-2-N-isobutyrylguanosine, 2'-O-methyl-5'-O-DMT-thymidine and 2'-O-methyl-5'-O-DMT-uridine) (2a–2e, FIG. 1, 1 mmol, 560–670 mg) in dry dichloromethane (3 mL) was added bisamidite reagent (0.38 mL, 362 mg, 1.2 mmol) at ambient temperature under argon. Pyridinium trifluoroacetate (232 mg, 1.2 mmol) was added to the reaction flask and the reaction mixture was stirred at ambient temperature for 2–3 hours. The reaction mixture was transferred directly to the top of a short silica gel column. The amidite product was eluted with 60–80% EtOAc/hexanes (1% triethylamine) with the exact concentration dependent to the respective amidite being purified. The appropriate fractions were collected and evaporated to give the respective amidite product (7a–e, FIG. 1) as a white foam in 75–94% yield.

EXAMPLE 3

General Phosphitylation Pocedure Using 2'-O-TBDMS-5'-O-DMT Nucleosides with Pyridinium Trifluoroacetate To a sample of 2'-O-TBDMS-5'-O-DMT-nucleoside (2'-O-TBDMS-5'-O-DMT-6-N-benzoyladenosine, 2'-O-TBDMS-5'-O-DMT-4-N-benzoylcytidine, 2'-O-TBDMS-5'-O-DMT-2-N-isobutyrylguanosine, 2'-O-TBDMS-5'$^{1-0}$-DMT-thymidine and 2'-O-TBDMS-5'-O-DMT-uridine) (3a–3e, FIG. 1, 1 mmol, 661–770 mg) in dry dichloromethane (3 mL) was added bisamidite reagent (0.38 mL, 362 mg, 1.2 mmol) at ambient temperature under argon. Pyridinium trifluoroacetate (232 mg, 1.2 mmol) was added to the reaction flask and the reaction mixture was stirred at ambient temperature for 2–3 hours. The reaction solution was transferred directly to the top of a short silica gel column. The amidite product was eluted with 45–60% EtOAc/hexanes (1% triethylamine) with the exact concentration dependent to the respective amidite being purified. The appropriate fractions were collected and evaporated to give the respective amidite product (8a–e, FIG. 1) as a white foam in 82–95% yield.

EXAMPLE 4

General Phosphitylation Procedure Using 2'-O-Methoxyethyl-5'-O-DMT Nucleosides with Pyridinium Trifluoroacetate To a sample of 2'-O-(2-methoxyethyl)-5'-O-DMT-nucleoside (2'-O-(2-methoxyethyl)-5'-O-DMT-6-N-benzoyladenosine, 2'-O-(2-methoxyethyl)-5'-O-DMT-4-N-benzoylcytidine, 2'-O-(2-methoxyethyl)-5'-O-DMT-2-N-isobutyrylguanosine, 2'-O-(2-methoxyethyl)-5'-O-DMT-thymidine, 2'-O-(2-methoxyethyl)-5'-O-DMT-uridine and 5-methyl-2'-O-(2-methoxyethyl)-5'-O-DMT-4-N-benzoylcytidine) (4a–f, FIG. 1, 1 mmol, 619–714 mg) in dry dichloromethane (3 mL) was added bisamidite reagent (0.38 mL, 362 mg, 1.2 mmol) at ambient temperature under argon. Pyridinium trifluoroacetate (232 mg, 1.2 mmol) was added to the reaction flask and the reaction mixture was stirred at ambient temperature for 2–3 h. The reaction solution was transferred directly to the top of a short silica gel column. The amidite product was eluted with 60–80% EtOAc/hexanes (1% triethylamine) with the exact concentration dependent to the respective amidite being purified. The appropriate fractions were collected and evaporated to give the respective amidite product (9a–f, FIG. 1) as a white foam in 92–95% yield.

EXAMPLE 5

General Procedure for Phosphitylation of Nucleoside 2'-Deoxy-5'-O-DMT-4-N-benzoylcytidine With Poly(4-vinyl Pyridine Hydrochloride) as an Activator Poly(4-vinyl pyridine hydrochloride) (Aldrich, 583 mg, ~6.5 mmol Cl/g) resin was washed with dry acetonitrile (10 mL×2). Dry dichloromethane (15 mL) and bisamidite reagent (1.20 mL, 1.14 g, 3.79 mmol) were added to the resin at ambient temperature under argon. Then a sample of 2'-deoxy-5'-O-DMT-4-N-benzoylcytidine (2.0 g, 3.16 mmol) was added and the reaction mixture was shaken by a mechanical shaker for 2 hours. The reaction was filtered and the filtrate was evaporated, and the residue was purified on a short silica gel column. The amidite product was eluted with 60% EtOAc/hexanes (1% triethylamine). The appropriate fractions were collected and evaporated to give amidite product (6b, FIG. 1) as a white foam (369 mg, 14%).

$^{31}$p NMR (CDCl$_3$) δ 149.34, 149.94.

EXAMPLE 6

General Procedure for Phosphitylation of the 5'-O-Position of 6-N-Benzoyl-2'-deoxy-3'-O-levulinyladenosine Using Pyridinium Trifluoroacetate A sample of 6-N-benzoyl-2'-deoxy-3'-O-levulinyl-adenosine (10, FIG. 1, 1 mmol, 453 mg) in dry dichloromethane (3 mL) was added bisamidite reagent (0.38 mL, 362 mg, 1.2 mmol) at ambient temperature under argon. Pyridinium trifluoroacetate (232 mg, 1.2 mmol) was added and the reaction mixture was stirred at ambient temperature for 2 hours. The reaction solution was transferred directly to the top of a short silica gel column. The amidite product was eluted with EtOAc (1% triethylamine). The appropriate fractions were collected and evaporated to give the amidite product (11, FIG. 1) as a white foam (601 mg, 92%).

$^{31}$p NMR (CDCl$_3$) δ 149.58.

EXAMPLE 7

Comparative Study of Activator Efficiency Using a) Pyridinium Acetate, b) Pyridinium Monochloroacetate, c) Pyridinium Dichloroacetate and d) Ppyridinium Trichloroacetate Four separate reactions were run to determine the efficience of selected pyridinium salts to act as an activator in phosphitylating 2'-deoxy-5'-O-DMT-4-N-benzoylcytidine. The activator species were produced in situ by addition of 1.2 eq. of the corresponding acetic acid, mono-, di- or trichloroacetic acid (0.56 mmol) to dry dichloromethane (1.5 mL) followed by addition of 1.3 eq. of pyridine (0.049 mL, 0.61 mmol). Bisamidite reagent (0.177 mL, 0.56 mmol) and 2'-deoxy-5'-O-DMT-4-N-benzoylcytidine (300 mg, 0.47 mmol) were added and the reaction mixtures were stirred under argon at ambient temperature. The progress of the reactions was monitored by TLC. There was no measurable reaction seen with the use of acetic acid and a slow reaction by use of either mono- or trichloroacetic acid (reaction not finished after 6.5 hours). At.6.5 hours the reaction was almost complete when dichloroacetic acid was used.

EXAMPLE 8

Phosphitylation Using Pyridinium Dichloroacetate, Synthesis of 21-Deoxy-5'-O-DMT-4-N-benzoylcytidine Diisopropylamino-cyanoethoxyphosphoramidite Pyridinium dichloroacetate was prepared in situ by addition of 1.3 equivalents of pyridine (0.49 mL, 6.07 mmol) to dry dichloromethane (4 mL) followed by addition of 1.2 eq. of dichloroacetic acid (0.46 mL, 5.60 mmol). To this mixture was added bisamidite reagent (1.78 mL, 5.60 mmol) followed by the dropwise addition of 2'-deoxy-5'-O-DMT-4-N-benzoylcytidine (2.97 g, 4.67 mmol) dissolved in dry dichloromethane (6 mL). The reaction mixture was stirred under argon at ambient temperature for 2 hours and transferred directly to the top of a short silica gel column. The amidite product was eluted with 70% EtOAc/hexanes (1% triethylamine). The appropriate fractions were collected and evaporated to give 3.47 g (89%) of the title compound as a white foam.

$^-$P NMR (CDCl$_3$) δ 149.29, 149.88.

EXAMPLE 9

Stability of 5'-O-DMT Protecting Group to Reaction Conditions, Synthesis of 2'-Deoxy-5'-O-DMT-4-N-benzoylcytidine Diisopropylaminocyanoethoxyphosphoramidite 4-N-Benzoyl-2'-deoxy-5'-O-DMT-cytidine (1.77 g, 2.79 mmol) was dissolved in dry dichloromethane (4 mL) under argon at ambient temperature followed by addition of bisamidite reagent (1.06 mL, 3.35 mmol) and pyridinium triflouroacetate (0.65 g, 3.35 mmol). The mixture was stirred under reflux for 5 hours with no measurable loss of DMT protecting group. Product formation was identified by tlc compared to a known solution of product.

EXAMPLE 10

Preparation of Amidites without Base Protection, Synthesis of 2'-Deoxy-5'-O-DMT-adenosine Diisopropylaminocyanoethoxy-phosphoramidite Pyridinium trifluoroacetate (353 mg, 1.83 mmol) was added to a mixture of 2'-deoxy-5'-O-DMT-adenosine (1 g, 841 mg, 1.52 mmol) and bisamidite reagent (0.53 mL, 505 mg, 1.67 mmol) in dichloromethane (5 mL). Stirring was continued for one hour at ambient temperature under argon atmosphere. The reaction solution was loaded without further workup on a silica gel column and eluted using a gradient of from 60 to 100% EtOAc/hexanes (1% triethylamine). The appropriate fractions were collected and evaporated to give 6.0 g of the title compound as a white foam (689 mg, 60%).

$^{31}$p NMR (CDCl$_3$) δ 149.26, 149.92.

EXAMPLE 11

Stability of Glycosidic Linkage to Reaction Conditions, Synthesis of 2'-Deoxy-5'-O-DMT-6-N-benzoyladenosine Diisopropylaminocyanoethoxyphosphoramidite 2'-deoxy-5'-O-DMT-6-N-benzoyladenosine Procedure (500 mg, 0.76 mmol) was dissolved in dry dichloromethane (1 mL) under argon at ambient temperature followed by addition of bisamidite reagent (0.266 mL, 252mg, 0.837 mmol) and pyridinium triflouroacetate (176 mg, 0.913 mmol). The mixture was stirred at ambient temperature for 2 hours, and then stirred under reflux for 1.5 hours with no measurable loss of the DMT protecting group or the adenine base. Product formation was identified by tlc compared to a known solution of product. This example shows the stability of the most labile glycosidic linkage of a nucleoside under the reaction conditions using this activator.

EXAMPLE 12

Mechanistic Study of Phosphitylation Using Pyridinium Trifluoroacetate

The mechanism of phosphitylation was investigated using the activator pyridinium trifluoroacetate and the nucleoside 5'-O-DMT-thymidine using a Varian 400 MHZ NMR. The first set of experiments were performed by studying the chemical shift of phosphorus nuclei under various conditions (Table 1). In a second set of experiments the chemical shift of nitrogen nuclei of various species were studied (Table 2).

The presence or absence of a specific phosphorus species was determined by recording $^{31}$p NMR of 5'-O-DMT-thymidine, bisamidite reagent and pyridinium trifluoroacetate in $CD_3CN$. The order of addition was altered in each individual experiment to determine which species is formed in the reaction mixture.

In experiment no. 1 (Table 1) the chemical shift of the $^{31}$p signal in bisamidite reagent (5) is measured to be at 125.8 ppm in $CD_3CN$. The activator pyridinium trifluoro-acetate (B) is then added to the solution of the solution of 5 and the $^{31}$p NMR was recorded. A new signal appeared at 158.8 ppm upon addition of B to 5, in addition to the original signal of 125.8 ppm. The peak at 158 is believed to be a protonated species of 5 which appears to be stable and formed quickly. Next, addition of 5'-O-DMT-thymidine (1d) to the mixture shifts the signals to 151.2 and 151.0 ppm, due to the formation of diastereoisomers.

In experiment no. 2 (Table 1) 5'-O-DMT-thymidine (1d) and bisamidite reagent (5) were taken together in $CD_3CN$ and the $^{31}$P NMR was recorded. It is noteworthy that 5 alone cannot react because the reagent is not activated or protonated. Thus, the chemical shift remains unchanged at 125.8 ppm. Addition of activator B to the mixture immediately forms the desired amidite 6d with $^{31}$p shifts of 151.2 and 151.0 ppm.

In another experiment, bisamidite reagent (5) was treated with an acid such as trifluoroacetic acid instead of activator B and the $^{31}$p NMR was recorded. First, the color of the reaction mixture changed from clear to dark and second there was no signal at 158 ppm for the protonated species.

TABLE 1

| compound | $^{31}$P NMR, chemical shift ppm (multiplicity) |
|---|---|
| Exp. No 1 | |
| 5 | 125.8 (s) |
| 5 + B | 158.8 (s) |
| | 125.8 (s) |
| 5 + B + 1d | 151.2, 151.0 (s + s) |
| Exp. No 2 | |
| 1d + 5 | 125.8 (s) |
| 1d + 5 + B | 151.2, 151.0 (s + s) |
| | 125.8 (s) |

Wherein
1d = 2'-O-deoxy-5'-O-DMT-thymidine
5 = 2-cyanoethyl-N,N,N',N'-tetraisopropylphosphorodiamidite
B = pyridinium trifluoroacetate The experimental data show that the protonation of the phosphitylating reagent is the first step during the reaction sequence and that the protonated form is stable. Support for this conclusion comes from the lack of signals seen for a second activated species that could form from nucleophilic attack by the counterion on the active species or alternatively reaction with free pyridine released during the protonation step. It is further seen that the use of trifluoroacetic acid alone results in degradation of the phosphitylating reagent. If an acid was all that was needed for activation of the phosphitylating reagent then the active phosphorous species should be formed anyway, with a possible following attack of the trifluoroacetate. These results demonstrate that the counterion does not participate in the mechanism. In other words the pyridinium ion acts as a proton donor and does not interact with the active phosphorus species further.

In experiment no. 3, (Table 2) $^{15}$N-labeled pyridine was used to further establish the role of the free pyridine formed during the activation of the phosphitylating reagent. It had previously been seen that a phosphorus species having pyridine acting to give nucleophilic assistance was not seen.

TABLE 2

| compound Exp. No 3 | $^{15}$NMR, chemical shift ppm |
|---|---|
| 12 | −69.0 |
| 12 + 13 | −148.0 |
| 5 + 12 + 13 | −68.5 |
| 1d + 5 + 12 + 13 | −71.74 |

Wherein
1d = 2'-O-deoxy-5'-O-DMT-thymidine
5 = 2-cyanoethyl-N,N,N',N'-tetraisopropylphosphorodiamidite
12 = pyridine
13 = trifluoroacetic acid The $^{15}$N-labeled pyridine alone gives a signal at −69.0 ppm. The in situ formation of the activator is performed by addition of the trifluoroacetic acid. A signal is seen for the activator (pyridinium trifluoroacetate) at —148.0 ppm. Next, addition of the bisamidite reagent (5) causes the signal of the pyridine to revert back to that of free pyridine as expected. Again, addition of 2'-O-deoxy-5'-O-DMT-thymidine (1d) which underwent phosphitylation did not change the free pyridine signal. In conclusion, pyridine reacts with the trifluoroacetic acid to form activator (B) that reacts with 5 to produce activated phosphitylating reagent. At this point the pyridine reverts back to free pyridine where it remains unchanged for the remainder of the phosphitylation reaction. The slight change in chemical shift (Table 2) after the addition of the other reagents is due to the extreme sensitivity of the nitrogen signal to the concentration.

EXAMPLE 13

Determination of Efficiency of Selected Activators

Figure 2:
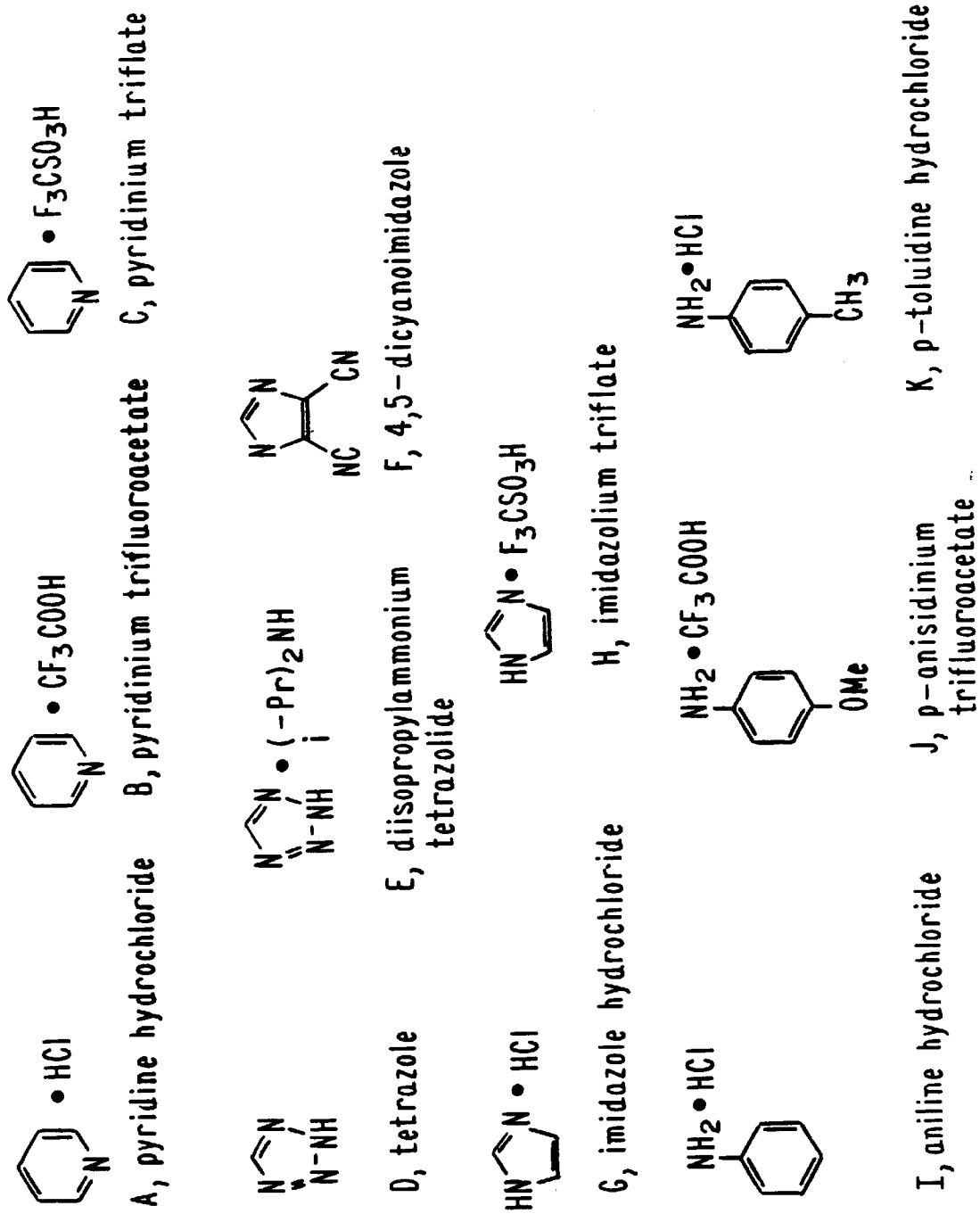
FIG. 2 is a list of activating reagents suitable for use in the present invention.
Figure 3:
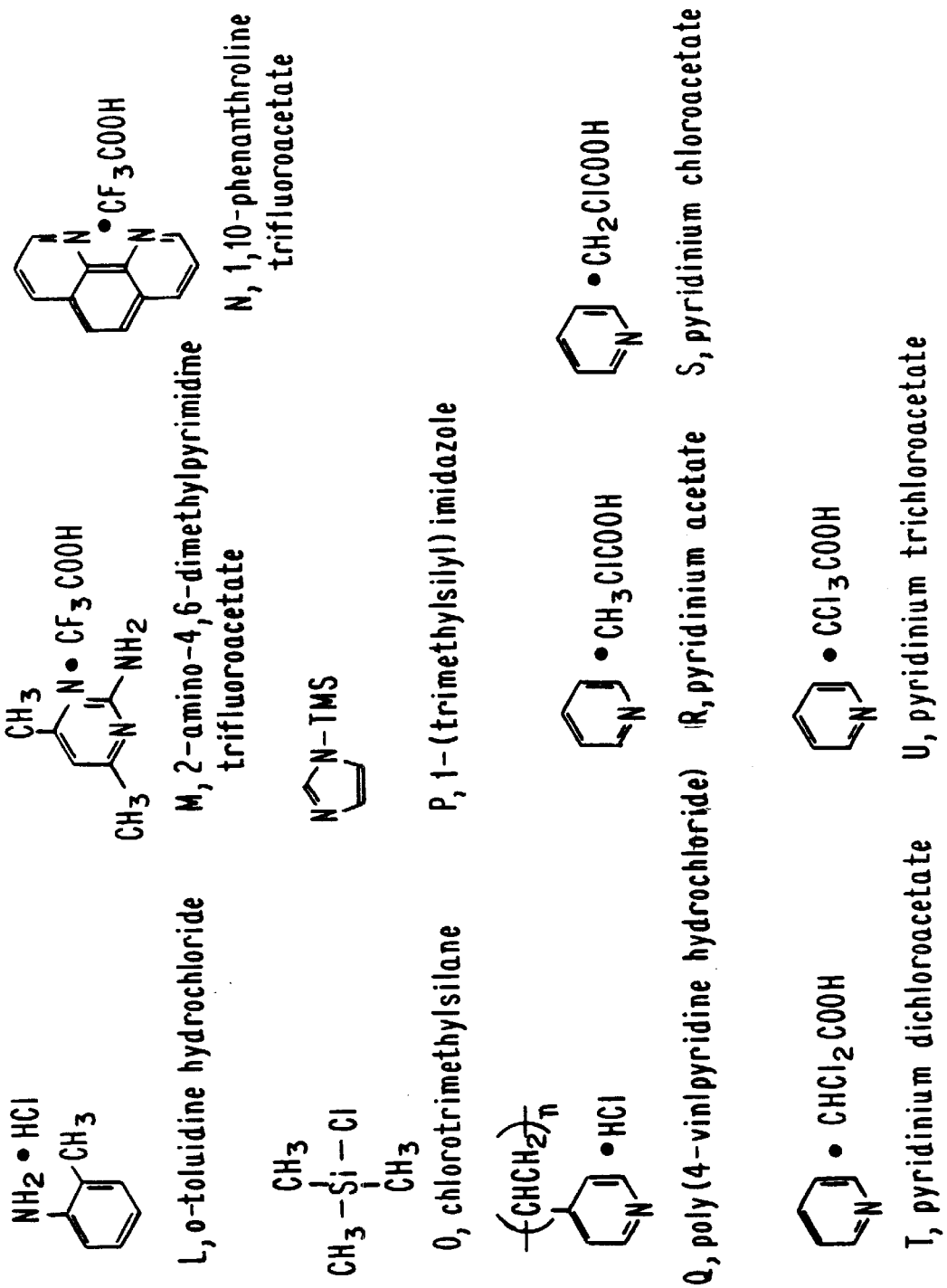
FIG. 3 is a list of activating reagents suitable for use in the present invention.
Figure 4A:
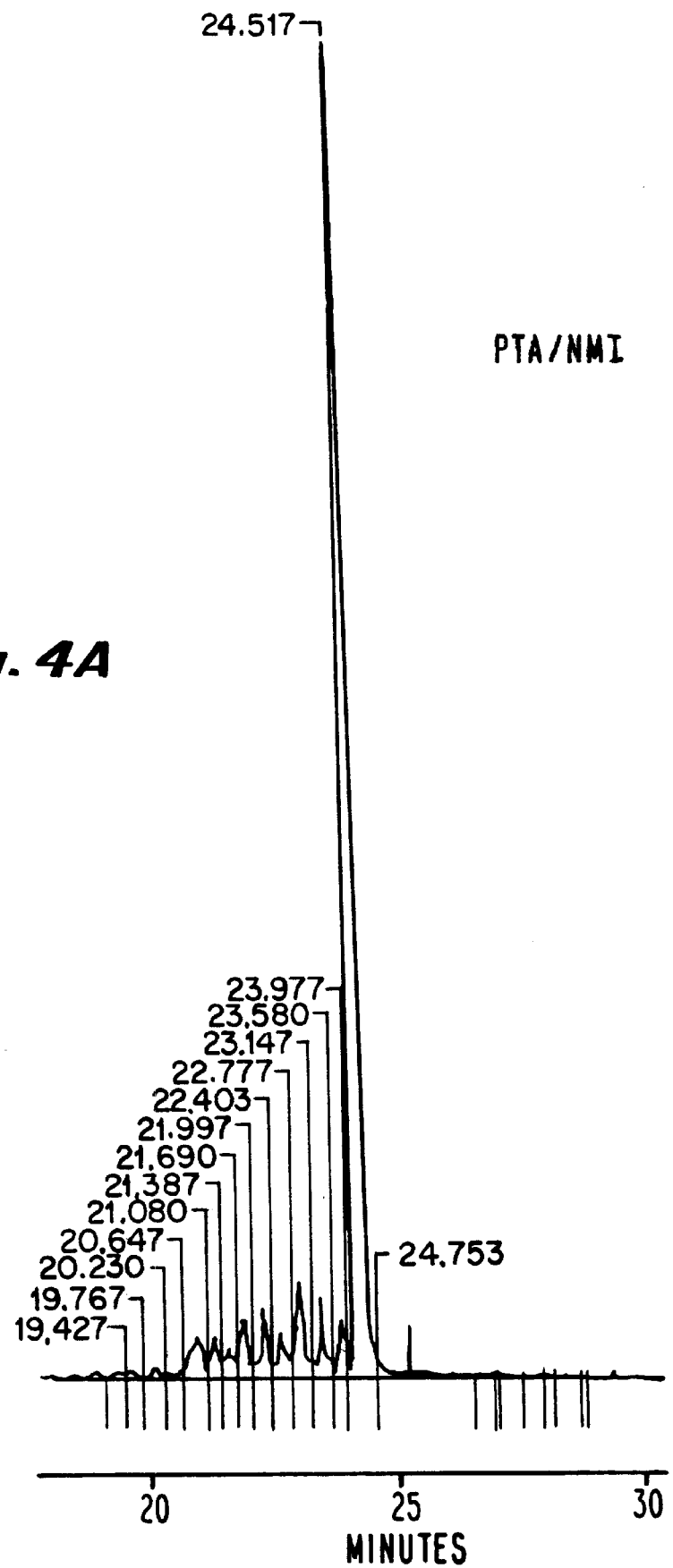
FIG. 4 is an electropherogram comparing the efficiency of tetrazole activator and pyridinium trifluoroacetate/1-methylimidazole activator.
Figure 4B:
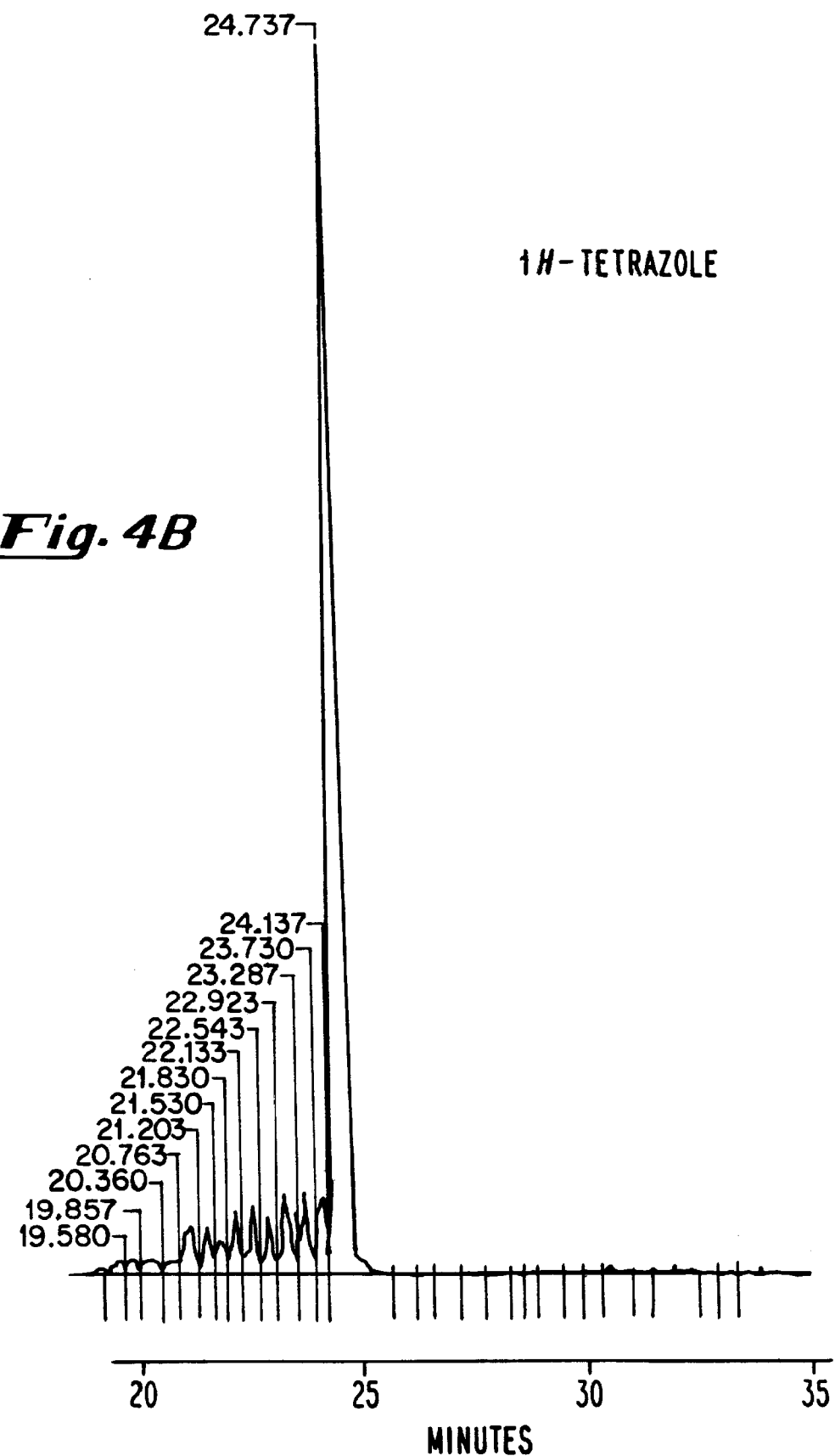

In order to determine the efficiency of activators under a variety of conditions 55 experiments were performed using a wide range of different activators (see FIGS. 2 and 3). A variety of nucleosides were employed including 2'-deoxy and 2'-O-modified nucleosides (see FIG. 1). Different solvents were also employed including a dichloromethane, acetonitrile, ethyl acetate and toluene to evaluate the rate of reaction.

TABLE 3

| Cmpd. I | Act. II | Ratio (I:P[III]:II) | Sol. | Time hrs. | Yld. (%) | $^{31}$P NMR |
|---|---|---|---|---|---|---|
| 1a | A | 1:1.4:1.4 | DCM | 3 | 72 | 149.32, 149.43 |
| 1a | H | 1:1.2:1.2 | DCM | 3 | 54 | 149.32, 149.43 |
| 1a | F | 1:1.2:1.2 | ACN | 2 | 51 | 149.32, 149.43 |
| 1a | F | 1:0.7:1.2 | ACN | 4.5 | 52 | 149.32, 149.43 |
| 1a | C | 1:1.2:1 | ACN | 2 | 42 | 149.32, 149.A3 |
| 1a | B | 1:1.2:1.2 | ACN | 2 | 90 | 149.32, 149.43 |
| 1a | B | 1:1.2:1.2 | DCM | 2 | 68 | 149.32, 149.43 |
| 1a | I | 1:1.2:1.2 | ACN | 48 | — | N/A |
| 1a | I | 1:1.2:1.2 | DCM | 48 | — | N/A |
| 1a | J | 1:1.2:1.2 | DCM | 48 | — | N/A |
| 1a | K | 1:1.2:1.2 | DCM | 17.5 | — | N/A |
| 1a | L | 1:1.2:1.2 | ACN | 17.5 | — | N/A |

TABLE 3-continued

| Cmpd. I | Act. II | Ratio (I:P[III]:II) | Sol. | Time hrs. | Yld. (%) | $^{31}$P NMR |
|---|---|---|---|---|---|---|
| 1a | M | 1:1.2:1.2 | DCM | 0.25 | 71 | 149.32, 149.43 |
| 1a | N | 1:1.2:1.2 | DCM | 3 | 35 | 149.32, 149.43 |
| 1a | N | 1:1.2:1.2 | DCM | 20 | 32 | 149.32, 149.43 |
| 1b | A | 1:1.2:1.2 | DCM | 4 | 87 | 149.29, 149.88 |
| 1b | B | 1:1.2:1.2 | ACN | 5 | 74 | 149.29, 149.88 |
| 1b | A | 1:1.2:1.2 | ACN | 5 | 60 | 149.29, 149.88 |
| 1b | G | 1:1.2:1.2 | ACN | 24 | 44 | 149.29, 149.88 |
| 1b | B | 1:1.2:1.2 | EtOAc | 6 | 73 | 149.29, 149.88 |
| 1b | B* | 1:1.2:1.2 | EtOAc | 7 | 50 | 149.29, 149.88 |
| 1b | B | 1:1.2:1.2 | DCM | 1 | 93 | 149.29, 149.88 |
| 1c | A | 1:1.2:1.2 | DCM | 3 | 89 | 148.39, 149.15 |
| 1c | A | 1:1.2:1.2 | ACN | 20 | — | N/A |
| 1c | A | 1:1.2:1.2 | tol | 20 | — | N/A |
| 1c | B | 1:1.2:1.2 | ACN | 20 | 80 | 148.39, 149.15 |
| 1c | B | 1:1.2:1.2 | EtOAc | 3 | 66 | 148.39, 149.15 |
| 1c | B | 1:1.2:1.2 | DCM | 3 | 74 | 148.39, 149.15 |
| 1d | D | 1:2.0:1 | DCM | 2 | 70 | 149.14, 149.57 |
| 1d | E | 1:1.4:0.3 | DCM | 2 | 86 | 149.14, 149.57 |
| 1d | D | 1:1.1:1 | DCM | 3 | 94 | 149.14, 149.57 |
| 1d | O | 1:1.2:0.6 | DCM | 3 | 41 | 149.14, 149.57 |
| 1d | A | 1:1.2:1.2 | DCM | 3 | 86 | 149.14, 149.57 |
| 1d | B | 1:1.2:1.2 | DCM | 3 | 88 | 149.14, 149.57 |
| 1d | C | 1:1.2:1 | DCM | 3 | 78 | 149.14, 149.57 |
| 1d | C | 1:1.2:1.2 | DCM | 3 | 87 | 149.14, 149.57 |
| 1d | P | 1:1.2:1.2 | DCM | 3 | si. | N/A |
| 2a | B | 1:1.2:1.1 | DCM | 0.75 | 75 | 150.94, 151.67 |
| 3a | B | 1:1.2:1.1 | DCM | 0.75 | 95 | 150.60, 151.05 |
| 4a | B | 1:1.2:1.1 | DCM | 0.8 | 96 | 149.66, 151.59 |
| 2b | B | 1:1.2:1.2 | DCM | 2 | 94 | 150.77, 151.35 |
| 3b | B | 1:1.2:1.2 | DCM | 2 | 90 | 149.85, 150.72 |
| 4f | B | 1:1.2:1.2 | DCM | 2 | 92 | 150.76, 150.82 |
| 2c | B | 1:1.2:1.2 | DCM | 2 | 86 | 150.71, 150.95 |
| 3c | B | 1:1.2:1.2 | DCM | 2 | 82 | 149.43, 150.37 |
| 4c | B | 1:1.2:1.2 | DCM | 2 | 94 | 150.23, 150.82 |
| 2e | B | 1:1.2:1.2 | DCM | 2 | 88 | 150.86, 151.39 |
| 3e | B | 1:1.2:1.2 | DCM | 2 | 84 | 150.22, 150.61 |
| 4d | B | 1:1.2:1.2 | DCM | 3 | 95 | 150.69, 150.83 |
| 1f | B | 1:1.2:1.2 | DCM | 2 | 91 | 149.14, 149.67 |
| 1o | Q | 1:1.2:1.2 | DCM | 2 | 14 | 149.34, 149.94 |
| 1b | R* | 1:1.2:1.2 | DCM | 2 | — | N/A |
| 1b | S* | 1:1.2:1.2 | DCM | 2 | sl. | N/A |
| 1b | T* | 1:1.2:1.2 | DCM | 2 | 89 | 149.29, 149.88 |
| 1b | U* | 1:1.2:1.2 | DCM | 2 | sl. | N/A |
| 1g | B | 1:1.1:1.2 | DCM | 1 | 60 | 149.26, 149.92 |

Note:
I = compound (nucleoside)
II = activator (Act.)
P[III] = phosphitylating agent (bisamidite reagent)
— = no reaction
* = in situ
si. = silyation
sl. = slow reaction
Cmpd. = compound, see FIG. 1
Act. = activator
Sol. = solvent
DCM = dichloromethane
ACN = acetonitrile
EtOAc = ethyl acetate
tol = toluene Activators A=pyridine hydrochloride
B=Pyridinium trifluoroacetate
C=Pyridinium triflate
D=tetrazole
E=diisopropylammonium tetrazolide
F=4,5-dicyanoimidazole
G=imidazole hydrochloride
H=imidazolium triflate
I=aniline hydrochloride
J=p-anisidinium trifluoroacetate
K=p-toluidine hydrochloride
L=o-toluidine hydrochloride
M=2-amino-4,6-dimethylpyrimidine trifluoroacetate
N=1,10-phenanthroline trifluoroacetate
O=chlorotrimethylsilane (TMSCl)
P=1-(trimethylsilyl)imidazole
Q=poly(4-vinylpyridine hydrochloride)
R=pyridinium acetate
S=pyridinium chloroacetate
T=pyridinium dichloroacetate
U=pyridinium trichloroacetate Preparation of Intersugar Linkages Using Pyridinium Salt/Substituted Imidazole Actoivators

EXAMPLE 14

Synthesis of T-T Phosphorothioate Dimer 100 milligram (4 mmole) of 5'-O-Dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with dichloromethane and then with acetonitrile. Then, a 0.2 M solution of 5'-O-(4,4'-dimethoxytrityl)thymidine-3'-O-(2-cyanoethyl)-N,N-diisopropylphosphoramidite) in acetonitrile and a 0.22 M solution of pyridinium trifluoroacetate and 0.11M solution of 1-methylimidazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

The carrier containing the compound was treated with 30% aqueous ammonium hydroxide solution for 90 minutes. The aqueous solution was filtered, concentrated under reduced pressure to give phosphorothioate dimer of T-T.

EXAMPLE 15

Synthesis of C-T Phosphorothioate Dimer 100 milligram (4 mmole) of 5'-O-Dimethoxytritylthymidine bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of $N^4$-Benzoyl-5'-O-(4,4'-dimethoxytrityl)-2'-deoxycytidine-3'-O-(2-cyanoethyl)-N,N-diisopropylphosphoramidite) in acetonitrile and a 0.22 M solution of pyridinium trifluoroacetate and 0.11 M solution of 1-methylimidazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

The carrier containing the compound was treated with 30% aqueous ammonium hydroxide solution for 90 minutes and then incubated at 55° C. for 12 hours. The aqueous solution was filtered, concentrated under reduced pressure and then treated at room temperature with 1.0 M solution of tetra-n-butyl ammonium fluoride in THF to give a phosphorothioate dimer of dC-T.

EXAMPLE 16

Synthesis of 5'-TTTTTTT-3' Phosphorothioate Heptamer 50 milligram (2 mmole) of 5'-O-dimethoxytritylthymidine bound to CPG (controlled pore glass) through an ester linkage was taken up in a glass reactor, and a toluene solution of 3% dichloroacetic acid (volume/volume) was added to deprotect the 5'-hydroxyl group. The product was washed with acetonitrile. Then, a 0.2 M solution of 5'-O-(4,4'-dimethoxytrityl)thymidine-3'-O-(2-cyanoethyl N,N-diisopropylphosphoramidite) in acetonitrile and a 0.22 M solution of pyridinium trifluoroacetate and 0.11 M solution of 1-methylimidazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile, and then a solution of acetic anhydride/lutidine/THF (1:1:8), and N-methyl imidazole/THF was added to cap any unreacted 5'-hydroxyl group. The product was washed with acetonitrile.

This complete cycle was repeated five more times to produce the completely protected thymidine heptamer. The carrier containing the compound was treated with 30% aqueous ammonium hydroxide solution for 90 minutes at room temperature. The aqueous solution was filtered, and concentrated under reduced pressure to give a phosphorothioate heptamer, TTTTTTT.

EXAMPLE 17

Synthesis of 5'-d(GACT)-3' Phosphorothioate Tetramer 50 milligram (2 mmole) of 5'-O-dimethoxytritylthymidine bound to CPG (controlled pore glass) through an ester linkage was taken up in a glass reactor, and a toluene solution of 3% dichloroacetic acid in toluene (volume/volume) was added to deprotect the 5'-hydroxyl group. The product was washed with acetonitrile. Then, a 0.2 M solution of 5'-O-(4,4'-dimethoxytrityl) thymidine-3'-O-(2-cyanoethyl N,N-diisopropylphosphoramidite) in acetonitrile and a 0.22 M solution of pyridinium trifluoroacetate and 0.11 M solution of 1-methylimidazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

A solution of 3% dichloroacetic acid in toluene (volume/volume) was added to deprotect the 5'-hydroxyl group. The product was washed with acetonitrile. Then, a 0.2 M solution of $N^4$-benzoyl-5'-O-(4,4'-dimethoxytrityl)-2'-deoxycytidine-3'-O-(2-cyanoethyl N,N-diisopropylphosphoramidite) in acetonitrile and a 0.22 M solution of pyridinium trifluoroacetate and 0.11 M solution of 1-methylimidazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap any unreacted 5'-hydroxyl group. The product was washed with acetonitrile.

A solution of 3% dichloroacetic acid in toluene (volume/volume) was added to deprotect the 5'-hydroxyl group. The product was washed with acetonitrile. Then, a 0.2 M solution of $N^6$-benzoyl-5'-O-(4,4'-dimethoxytrityl)-2'-deoxyadenosine-3'-O-(2-cyanoethyl N,N-diisopropylphosphoramidite) in anhydrous acetonitrile and a 0.22 M solution of pyridinium trifluoroacetate and 0.11 M solution of 1-methylimidazole in acetonitrile was added, and allowed to react at room temperature for 5 minutes. The product was washed with acetonitrile, and then a 0.2 M solution of phenylacetyl disulfide in acetonitrile: 3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

A solution of 3% dichloroacetic acid in toluene (volume/volume) was added to deprotect the 5'-hydroxyl group. The product was washed with acetonitrile. Then, a 0.2 M solution of $N^2$-isobutyryl-5'-O-(4,4'-dimethoxytrityl)-2'-deoxyguanosine-3'-O-(2-cyanoethyl N,N-diisopropylphosphoramidite) in acetonitrile and a 0.22 M solution of pyridinium trifluoroacetate and 0.11 M solution of 1-methylimidazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap any unreacted 5'-hydroxyl group. The product was washed with acetonitrile.

The carrier containing the compound was treated with 30% aqueous ammonium hydroxide solution for 90 minutes at room temperature and then incubated at 55° C. for 24 hour. The aqueous solution was filtered, concentrated under reduced pressure to give a phosphorothioate tetramer of 5'-dG-dA-dC-T-3'.

EXAMPLE 18

Synthesis of Fully-modified 5'-d(TCC-CGC-CTG-TGA-CAT-GCA-TT)-3' Phosphorothioate 20-mer (SEQ ID NO:1)

The synthesis of the above sequence was performed on a Pharmacia OligoPilot II Synthesizer on a 180 mmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

EXAMPLE 19

Synthesis of Fully-modified 5'-d(GCC-CAA-GCT-GGC-ATC-CGT-CA)-3' Phosphorothioate 20-mer (SEQ ID NO:2)

The synthesis of the above sequence was performed on a Pharmacia OligoPilot II Synthesizer on a 180 μmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulftrization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

EXAMPLE 20

Synthesis of Fully-modified 5'-d(GCG-TTT-GCT-CTT-CTT-CTT-GCG)-3' Phosphorothioate 21-mer (SEQ ID NO:3)

The synthesis of the above sequence was performed on a Pharmacia OligoPilot II Synthesizer on a 180 μmole scale using the cyanoethyl phosphoramidites and Pharmacia s primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

EXAMPLE 21

Synthesis of Fully-modified 5'-d(GTT-CTC-GCT-GGT-GAG-TTT-CA)-3' Phosphorothioate 20-mer (SEQ ID NO:4)

The synthesis of the above sequence was performed on a Pharmacia OligoPilot II Synthesizer on a 180 μmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

EXAMPLE 22

Synthesis of Fully-modified 5'-d(TCC-GTC-ATC-GCT-CCT-CAG-GG)-3' Phosphorothioate 20-mer (SEQ ID NO:5)

The synthesis of the above sequence was performed on a Pharmacia OligoPilot II Synthesizer on a 180 μmole scale using the cyanoethyl phosphoramidites and Pharmacia's primar support. Detritylation was performed using 3% dichloroacetic acid in toluene (volume/volume). Activation of phosphoramidites was done with a 0.22 M solution of performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

EXAMPLE 23

Synthesis of Fully-modified 5'-d(TCC-CGC-CTG-TGA)-2'-methoxyethyl-(CAT-GCA-TT)-3' Phosphorothioate 20-mer (SEQ ID NO:6)

The synthesis of the above sequence was performed on a Milligen 8800 Synthesizer on a 282 mmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified in the usual manner.

EXAMPLE 24

Synthesis of Fully-modified 5'-d(TCC-CGC-CTG-TGA)-2'-methoxyethyl-(CAT-GCA-TT)-3' Phosphorothioate 20-mer (SEQ ID NO:7)

The synthesis of the above sequence was performed on a Pharmacia OligoPilot II Synthesizer on a 250 mmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified in the usual manner

EXAMPLE 25

Synthesis of Fully-modified 5'-d(GC$^{me}$C$^{me}$-C$^{me}$AA-GC$^{me}$T-GGC$^{me}$)-2'-Methoxyethyl-(AU$^{me}$C$^{me}$-C$^{me}$GU$^{me}$-C$^{me}$A)-3' phosphorothioate 20-mer (SEQ ID NO:8)

The synthesis of the above sequence was performed on a OligoPilot II on a 200 mmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 3 minutes. At the end of synthesis, the support was washed with acetonitrile, cleaved, deprotected and purified in the usual manner.

EXAMPLE 26

Synthesis of Fully-modified 5'-d(TGG-TGG_TGG_TGG_TGG_TGG-T)-3' Phosphorothioate 20-mer (SEQ ID NO:9)

In order to compare the extent of formation of (n+1)-mers during the oligonucleotide synthesis between the two activators, the following experiment was conducted:

The synthesis of the above sequence was performed on a OligoPilot I on a 30 mmole scale using the cyanoethyl phosphoramidites and Pharmacia's primar support. Detritylation was performed using 3% dichloroacetic acid in toluene (volume/volume). Activation of phosphoramidites was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 3 minutes. At the end of synthesis, the support was washed with acetonitrile, cleaved, deprotected and purified in the usual manner.

The above synthesis was repeated with 0.45 M solution of 1H-tetrazole. At the end of synthesis, the support was washed with acetonitrile, cleaved, deprotected and purified in the usual manner.

The oligonucleotides were analyzed by capillary gel electrophoresis. A comparison of the two electropherograms shows that the two activators perform at the same efficiency.

Preparation of Internucleotide Linkages Between 2'-Substituted Nucleosides Using Imidazolium Triflate Activator

EXAMPLE 27

Synthesis of Pyridinium Tetrafluoborate, Pyrinium Hexafluoro Phosphate, Imidazolium Salt and Benzimidazolium Salt Pyridinium tetrafluoborate is prepared according to the procedure described by Brill et al., *J. Am. Chem. Soc.*, 1991 113, 3972.

Pyridinium tetrafluoborate is ion-exchanged with sodium hexafluorophosphate to give pyridinium hexafluorophosphate.

Imidazolium triflate is prepared according to the procedure of Kataoka et al., Nucleic *Acids Symposium Series*, 1998, 37, 21–22).

Benzimidazolium triflate is synthesized according to the reported procedure of Hayakawa et al.,. *Org. Chem.*, 1996, 61, 7996–7997.

EXAMPLE 28

Synthesis of Benzimidazolium Tetrafluoroborate

To a solution of benzimidazole (10 g, 84.6 mmol) in dichloromethane (30 mL) is added dropwise tetrafluoroboric acid as its etherate (85%, $HBF_4$ by volume, Aldrich Chemicals Co.) with stirring at 0C. The reaction mixture is diluted with diethylether (100 mL) to precipitate the title compound. The title compound is filtered, washed with ether and recrystallized from ether.

EXAMPLE 29

Synthesis of Imidazolium Tetrafluoroborate

To a solution of imidazole (20 mmol) in dichloromethane (30 mL) at 0° C. $HBF_4$ (20 mmol, 3.8g of a diethyl etherate) in dichloromethane is added dropwise. The reaction mixture is diluted with diethyl ether (100 mL) to precipitate the title compound. It is then filtered, washed with ether and recrystallized from ether.

EXAMPLE 30

Synthesis of Imidasolium Hexafluorophosphate

Hexafluorophosphoric acid (65% in water) is purchased from Fluka and evaporated with pyridine three times to concentrate. A solution of imidazole or benzimidazole (20 mmol) in ether (100 mL) is treated with 20 mmol of evaporated hexafluorophosphoric acid under stirring and at 0° C. After mixing the solution is evaporated and the slurry is treated with anhydrous ether. The salt is isolated by filtration, followed by washing with ether and drying in vacuo.

EXAMPLE 31

Synthesis of Nucleobase-protected Amidite Monomer Units Derived from 2'-MOE Nucleoside Precursors Using Imidazolium Salts The nucleosidic monomers having 2'-O-(methoxyethyl) modification are treated with 2-cyanoethyl-N,N,N',N'-tetraisopropyl phosphorodiamidite (1.2 equivalents) and imidazolium salt or benzimidazolium salt (0.5 equivalent) in dry methylenechloride at ambient temperature for about 30–60 minutes. Reaction progress and formation of the respective amidite is monitored by tlc. This general procedure is used to convert selected 2'-O-methoxyethoxy (2'-O-MOE) proctected nucleosides into the respective phosphoramidites. One equivalent of selected nucleosides 2'-O-(MOE)-5'-O-DMT-6-N-benzoyladenosine, 2'-O-(MOE)-5'-O-DMT-4-N-benzoylcytidine, 2'-O-(MOE)-5'-O-DMT-N-2-isobutyryl-guanosine, 2'-O-(MOE)-5'-O-DMT-5-methyluridine, 2'-O-(MOE)-5'-O-DMT-uridine, 2'-O-(MOE)-5'-O-DMT-5-methyl-4-N-benzoylcytidine in anhydrous dichloromethane is treated with 2-cyanoethyl-N,N,N',N'-tetraisopropyl phosphorodiamidite (1.2 equivalents) and either imidazolium salt or benzimidazolium salt (0.5 equivalent) at ambient temperature for 30–60 minutes under argon. The reaction mixture is directly loaded onto a silica gel column and the product eluted with a gradient of ethylacetate/hexane. Desired product for each respective amidite is identified by tlc and collected and concentrated. Purity is determined by 1H and $^{31}P$ NMR studies.

EXAMPLE 32

Synthesis of Nucleobase-unprotected Amidite Monomers Derived from 2'-MOE Nucleoside Precursors Using Imidazolium Salts The nucleoside monomers without the protecting group for exocyclic amines are synthesized in a similar manner to the previous example. 2'-O-(MOE)-5'-O-DMT adenosine, 2'-O-(MOE)-5'-O-DMT-cytidine, 2'-O-(MOE)-5'-O-guanosine, 2'-O-(MOE)-5'-O-DMT-5-methyluridine, 2'-O-(MOE)-5'-O-DMT-uridine, 2'-O-(MOE)-5'-O-DMT-2-aminoadenosine, 2'-O-(MOE)-5'-O-DMT-5-methylcytidine, in each case 1 equivalent, is taken in anhydrous methylenechloride/DMF mixture and treated with 2-cyanoethyl-N,N,N',N'-tetraisopropyl phosphorodiamidite (1.5 equivalents) and one of the imidazolium salts or benzimidazolium salts (0.5 equivalents) at ambient temperature for 30–60 mins under argon. The reaction mixture is evaporated, toluene is added and reevaporated and the residue is dissolved in anhydrous methylenechloride and eluted with ethylacetate solvent. The phosphoramidite products are pooled and characterized by $^{31}p$ NMR.

EXAMPLE 33

Synthesis of Fully-modified 5'-d(TCC-CGC-CTG-TGA-CAT-GCA-TT)-3' Phosphorothioate 20-mer (SEQ ID NO:10)

The synthesis of the above sequence is performed on an Expedite (Millipore) Synthesizer on a 1 micromole scale using 2-cyanoethyl phosphoramidites and CPG support. Detritylation is performed using 3% dichloroacetic acid in methylene chloride. Activation of phosphoramidites is done with a 0.22 M solution of pyridinium tetrafluoroborate and 0.1 1 M solution of 1-methylimidazole. Sulfurization is performed using Beaucage reagent. At the end of synthesis, the support is washed with acetonitrile, cleaved, deprotected and purified in the usual manner.

EXAMPLE 34

Synthesis of Fully-modified 5'-d(GCC-CAA-GCT-GGC-ATC-CGT-CA)-3' Phosphorothioate 20-mer (SEQ ID NO:11)

The above sequence is prepared using an Expedite (Millipore) Synthesizer on a 1 micromole scale using 2-cyanoethyl phosphoramidites and CPG support. Detritylation is performed using 3% dichloroacetic acid in methylene chloride. Phosphoramidites are activated with a 0.22 M solution of pyridinium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 35

Synthesis of Fully-modified 5'-d(GCG-TTT-GCT-CTT-CTT-CTT-GCG)-3' Phosphorothioate 21-mer (SEQ ID NO:12)

The above sequence is prepared on an Expedite (Millipore) Synthesizer on a 1 micromole scale using the 2-cyanoethyl phosphoramidites and CPG support. Detritylation is performed using 3% dichloroacetic acid in methylene chloride. Phosphoramidites are activated with a 0.22 M solution of pyridinium tetrafluoroborate and 0.11 M solution of 1-methylimidazole. Sulfurization is performed using Beaucage reagent. After synthesis, the support is washed with acetonitrile, cleaved, deprotected and purified in the usual manner.

EXAMPLE 36

Synthesis of Fully-modified 5'-d(GTT-CTC-GCT-GGT-GAG-TTT-CA)-3' Phosphorothioate 20-mer (SEQ ID NO:13)

The above sequence is prepared on an Expedite (Millipore) Synthesizer on a 1 micromole scale using the 2-cyanoethyl phosphoramidites and CPG support. Detritylation is performed using 3% dichloroacetic acid in methylene chloride. Phosphoramidited are activated with a 0.22 M solution of pyridinium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 37

Synthesis of Fully-modified 5'-d(TCC-GTC-ATC-GCT-CCT-CAG-GG)-3' Phosphorothioate 20-mer (SEQ ID NO:14)

The above sequence is prepared on an Expedite (Millipore) Synthesizer on a 1 micromole scale using the 2-cyanoethyl phosphoramidites and CPG support. Detritylation is performed using 3% dichloroacetic acid in methylene chloride. Phosphoramidites are activated with a 0.22 M solution of pyridinium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 38

Synthesis of Fully-modified 5'-d(TCC-CGC-CTG-TGA)-2'-O-(MOE)-(CAT-GCA-TT)-3' Phosphorothioate 20-mer (SEQ ID NO:15)

The above sequence is prepared on a Millipore Expedite Synthesizer on a 1 micromole scale using the 2-cyanoethyl phosphoramidites and CPG support. Detritylation is performed using 3% dichloroacetic acid in methylene chloride. Phosphoramidites are activated with a 0.22 M solution of pyridinium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 39

Synthesis of Fully-modified 5'-d(GCC CAA GCT GGC)-2'-O-(MOE)-(ATC CCG TCA)-3' Phosphorothioate 20-mer (SEQ ID NO:16)

The above sequence is prepared on an Expedite (Millipore) Synthesizer on a 1 micromole scale using the 2-cyanoethyl phosphoramidites and CPG support. Detritylation is performed using 3% dichloroacetic acid in methylene chloride. Phosphoramidites are activated with a 0.22 M solution of pyridinium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 40

Synthesis of Fully-modified 5'-d(GC$^{me}$C$^{me}$C$^{me}$AA-GC$^{me}$T-GGC$^{me}$)-2'-O-(MOE)-(AU$^{me}$C$^{me}$-C$^{me}$GU$^{me}$-C$^{me}$A)-3' Phosphorothioate 20-mer (SEQ ID NO:17)

The above sequence is prepared on an Expedite (Millipore) Synthesizer on a 1 micromole scale using the 2-cyanoethyl phosphoramidites and CPG support. Detritylation is performed using 3% dichloroacetic acid in methylene chloride. Phosphoramidites are activated with a 0.22 M solution of pyridinium tetrafluoroborate and 0.11 M solution of 1-methylimidazole. Beaucage reagent is used for phosphorothioate synthesis. At the end of synthesis, the support is washed with acetonitrile, cleaved, deprotected and purified in the usual manner.

EXAMPLE 41

Synthesis of 2'-O-MOE Gapmers

Stock solutions of 2'-O-MOE amidites (0.1 M) are made in anhydrous acetonitrile and loaded onto an Expedite Nucleic Acid synthesis system (Millipore) to prepare oligonucleotides. Commercially available deoxyamidites (A, T, C and G, PerSeptive Biosystem) are also made into stock solutions (0.1 M) with anhydrous acetonitrile. All syntheses are carried out in the DMT ON mode. For the coupling of the 2'-O-MOE amidites coupling time is extended to 10 minutes and this step is carried out twice. All other steps in the protocol supplied by Millipore are used except the extended coupling time (240 seconds). Activation of phosphoramidites is done with a 0.22 M solution of pyridinium tetrafluoroborate and 0.11 M solution of 1-methylimidazole. Beaucage reagent is used for phosphorothioate synthesis. The overall coupling efficiencies are expected to be greater than 95%. The oligonucleotides are cleaved from the controlled pore glass (CPG) supports and deprotected under standard conditions using concentrated aqueous NH$_4$OH (30%) at 55° C. 5'-O-DMT containing oligomers are then purified by reverse phase liquid chromatography (C-4, Waters, 7–8×300 mm, A=50 mM triethylammonium acetate pH 1, B=100%CH$_3$CN, 5 to 60% B in 60 minutes). Detritylation with aqueous 80% acetic acid (1 mL, 30 min., room temperature), evaporation, followed by desalting by using Sephadese G-25 column will yield the oligonucleotides expectedly as foams. All oligomers are analyzed by CGE, HPLC and mass spectrometry.

2'-MOE GAPMERS

| Sequence 5'-3' | Backbone | Target |
|---|---|---|
| T*sT*sC*ST*sC*s GsCsCsCsGsCsTsCs C*sT*sC*sC*sT*sC*sC* (SEQ ID NO: 18) | P=S | c-raf |
| T*sT*sC*sT*sC*s GsCsTsGsGsTsGs AsGs T*sT*sT*sC*sA* (SEQ ID NO: 19) | P=S | pkc-a |
| T*oT*oC*oT*oC*s GsCsCsCsGsCsTsCs C*oT*oC*oC*oT*oC*oC* (SEQ ID NO: 20) | P=O, P=S, P=O | c-raf |
| T*oT*oC*oT*oC*s GsCsTsGsGsTsGs AsGs T*oT*oT*oC*oA* (SEQ ID NO: 21) | P=O, P=S, | pkc-a |

* = 2'-O-MOE
C's are all 5-methyl substituted
s = phosphorothioate internucleotide linkages
o = phosphodiester internucleotide linkages

EXAMPLE 42

Synthesis of Uniformly Modified 2'-Modified Oligonucleotide

2-O-MOE amidites of A, $^{5me}$C, G and T are dissolved in anhydrous acetonitrile to give 0.1 M solution. These solutions are loaded onto an Expedite Nucleic Acid Synthesis system (Millipore) to synthesize the oligonucleotides. Activation of phosphoramidites is done with a 0.22 M solution of pyridinium tetrafluoroborate and 0.11 M solution of 1-methylimidazole. The coupling efficiencies are expected to be more than 90%. All steps in the protocol supplied by Millipore are used except the activation step. Beaucage reagent (0.1 M in acetonitrile) is used as a sulfurizing agent. For diester synthesis, t-BuOOH is used as the oxidizing agent.

The oligomers are cleaved from the controlled pore glass(CPG) supports and deprotected under standard conditions using concentrated aqueous NH40H (30%) at 55° C. 5'-O-DMT containing oligomers are then purified by reverse phase high performance liquid chromatography (C-4, Waters, 7.8×300 mm, A=50 mM triethylammonium acetate, pH–7, B=acetonitrile, 5–60% of B in 60 min., flow 1.5 mL/minute). Detritylation with aqueous 80% acetic acid and evaporation, followed by desalting in a Sephadex G-25 column will give the oligonucleotides. Oligonucleotides are analyzed by HPLC, CGE and Mass spectrometry.

| Sequence | Target |
|---|---|
| 5' T*sC*sT*s G*sA*sG*s T*sA*sG*s C*sA*sG*s A*sG*sG*s A*sG*sC*s T*sC* 3' (SEQ ID NO: 22) | ICAM, P=S |
| 5' T*C*T*G*A*G*T*A*G*C*A*G*A*G*G*A*G*C*T*C* 3' (SEQ ID NO: 23) | ICAM, P=O |

T* = 2'-O-MOE T, A* = 2'-O-MOE A, C* = 2'-O-MOE $^{5me}$C, G* = 2'-O-MOE G

EXAMPLES 43–60

Oligonucleotide Synthesis Employing Pyridinium Hexafluorophsophate

EXAMPLE 43

Synthesis of Fully-modified 5'-d(TCC-CGC-CTG-TGA-CAT-GCA-TT)-3' Phosphorothioate 20-mer (SEQ ID NO:24)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 44

Synthesis of Fully-modified 5'-d(GCC-CAA-GCT-GGC-ATC-CGT-CA)-3' Phosphorothioate 20-mer (SEQ ID NO:25)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 45

Synthesis of Fully-modified 5'-d(GCG-TTT-GCT-CTT-CTT-CTT-GCG)-3' Phosphorothioate 21-mer (SEQ ID NO:26)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 46

Synthesis of Fully-modified 5'-d(GTT-CTC-GCT-GGT-GAG-TTT-CA)-3' Phosphorothioate 20-mer (SEQ ID NO:27)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 47

Synthesis of Fully-modified 5'-d(TCC-GTC-ATC-GCT-CCT-CAG-GG)-3' Phosphorothioate 20-mer (SEQ ID NO:28)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 48

Synthesis of Fully-modified 5'-d(TCC-CGC-CTG-TGA)-2'-O-(MOE)-(CAT-GCA-TT)-3' Phosphorothioate 20-mer (SEQ ID NO:29)

The synthesis of the above sequence is performed on a Millipore Expedite Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 49

Synthesis of Fully-modified 5'-d(GCC CAA GCT GGC)-2'-O-(MOE)-(ATC CCG TCA)-3' Phosphorothioate 20-mer (SEQ ID NO:30)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 50

Synthesis of Fully-modified 5'-d(GC$^{me}$C$^{me}$-C$^{me}$AA-GC$^{me}$T-GGC$^{me}$)-2'-O-(MOE)-(AU$^{me}$C$^{me}$-C$^{me}$GU$^{me}$-C$^{me}$A)-3'-Phosphorothioate 20-mer (SEQ ID NO:31)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of pyridinium hexafluorophosphate and 0.11 M solution of 1-methylimidazole. Beaucage reagent is used for phosphorothioate synthesis. At the end of synthesis, the support is washed with acetonitrile, cleaved, deprotected and purified in the usual manner.

EXAMPLE 51

Synthesis of 2'-MOE Gapmers

A 0.1 M solution of 2'-O-MOE amidites are made in anhydrous acetonitrile and loaded onto an Expedite Nucleic Acid synthesis system (Millipore) to synthesize oligonucleotides. All other deoxyamidites (A, T, C and G, PerSeptive Biosystem) used in synthesis are also made as 0.1 M solution in anhydrous acetonitrile. All syntheses are carried out in DMT on mode. For the coupling of the 2'-O-MOE amidites coupling time is extended to 10 minutes and this step is carried out twice. All other steps in the protocol supplied by Millipore are used except the extended coupling time (240 seconds). Activation of phosphoramidites is done with a 0.22 M solution of pyridinium hexafluorophosphate and 0.11 M solution of 1-methylimidazole. Beaucage reagent is used for phosphorothioate synthesis. The overall coupling efficiencies are expected to be more than 95%. The oligonucleotides are cleaved from the controlled pore glass (CPG) supports and deprotected under standard conditions using concentrated aqueous NH$_4$OH (30%) at 55° C. 5'-O-DMT containing oligomers are then purified by reverse phase liquid chromatography (C-4, Waters, 7–8×300 mm, A=50 mM triethylammonium acetate pH 1, B=100% CH$_3$CN, 5 to 60% B in 60 minutes). Detritylation with aqueous 80% acetic acid (1 mL, 30 min., room temperature), concentration, followed by desalting by using Sephadese G-25 column will give the oligonucleotides as a pure foam. All oligomers are then analyzed by CGE, HPLC and mass spectrometry.

MOE GAPMERS

| Sequence 5'-3' | Backbone | Target |
|---|---|---|
| T*sT*sC*sT*sC*s GsCsCsCsGsCsTsCs C*sT*sC*sC*sT*sC*sC* (SEQ ID NO: 18) | P=S | c-raf |
| T*sT*sC*sT*sC*s GsCsTsGsGsTsGs AsGs T*sT*sT*sC*sA* (SEQ ID NO: 19) | P=S | pkc-? |
| T*oT*oC*oT*oC*s GsCsCsCsGsCsTsCs C*oT*oC*oC*oT*oC*oC* (SEQ ID NO: 20) | P=O, P=S, P=O | c-raf |
| T*oT*oC*oT*oC*s GsCsTsGsGsTsGs AsGs T*oT*oT*oC*oA* (SEQ ID NO: 21) | P=O, P=S, | pkc-? |

* = 2'-O-MOE; All C = 5-methyl C;

EXAMPLE 52

General Procedure for Uniformly Modified 2'-Modified Oligonucleotide Synthesis

2-O-MOE amidites of A, $^{5me}$C, G and T are dissolved in anhydrous acetonitrile to give 0.1 M solution. These solutions are loaded onto an Expedite Nucleic Acid Synthesis system (Millipore) to synthesize the oligonucleotides. Activation of phosphoramidites is done with a 0.22 M solution of pyridinium hexafluorophosphate and 0.11 M solution of 1-methylimidazole. The coupling efficiencies are expected to be more than 95%. For the coupling of the first amidite coupling time is extended to 6 minutes and this step is carried out twice. All other steps in the protocol supplied by Millipore are used except the extended coupling time. Beaucage reagent (0.1 M in acetonitrile) is used as a sulfurizing agent. For diester synthesis, t-BuOOH is used as the oxidizing agent. The oligomers are cleaved from the controlled pore glass(CPG) supports and deprotected under standard conditions using concentrated aqueous NH40H (30%) at 55° C. 5'-O-DMT containing oligomers are then purified by reverse phase high performance liquid chromatography (C-4, Waters, 7.8×300 mm, A=50 mM triethylammonium acetate, pH–7, B=acetonitrile, 5–60% of B in 60 min., flow 1.5 mL/minute). Detritylation with aqueous 80% acetic acid and evaporation, followed by desalting in a Sephadex G-25 column will give the oligonucleotides. Oligonucleotides are analyzed by HPLC, CGE and Mass spectrometry.

| Sequence | Target |
|---|---|
| 5' T*sC*sT*s G*sA*sG*s T*sA*sG*s C*sA*sG*s A*sG*sG*s A*sG*sC*s T*sC* 3' (SEQ ID NO: 22) | ICAM, P=S |
| 5' T*C*T*G*A*G*T*A*G*C*A*G*A*G*G*A*G*C*T*C* 3' (SEQ ID NO: 23) | ICAM, P=O |

T* = 2'-O-MOE T, A* = 2'-O-MOE A, C* = 2'-O-MOE $^{5me}$C, G* = 2'-O-MOE G

EXAMPLES 53–60

Oligonucleotide Synthesis Using Benzimidazolium or Imidazolium Tetrafluoroborate Activator

EXAMPLE 53

Synthesis of Fully-modified 5'-d(TCC-CGC-CTG-TGA-CAT-GCA-TT)-3' Phosphorothioate 20-mer (SEQ ID NO:32)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 54

Synthesis of Fully-modified 5'-d(GCC-CAA-GCT-GGC-ATC-CGT-CA)-3'-Phosphorothioate 20-mer (SEQ ID NO:33)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 55

Synthesis of Fully-modified 5'-d(GCG-TTT-GCT-CTT-CTT-CTT-GCG)-3' Phosphorothioate 21-mer (SEQ ID NO:34)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 56

Synthesis of Fully-modified 5'-d(GTT-CTC-GCT-GGT-GAG-TTT-CA)-3' Phosphorothioate 20-mer (SEQ ID NO:35)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 57

Synthesis of Fully-modified 5'-d(GCC CAA GCT GGC)-2'-O-(MOE)-(ATC CCG TCA)-3' Phosphorothioate 20-mer (SEQ ID NO:36)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 56

Synthesis of Fully-modified 5'-d(TCC-CGC-CTG-TGA)-2'-O-(MOE)-(CAT-GCA-TT)-3' Phosphorothioate 20-mer (SEQ ID NO:37)

The synthesis of the above sequence is performed on a Millipore Expedite Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 57

Synthesis of Fully-modified 5'-d(TCC-CGC-CTG-TGA)-2'-O-(MOE)-(CAT-GCA-TT)-3' Phosphorothioate 20-mer (SEQ ID NO:37)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Sulfurization is performed using Beaucage reagent. At the end of synthesis, the support is washed with acetonitrile, cleaved, deprotected and purified in the usual manner

EXAMPLE 58

Synthesis of Fully-modified 5'-d(GC$^{me}$C$^{me}$-C$^{me}$AA-GC$^{me}$T-GGC$^{me}$)-2'-O-(MOE)-(AU$^{me}$C$^{me}$-C$^{me}$GU$^{me}$-C$^{me}$A)-3' Phosphorothioate 20-mer (SEQ ID NO:38)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium tetrafluoroborate and 0.11 M solution of 1-methylimidazole. Beaucage reagent is used for phosphorothioate synthesis. At the end of synthesis, the support is washed with acetonitrile, cleaved, deprotected and purified in the usual manner.

EXAMPLE 59

Synthesis of 2'-MOE Gapmers

A 0.1 M solution of 2'-O-MOE amidites are prepared in anhydrous acetonitrile and loaded onto an Expedite Nucleic Acid synthesis system (Millipore) to synthesize oligonucleotides. All other deoxyamidites (A, T, C and G, PerSeptive Biosystem) used in synthesis also made as 0.1 M solution in anhydrous acetonitrile. All syntheses are carried out in DMT on mode. For the coupling of the 2'-O-MOE amidites coupling time is extended to 10 minutes and this step is carried out twice. All other steps in the protocol supplied by Millipore are used except the extended coupling time (240 seconds). Activation of phosphoramidites is done with a 0.22 M solution of imidazolium or benzimidazolium tetrafluoroborate and 0.11 M solution of 1-methylimidazole. Beaucage reagent is used for phosphorothioate synthesis. The overall coupling efficiencies are expected to be more than 95%. The oligonucleotides are cleaved from the controlled pore glass (CPG) supports and deprotected under standard conditions using concentrated aqueous NH$_4$OH (30%) at 55° C. 5'-O-DMT containing oligomers are then purified by reverse phase liquid chromatography (C-4, Waters, 7–8×300 mm, A=50 mM triethylammonium acetate pH 1, B=100% CH$_3$CN, 5 to 60% B in 60 minutes). Detritylation with aqueous 80% acetic acid (1 mL, 30 min., room temperature), concentration, followed by desalting by using Sephadese G-25 column will give the oligonucleotides as pure foams. All oligomers are then analyzed by CGE, HPLC and mass spectrometry.
MOE GAPMERS

| Sequence 5'-3' | Backbone | Target |
|---|---|---|
| T*sT*sC*sT*sC*s GsCsCsCsGsCsTsCs C*sT*sC*sC*sT*sC*sC* (SEQ ID NO: 18) | P=S | c-raf |
| T*sT*sC*sT*sC*s GsCsTsGsGsTsGs AsGs T*sT*sT*sC*sA* (SEQ ID NO: 19) | P=S | Pkc-a |
| T*oT*oC*oT*oC*s GsCsCsCsGsCsTsCs | P=O, P=S, | c-raf |
| C*oT*oC*oC*oT*oC*oC* (SEQ ID NO: 20) | P=O | |
| T*oT*oC*oT*oC*s GsCsTsGsGsTsGs AsGs T*oT*oT*oC*oA* (SEQ ID NO: 21) | P=O, P=S, | Pkc-a |

* = 2'-O-MOE; All C = 5-methyl C;

EXAMPLE 60

Synthesis of Uniformly Modified 2'-Modified Oligonucleotide

2-O-MOE amidites of A, $^{5me}$C, G and T are dissolved in anhydrous acetonitrile to give 0.1 M solution. These solutions are loaded onto an Expedite Nucleic Acid Synthesis system (Millipore) to synthesize the oligonucleotides. Activation of phosphoramidites is done with a 0.22 M solution of imidazolium or benzimidazolium tetrafluoroborate and 0.11 M solution of 1-methylimidazole. The coupling efficiencies are expected to be more than 90%. For the coupling of the first amidite coupling time is extended to 10 minutes and this step is carried out twice. All other steps in the protocol supplied by Millipore are used except the extended coupling time. Beaucage reagent (0.1 M in acetonitrile) is used as a sulfurizing agent. For diester synthesis, t-BuOOH is used as the oxidizing agent. The oligomers are cleaved from the controlled pore glass(CPG) supports and deprotected under standard conditions using concentrated aqueous NH4OH (30%) at 55° C. 5'-O-DMT containing oligomers are then purified by reverse phase high performance liquid chromatography (C-4, Waters, 7.8×300 mm, A=50 mM triethylammonium acetate, pH–7, B=acetonitrile, 5–60% of B in 60 min., flow 1.5 mL/minute). Detritylation with aqueous 80% acetic acid and evaporation, followed by desalting in a Sephadex G-25 column will give the oligonucleotides. Oligonucleotides are analyzed by HPLC, CGE and Mass spectrometry.

| Sequence | Target |
|---|---|
| 5' T*sC*sT*s G*sA*sG*s T*sA*sG*s C*sA*sG*s A*sG*sG*s A*sG*sC*s T*sC* 3' (SEQ ID NO: 22) | ICAM, P=S |
| 5' T*C*T*G*A*G*T*A*G*C*A*G*A*G*G*A*G*C*T*C* 3' (SEQ ID NO: 23) | ICAM, P=O |

T* = 2'-O-MOE T, A* 2'-O-MOE A, C* = 2'-O-MOE $^{5me}$C, G* = 2'-O-MOE G

EXAMPLES 61–70

Oligonucleotide Synthesis with Imidazolium or Benzimidazolium Hexafluorophosphate as Activator

EXAMPLE 61

Synthesis of Fully-modifled 5'-d(TCC-CGC-CTG-TGA-CAT-GCA-TT)-3' Phosphorothioate 20-mer (SEQ ID NO:39)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 62

Synthesis of Fully-modified 5'-d(GCC-CAA-GCT-GGC-ATC-CGT-CA)-3' Phosphorothioate 20-mer (SEQ ID NO:40)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 63

Synthesis of Fully-modified 5'-d(GCG-TTT-GCT-CTT-CTT-CTT-GCG)-3' Phosphorothioate 21-mer (SEQ ID NO:41)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 64

Synthesis of Fully-modified 5'-d(GTT-CTC-GCT-GGT-GAG-TTT-CA)-3' Phosphorothioate 20-mer (SEQ ID NO:42)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 65

Synthesis of Fully-modified 5'-d(TCC-GTC-ATC-GCT-CCT-CAG-GG)-3' Phosphorothioate 20-mer (SEQ ID NO:43)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 66

Synthesis of Fully-modified 5'-d(TCC-CGC-CTG-TGA)-2'-O-(MOE)-(CAT-GCA-TT)-3' Phosphorothioate 20-mer (SEQ ID NO:44)

The synthesis of the above sequence is performed on a Millipore Expedite Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner.

EXAMPLE 67

Synthesis of Fully-modified 5'-d(GCC CAA GCT GGC)-2'-O-(MOE)-(ATC CCG TCA)-3' Phosphorothioate 20-mer (SEQ ID NO:45)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Sulfurization is performed using Beaucage reagent. At the end of synthesis, the support is washed with acetonitrile, cleaved, deprotected and purified in the usual manner

EXAMPLE 68

Synthesis of Fully-modified 5'-d(GC$^{me}$C$^{me}$C$^{me}$AA-GC$^{me}$T-GGC$^{me}$)-2'-O-(MOE)-(AU$^{me}$C$^{me}$C$^{me}$GU$^{me}$-C$^{me}$A)-3' Phosphorothioate 20-mer (SEQ ID NO:46)

The synthesis of the above sequence is performed on an Expedite (Millipore) Synthesizer on a 1 micromole scale using the 2-cyanoethyl phosphoramidites and CPG support. Detritylation is performed using 3% dichloroacetic acid in methylene chloride. Activation of phosphoramidites is done with a 0.22 M solution of imidazolium or benzimidazolium hexafluorophosphate and 0.11 M solution of 1-methylimidazole. Beaucage reagent is used for phosphorothioate synthesis. At the end of synthesis, the support is washed with acetonitrile, cleaved, deprotected and purified in the usual manner.

EXAMPLE 69

Synthesis of 2'-MOE Gapmers

A 0.1 M solution of 2'-O-MOE amidites are prepared in anhydrous acetonitrile and loaded onto an Expedite Nucleic Acid synthesis system (Millipore) to synthesize oligonucleotides. All other deoxyamidites (A, T, C and G, PerSeptive Biosystem) used in synthesis are also made as 0.1 M solution in anhydrous acetonitrile. All syntheses are carried out in DMT on mode. For the coupling of the 2'-O-MOE amidites coupling time is extended to 10 minutes and this step is carried out twice. All other steps in the protocol supplied by Millipore are used except the extended coupling time (240 seconds). Activation of phosphoramidites is done with a 0.22 M solution of imidazolium or benzimidazolium hexafluorophosphate and 0.11 M solution of 1-methylimidazole. Beaucage reagent is used for phosphorothioate synthesis. The overall coupling efficiencies are expected to be more than 95%. The oligonucleotides are cleaved from the controlled pore glass (CPG) supports and deprotected under standard conditions using concentrated aqueous NH$_4$OH (30%) at 55° C. 5'-O-DMT containing oligomers are then purified by reverse phase liquid chromatography (C-4, Waters, 7–8×300 mm, A=50 mM triethylammonium acetate pH 1, B=100%CH$_3$CN, 5 to 60% B in 60 minutes). Detritylation with aqueous 80% acetic acid (1 mL, 30 min., room temperature), concentration, followed by desalting by using Sephadese G-25 column will give the oligonucleotides as pure foams. All oligomers are then analyzed by CGE, HPLC and mass spectrometry.

MOE GAPMERS

| Sequence 5'-3' | Backbone | Target |
|---|---|---|
| T*sT*sC*sT*sC*s GsCsCsCsGsCsTsCs C*sT*sC*sC*sT*sC*sC* (SEQ ID NO: 18) | P=S | c-raf |
| T*sT*sC*sT*sC*s GsCsTsGsGsTsGs AsGs T*sT*sT*sC*sA* (SEQ ID NO:19) | P=S | pkc-a |
| T*oT*oC*oT*oC*s GsCsCsCsGsCsTsCs C*oT*oC*oC*oT*oC*oC* (SEQ ID NO: 20) | P=O, P=S, P=O | c-raf |
| T*oT*oC*oT*oC*s GsCsTsGsGsTsGs AsGs T*oT*oT*oC*oA* (SEQ ID NO: 21) | P=O, P=S, | pkc-a |

* = 2'-O-MOE; All C = 5-methyl C;

EXAMPLE 70

General Procedure for Uniformly Modified 2'-Modified Oligonucleotide Synthesis 2-O-MOE amidites of A, $^{5me}$C, G and T are dissolved in anhydrous acetonitrile to give 0.1 M solution. These solutions are loaded onto an Expedite Nucleic Acid Synthesis system (Millipore) to synthesize the oligonucleotides. Activation of phosphoramidites is done with a 0.22 M solution of imidazolium or benzimidazolium hexafluorophosphate and 0.11 M solution of 1-methylimidazole. The coupling efficiencies are expected to be more than 90%. For the coupling of the first amidite coupling time is extended to 10 minutes and this step is carried out twice. All other steps in the protocol supplied by Millipore are used except the extended coupling time. Beaucage reagent (0.1 M in acetonitrile) is used as a sulfurizing agent. For diester synthesis, t-BuOOH is used as the oxidizing agent. The oligomers are cleaved from the controlled pore glass(CPG) supports and deprotected under standard conditions using concentrated aqueous NH40H (30%) at 55° C. 5'-O-DMT containing oligomers are then purified by reverse phase high performance liquid chromatography (C-4, Waters, 7.8×300 mm, A=50 mM triethylammonium acetate, pH–7, B=acetonitrile, 5–60% of B in 60 min., flow 1.5 mL/minute). Detritylation with aqueous 80% acetic acid and evaporation, followed by desalting in a Sephadex G-25 column will give the oligonucleotides. Oligonucleotides are analyzed by HPLC, CGE and Mass spectrometry.

| Sequence | Target |
|---|---|
| 5' T*sC*sT*s G*sA*sG*s T*sA*sG*s C*sA*sG*s A*sG*sG*s A*sG*sC*s T*sC* 3' (SEQ ID NO: 22) | ICAM, P=S |
| 5' T*C*T*G*A*G*T*A*G*C*A*G*A*G*G*A*G*C*T*C* 3' (SEQ ID NO: 23) | ICAM, P=O |

T* = 2'-O-MOE T, A* = 2'-O-MOE A, C* = 2'-O-MOE $^{5me}$C, G* = 2'-O-MOE G

EXAMPLE 71

Oligonucleotide Synthesis without Amino Group Protection

Fully-modified 5'-d(TCC-CGC-CTG-TGA-CAT-GCA-TT)-3' phosphorothioate 20 mer (SEQ ID NO:24); fully modified 5'-d(GCC-CAA-GCT-GGC-ATC-CGT-CA)-3' phosphorothioate 20 mer (SEQ ID NO:11); fully-modified 5'-d(GCG-TTT-GCT-GCT-CTT-CTT-CTT-GCG)-3' phosphorothioate 21 mer (SEQ ID NO:47); fully-modified 5'-d (GTT-CTC-GCT-GGT-GAG-TTT-CA)-3' phosphorothioate 20 mer (SEQ ID NO:27); fully-modified 5'-d(TCC-GTC-ATC-GCT-CCT-CAG-GG)-3' phosphorothioate 20 mer (SEQ ID NO:28); fully-modified 5'-d(TCC-CGC-CTG-TGA)2'-O-(MOE)-(CAT-GCA-TT)-3' phosphorothioate 20 mer (SEQ ID NO:29); fully-modified 5'-d(GCC CAA GCT GGC)-2'-O-(MOE)-(ATC CCG TCA)-3' Phosphorothioate 20-mer (SEQ ID NO:30); fully-modified 5'-d(GC$^{me}$C$^{me}$-C$^{me}$AA-GC$^{me}$T-GGC$^{me}$)-2'-O-(MOE)-(AU$^{me}$C$^{me}$-C$^{me}$-GU$^{me}$-C$^{me}$A)-3' phosphorothioate 20 mer (SEQ ID NO:17); and gapmers are synthesized.

2'-MOE GAPMERS

| Sequence 5'-3' | Backbone | Target |
|---|---|---|
| T*sT*sC*sT*sC*s GsCsCsCsGsCsTsCs C*sT*sC*sC*sT*sC*sC* (SEQ ID NO: 18) | P=S | c-raf |
| T*sT*sC*sT*sC*s GsCsTsGsGsTsGs AsGs T*sT*sT*sC*sA* (SEQ ID NO: 19) | P=S | pkc-a |
| T*oT*oC*oT*oC *5 GsCsCsCsGsCsTsCs C*oT*oC*oC*oT*oC*oC * (SEQ ID NO: 20) | P=O, P=S, P=O | c-raf |
| T*oT*oC*oT*oC*s GsCsTsGsGsTsGs AsGs T*oT*oT*oC*OA* (SEQ ID NO: 21) | P=O, P=S, | pkc-a |

* = 2'-O-MOE; All C = 5-methyl C;

Uniformly 2'-modified oligomers

| Sequence | Target |
|---|---|
| 5' T*sC*sT*s G*sA*sG*s T*sA*sG*s C*sA*sG*s A*sG*sG*s A*sG*sC*s T*sC* 3' (SEQ ID NO: 22) | ICAM, P=S |
| 5' T*C*T*G*A*G*T*A*G*C*A*G*A*G*G*A*G*C*T*C* 3' (SEQ ID NO: 23) | ICAM, P=O |

T* = 2'-O-MOE T, A* = 2'-O-MOE A, C* = 2'-O-MOE $^{5me}$C, G* = 2'-O-MOE G

Nucleobase unprotected 2'-O-MOE amidites of A, $^{5me}$C, G and T and nucleobase unprotected 2'-deoxy amidites of A, C, G and T are dissolved in anhydrous acetonitrile to give 0.1 M solutions. These solutions are loaded onto an Expedite Nucleic Acid Synthesis system (Millipore) to synthesize the oligonucleotides. Activation of phosphoramidites is done with a 0.22 M solution of one of the following activators: pyridinium tetrafluoroborate, pyridinium hexafluoroborate, imidazolium tetrafluoroborate, benzimidazolium tetrafluoroborate, imidazolium hexafluorophosphate or benzimidazolium hexafluorophosphate. After the coupling, any nucleobase N-phosphitylated side product is reverted back by treatment with excess of benzimidazolium triflate in methanol at 25° C. for 2 minutes before proceeding to oxidation. The coupling efficiencies are expected to be more than 90%. For the coupling of the first amidite coupling time is extended to 10 minutes and this step is carried out twice. All other steps in the protocol supplied by Millipore are used except the extended coupling time. Beaucage reagent (0.1 M in acetonitrile) is used as a sulfurizing agent. For diester synthesis, t-BuOOH is used as the oxidizing agent.

EXAMPLES 72–80

Oligonucleotides with Bioreversible Protecting Groups Present in Phosphate: Building Blocks and Oligonucleotide Synthesis

EXAMPLE 72

General Procedures

All reagents and solvents are purchased from Aldrich Chemical CO. Flash chromatography is performed on silica gel (Baker 40 um). Thin layer chromatography is performed on Kieselgel 60 F-254 glass plates from E. Merck and compounds are visualized with UV light and sulfuric acid-methanol spray followed by charring. Solvent systems used for thin-layer chromatography and flash chromatography are: A; ethyl acetate-hexanesl:1. B; ethyl acetate-hexanes-TEA 2:3:0.5. $^1$H and $^{31}$p spectra are recorded using a Gemini 200 Varian spectrometer. All reactions are performed under an argon atmosphere and solutions rotary evaporated at 35–45° C. in vacuo using a vacuum pump-vacuum controller combination.

EXAMPLE 73

2'-O-MOE-5'-O-(4,4'-Dimethoxytrityl)-5-methyluridine(S-pivaloyl-2-thioethyl) bis[N,N-Diisopropylphosphoramidite]

To a stirred and precooled solution of 2'-O-MOE-5'-O-(4,4'-dimethoxytrityl)-5-methyluridine (10 g, 16 mmol) and diisopropylethylamine (2.7 g, 21 mmol) in dry dichloromethane (200 mL) in an ice bath is added dropwise a solution of N,N-(diisopropylamino)chlorophosphine (5.2 g, 19 mmol) in dry dichloromethane. The resulting mixture is stirred at room temperature for 55 minutes. Imidazolium triflate (8.0 mmol) is added and a solution of S-(2-hydroxyethyl)thiopivaloate (Tosquellas, G. et al. *Nucleic Acid Res.* 26, 2069, 1998) (3.4 g, 21 mmol) in dry dichloromethane is added dropwise over a period of 15 minutes. The reaction mixture is further stirred for 20 hours at room temperature. At the end of this time, the mixture is diluted with dry $CH_2Cl_2$ (100 mL) and washed with $NaHCO_3$ (80 mL) and brine 3 times (100 mL) each, dried over $MgSO_4$ and evaporated to a foam. Flash chromatography using 1:1 Hexanes:EtOAc containing 0.5% triethylamine will yield the title compound.

EXAMPLE 74

2'-O-MOE-5'-O-(4,4'-Dimethoxytrityl)-5-methyluridine(S-acetyl-2-thioethyl) bis[N,N-Diisopropylphosphoramidite] 2'-O-MOE-5'-O-DMT-5-Methyluridine A solution of 2'-O-MOE-5'-O-DMT-5-methyluridine (10 g, 16 mmol) and diisopropylethylamine (2.7 g, 21 mmol) in dry dichloromethane (200 mL) is cooled in an ice bath and stirred for 15 min. Added dropwise a solution of N,N-(diisopropylamino)chlorophosphine (5.2 g, 19 mmol) in dry $CH_2Cl_2$. The resulting mixture is stirred at room temperature for 45 minutes. Added imidazolium triflate (8.0 mmol) and a solution of S-(2-hydroxyethyl)-thioacetate (Tosquellas et al. *Nucleic Acids Res.* 26, 2069, 1998) freshly prepared (2.6 g, 21 mmol) in dry $CH_2Cl_2$ in a periods of 10 minutes. The reaction mixture is further stirred for 18 hr at RT. At the end of. this time, the mixture is diluted with dry $CH_2Cl_2$ (100 mL) and washed with NaHCO3 (60 mL) and brine 3 times (80 mL) each and dried over $MgSO_4$ and evaporated to a solid light yellow foam. Purified by flash chromatography using 1:1 Hexanes:EtOAc containing 0.5% triethylamine will yield the desired product.

EXAMPLE 75

2'-Deoxy-5'-O-dimethoxytrityl-adenosine-(S-pivaloyl-2-thioethyl) bis[N,N-Diisopropylphosphoramidite]

To a cooled solution of 2'-deoxy-5'-O-dimethyltrityl-adenosine (7.3 mmol) and diisopropylamine (1.22 g, 9.5 mmol) in dry dichloromethane (100 ml) stirred in an ice bath, is added a solution of N,N-(diisopropylamino) chlorophosphine (2.33 g, 8.76 mmol) dropwise in dry $CH_2Cl_2$. The resulting mixture is stirred at RT for 45 min. A solution of S-(2-hydroxyethyl) thiopivaloate (1.42 g, 8.76 mmol) and imidazolium triflate (3.65 mmol) in dry $CH_2Cl_2$ is added in a periods of 10 min. The reaction mixture is stirred for 22hr at RT. The mixture is diluted with $CH_2Cl_2$ (50 mL) and washed with NaHCO3 (15 mL) and brine (25 mL) dried over $MgSO_4$, filtered and evaporated the solvent to a light yellow foam. Purification is done by flash chromatography using Hexanes:EtOAc 1:3 containing 0.5% triethylamine, will yield the desired product.

EXAMPLE 76

2'-Deoxy-5'-O-dimethyltrityl-cytidine-(S-pivaloyl-2-thioethyl) bis[N,N-Diisopropylphosphoramidite]

The title compound is prepared as per the procedure described in example 75.

EXAMPLE 77

2'-Deoxy-5'-O-dimethyltrityl-cytidine-(S-benzoyl-2-thioethyl) bis[N,N-Diisopropylphosphoramidite]

The title compound is prepared as per the procedure described in example 75.

EXAMPLE 78

2'-Deoxy-5'-O-dimethyltrityl-guanosine-(s-pivaloyl-2-thioethyl) bis[N,N-Diisopropylphosphoramidite]

The title compound is prepared as per the procedure described in example 75.

EXAMPLE 79

2'-Deoxy-5'-O-dimethoxytrityl-adenosine-(S-acetyl-2-thioethyl) bis [N,N-Diisopropylphosphoramidite]

The title compound is prepared as per the procedure described in example 75.

EXAMPLE 80

2'-Deoxy-5'-O-dimethoxytrityl-cytidine-(S-acetyl-2-thioethyl) bis[N,N-Diisopropylphosphoramidite]

The title compound is prepared as per the procedure described in example 75.

EXAMPLES 81–86

Oligonucleotides Synthesis With the Aid of (S-Pivaloyl 2-mercaptoethyl) 3'-O-[(5'-O-(4,4'-Dimethoxytrityl)thymidyl] N,N-Diisopropylphosphoramidite

EXAMPLE 81

(S-Pivaloyl 2-Mercaptoethyl) 3'-O-[(5'-O-(4,4'-Dimethoxy-trityl)thymidyl] N,N-Diisopropylphosphoramidite Bis(N,N-diisopropylamino)phosphorochloridite (267mg, 1 mmol) in $CH_2Cl_2$ (2.5 mL) is added to a stirred solution of S-pivaloyl 2-mercaptoethanol (162 mg, 1 mmol) and ethyldiisopropylamine (142 mg, 1.1 mmol) in $CH_2Cl_2$ (1 mL for 5 min) at −30° C. The mixture is allowed to warm to room temperature and is stirred for 30 minutes to give S-Pivaloyl-2-mercaptoethyl-N,N,N',N'-tetraisopropyl phosphorodiamidite. The volume of solution is adjusted to 4.0 mL, an aliquot (320 mL) is taken and added to dry 5'-O-(4,4'-dimethoxytrityl)-thymidine (21.7 mg, 40 mmol). Anhydrous imidazolium triflate (0.45 M in MeCN; 71 mL, 32 mmol) is added, and the mixture is stirred for 40 minutes at room temperature. The reaction is quenched with aqueous $NaHCO_3$ (5%; 2 mL), diluted with saturated NaCl (5 mL) and extracted with benzene (3×10 mL). The extracts are dried over $Na_2SO_4$ and evaporated in vacuo. The residue is dissolved in 50% aqueous MeCN and purified by reversed phase HPLC on a DeltaPak 15 mm C18 300 column (7.8×300 mm). Isocratic elution with 50% aqueous MeCN for 10 minutes and with 75% aqueous MeCN for 25 minutes at a flow rate 5 mL $min^{-1}$ is applied. Fractions containing pure are collected, diluted with water (50 mL) and extracted with benzene (5×10 mL). Extracts are dried over $Na_2SO_4$ and evaporated in vacuo to give S-pivaloyl 2-mercaptoethyl 3'-O-[(5'-O-(4,4'-dimethoxytrityl)thymidyl] N,N-diisopropylphosphoramidite.

EXAMPLE 82

Oligonucleotide Synthesis 2-(pivaloylthio)ethyl-undecathymidylates are assembled on an ABI 380B DNA Synthesizer using 2-cyanoethyl 3-(4,4'-di-methoxytrityloxy)-3-(2-nitrophenyl)ethyl phosphate, phosphor-amidite chemistry, benzimidazolium triflate or imidazolium triflate as the activator, and 3H-1,2-benzodithiol-3-one 1,1-dioxide Beaucage reagent (0.1 M in MeCN) as a sulfur-transfer reagent. 5'-O-(4,4'-dimethoxytrityl)thymidyl 2-(pivaloyl-thio)ethyl N,N-diisopropylaminophosphite is employed as a building block. After the synthesis, the oligonucleotide is cleaved from the support photolytically (Guzaev et al. *Biiorg. Med. Chem. Lett.* 8, 1123, 1998).

Deprotection and Isolation of Oligonucleotides

The 5'-DMTr protected oligonucleotide is isolated by HPLC (DeltaPak 15μ C18 300 Å, 3.9×300 mm; 0.1 M $NH_4OAc$ as buffer A, 0.05 M $NH_4OAc$ in 75% aqueous MeCN as buffer B; a linear gradient from 15 to 80% B in 30 minutes at a flow rate 5.0 mL min⁻). The collected fractions are evaporated, treated with 80% aqueous AcOH for 20 minutes, and evaporated to dryness. The residue is desalted on the same column eluting first with 0.1 M NaOAc (10 minutes), then with water (10 minutes) and finally eluting as a sodium salt with 50% aqueous MeCN (20 minutes) at a flow rate 5.0 mL min⁻.

EXAMPLE 83

Dodeca[(2-pivaloylthio)ethyl 2'-O-(MOE)-5-Methyluridyl Phosphate]

The title compound is prepared on an ABI 380B synthesizer by using 0.1 M (2-pivaloylthio)ethyl 5'-O-(4,4'-dimethoxytrityl)-2'-O-(MOE)-5-methyluridyl N,N-disopropylaminophosphite in MeCN, photolabile solid support from the previous example, 0.45 M imidazolium triflate as an activator, 0.5 M t-BuOOH in MeCN as an oxidizer, and 6 minutes coupling time. Upon completeness of the chain assembly (DMTr-Off synthesis) the solid support is dried on an oil pump, placed in a Pyrex test tube and suspended in 80% aqueous MeCN (3 mL). The suspension is degassed, placed in photochemical reactor, and irradiated for 30 minutes at room temperature. The tube is centrifuged, and supernatant is collected. A fresh portion of 80% aqueous MeCN is added.

This procedure is repeated for 5 times until less than 4 OD of oligonucleotide material is released after irradiation for 30 minutes. The collected supernatants are diluted with water to get a solution in 30% aqueous MeCN, applied on an HPLC column (DeltaPak 15μ C18 300 A, 3.9×300 mm), and chromatographed in a linear gradient from 25 to 80% MeCN in water for 40 minutes. The main peak is collected and evaporated in vacuo to afford the title compound. An aliquot (5 OD) of the obtained material is treated with concentrated aqueous ammonia (2 mL) for 8 hours at room temperature, evaporated to dryness, and re-dissolved in water (200 μL). Analysis by capillary electrophoresis (CE) will reveal comigration with authentic sample of dodeca[2'-O-(MOE)-5-methyluridyl phosphate].

EXAMPLE 84

Dodeca[(2-Pivaloylthio)ethyl 2'-O-(MOE)-5-Methyluridyl Thiophosphate]

The title compound is prepared as described above except that 3H-1,2-benzodithiol-3-one 1,1-dioxide (0.05 M in MeCN) is used on an oxidation step as a sulfur transfer reagent. Chromatography on the same column in a linear gradient from 70 to 100% MeCN in water will afford the title compound. After treatment with concentrated aqueous ammonia as above, analysis by capillary electrophoresis (CE) will reveal comigration with authentic sample of dodeca[2'-O-(MOE)-5-methyluridyl thiophosphate].

EXAMPLE 85

3'-O-Diglycolyl-5'-(4,4'-dimethoxytrityl)thymidine Derivatized CPG

The solid support is prepared according to references Pon, R. T. and Yu, S., *Nucleic Acid Res.* 1997, 25, 3629–3635, and Mullah, B. and Andrus, A., *Tetrahedron Lett.*, 1997, 38, 5751–5754. 5'-(4,4'-Dimethoxytrityl)thymidine (1090 mg, 2.0 mmol), diglycolic anhydride (689 mg, 6.0 mmol), pyridine (10 mL) is stirred for 7 hours at room temperature. The mixture is quenched with water (2 mL) for 10 minutes and evaporated to an oil. The residue is dissolved in ethyl acetate (50 mL), washed with triethylammonium acetate (2 M aqueous, 5×15 10 mL), then with water (5×10 mL), dried over $Na_2SO_4$ and evaporated. The residue is dissolved in pyridine (10 mL), long chain alkyl amine Controlled Pore Glass (CPG, 3.0g) is added and the mixture is degassed in vacuo. N,N'-diisopropylcarbodiimide (800 mg, 6.3 mmol) is added, and the mixture is shaken overnight at room temperature. The solid support is filtered out, treated with a mixture of acetic anhydride, N-methylimidazole, 2,6-lutidine and THF (1:1:2:16 v/v) for 30 minutes, filtered, washed on filter with acetonitrile (5×10 mL) and dried on an oil pump. Efficiency of the derivatization is determined by dimethoxytrityl assay to show the loading which is expected to be about 60 µmol g$^{-4}$.

EXAMPLE 86

Oligonucleotide Synthesis

Chimerical oligothymidylates are assembled on an ABI 380B DNA Synthesizer using 5'-O-(4,4'-dimethoxytrityl) thymidine 3'-O-(carboxymethyloxy)acetate derivatized CPG (diglycolyl-T CPG)$^I$ (Scheme 1), phosphoramidite chemistry, and either commercial oxidizer for 3H-1,2-benzodithiol-3-one 1,1-dioxide (0.05 M in MeCN) as the sulfur-transfer reagent. Either 5'-O-(4,4'-dimethoxytrityl) thymidyl 2-(picaloylthio)ethyl N,N'-diisopropylaminophosphite or 3'-O-[5-methyl-2-O-(MOE)-5'-O-(4,4'-dimethoxytrityl)uridyl] 2-(pivaloylthio)ethyl N,N'-diisopropylaminophosphite are employed for chain assembly to create 2-(pivaloylthio)ethyl triester internucleosidic moieties. After extensive washing with MeCN and drying the oligonucleotide is released from the solid support by treatment with 0.01 M K$_2$CO$_3$ in MeOH (2×5 mL and 2×20 mL for 1 and 15 µmol syntheses, respectively). Each portion is passed back and forth through the column for 45 minutes, neutralized by passing through short column with Dowex 50W×8 (PyH$^+$; ca. 1 mL). The combined eluates are evaporated to dryness, co-evaporated with MeCN (10 mL), and dissolved in water. The obtained mixture consists of along with products of methanolysis of 2-(pivaloylthio)ethyl groups (ca. 1 to 1.5% of methanolysis per each group). Target oligonucleotide is isolated by RP HPLC on Delta Pak 15 µm C18 300 Å column (3.9×300 mm and 7.8×300 mm for 1 and 15 µmol syntheses, respectively), using 0.1 M NH$_4$OAc as buffer A, 80% aq MeCN as buffer B, and a linear gradient from 0 to 100% B in 50 minutes at a flow rate 1.5 and 5 mL min$^-$, respectively. Collected fractions are evaporated, redissolved in water and desalted by injecting onto the same column, then washing with water (10 minutes) and eluting an oligonucleotide as an ammonium salt with 50% aq MeCN (20 minutes). Homogeneity of oligonucleotides is characterized by RP HPLC, mass spectrometry and $^{31}$p NMR.

EXAMPLE 87

Synthesis of Bioreversible (SATE) Oligonucleotides without Exocyclic Amine Protection Using the Activators Synthetic oligonucleotides as shown in Example 71, with (S-pivaloyl 2-mercaptoethyl)bioreversible phosphate protecting groups for the internucleotide phosphate linkages, are synthesized with the aid Of (S-pivaloyl 2-mercaptoethyl) 3'-O-[(5'-O-(4,4'-dimethoxytrityl)thymidyl] N,N-diisopropyl-phosphoramidite, (S-pivaloyl 2-mercaptoethyl) 3'-O-[(5'-O-(4,4'-dimethoxytrityl)adenyl] N,N-Diisopropylphosphoramidite, (S-pivaloyl 2-mercaptoethyl) 3'-O-[(5'-O-(4,4'-dimethoxytrityl)cytidyl] N,N-diisopropylphosphoramidite, and (S-pivaloyl 2-mercaptoethyl) 3'-O-[(5'-O-(4,4'-dimethoxytrityl)guanyl] N,N-diisopropylphosphoramidite without exocyclic amine protection. Oligonucleotides are assembled on an ABI 380B DNA Synthesizer using 5'-O-(4,4'-dimethoxytrityl) nucleoside 3'-O-(carboxymethyloxy)acetate derivatized CPG (diglycolyl-Nucleoside-CPG), phosphoramidite chemistry, 3H-1,2-benzodithiol-3-one 1,1-dioxide (0.05 M in MeCN) as the sulfur-transfer reagent, t-BuOOH as the oxidizing agent for phosphodiester linkages. One of the following activators as a 0.22 M solution along with a 0.11 M solution of N-methyl-imidazole in acetonitrile is used as the activator: pyridinium tetrafluoroborate, pyridinium hexafluorophosphate, imidazoliumtetrafluoroborate, imidazolim hexafluorophosphate, benzimidazolium tetrafluoroborate, or benzimidazolium hexafluorophosphate, imidazolium triflate, or benzimidazolium triflate. The small amount of nucleobase N-phosphitylated side product is reverted back to the free nucleoside derivative by treating the reaction solid support with excess of benzimidazolium triflate in methanol at ambient temperature for 2–3 minutes. After completeness of oligonucleotide synthesis, the column is washed with dioxane (10 mL) to give pivaloyl-containing oligonucleosides still on the solid support. After extensive washing with MeCN and drying, the oligonucleotide is released from the solid support by treatment with 0.01 M K$_2$CO$_3$ in MeOH (2×5 mL and 2×20 mL for 1 and 15 umol syntheses, respectively). Each portion is passed back and forth through the column for 45 minutes, neutralized by passing through short column with Dowex 5OW×8 (PyH$^+$; ca. 1 mL). The combined eluates are evaporated to dryness, co-evaporated with MeCN (10 mL), and dissolved in water. The obtained mixture includes the products of methanolysis of 2-(pivaloylthio)ethyl groups (ca. 1 to 1.5% of methanolysis per each group). Target oligonucleotide is isolated by RP HPLC on Delta Pak 15 µm C18 300 Å column (3.9×300 mm and 7.8×300 mm for 1 and 15 µmol syntheses, respectively), using 0.1 M NH$_4$OAc as buffer A, 80% aq MeCN as buffer B, and a linear gradient from 0 to 100% B in 50 minutes at a flow rate 1.5 and 5 mL min$^-$, respectively. Collected fractions are evaporated, redissolved in water and desalted by injection onto the same column, then washing with water (10 minutes) and finally elution as thes ammonium salt with 50% aq MeCN (20 minutes). Homogeneity of chimerical oligonucleotides is characterized by RP HPLC and capillary electrophoresis, and their structure is confirmed by mass spectrometry and $^{31}$p NMR.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the preparation of an oligonucleotide comprising the steps of:
   providing a 3'-nucleoside phosphoramidite or 3'-oligonucleotide phosphoramidite; and
   reacting said 3'-nucleoside phosphoramidite or 3'-oligonucleotide phosphoramidite with the 5'-hydroxyl of a nucleoside, or oligonucleotide in the presence of an activating reagent;
   said nucleoside or oligonucleotide being optionally bound to a solid support;
   said activating reagent comprising at least one pyridinium salt and one substituted imidazole.

2. The method of claim 1 wherein the pyridinium salt has the formula

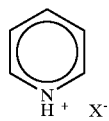

where $X^-$ is trifluoroacetate, $^-$O-mesyl, $^-$O-tosyl, $^-$Br, $^-$O-trifluorosulfonyl, hexafluorophosphate or tetrafluoroborate.

3. The method of claim 2 wherein the substituted imidazole is 1-methylimidazole.

4. The method of claim 3 wherein $X^-$ is trifluoroacetate.

5. The method of claim 3 wherein the 3'-mononucleoside phosphoramidite or 3'-oligonucleotide phosphoramidite is reacted with the 5'-hydroxyl of a solid-support bound nucleoside, nucleotide or oligonucleotide.

6. The method of claim 3 wherein the oligonucleotide comprises phosphorothioate intersugar linkages.

7. The method of claim 1 wherein B is devoid of exocyclic amine protection.

8. A synthetic method comprising:
   providing a phosphoramidite of formula:

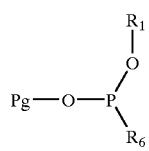

wherein:
$R_1$ is a nucleoside or an oligonucleotide;
$R_6$ is $-N(R_7)_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen;
Pg is a phosphorus protecting group;
and reacting said phosphoramidite with a hydroxyl group of a nucleoside linked to a solid support, or an oligonucleotide linked to a solid support, to form a compound of formula:

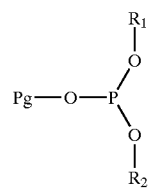

wherein:
$R_2$ is a nucleoside linked to a solid support, or an oligonucleotide linked to a solid support;
said reaction being performed in the presence of an activating reagent, said activating reagent comprising at least one pyridinium salt and one substituted imidazole; and
oxidizing or sulfurizing said compound to form a compound of formula:

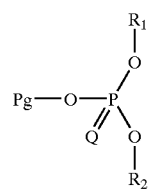

wherein Q is O or S.

9. The method of claim 8 wherein the pyridinium salt has the formula

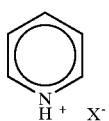

where X⁻ is trifluoroacetate, ⁻O-mesyl, ⁻O-tosyl, ⁻Br, ⁻O-trifluorosulfonyl, hexafluorophosphate or tetrafluoroborate.

10. The method of claim 9 wherein the substituted imidazole is 1-methylimidazole.

11. The method of claim 10 wherein X– is trifluoroacetate.

12. The method of claim 8 wherein B is devoid of exocyclic amine protection.

13. A synthetic method comprising:
providing a compound of Formula X:

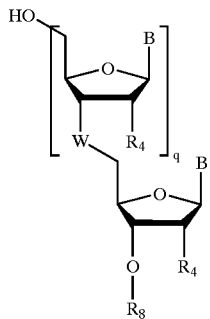

wherein:
B is a nucleobase;
$R_8$ is H, a hydroxyl protecting group, or a linker connected to a solid support;
W is an optionally protected internucleoside linkage;
q is 0 to about 50;
$R_4$ is H, F, O—R, S—R or N—R($R_{10}$);
R is H, a protecting group, or has one of the formulas:

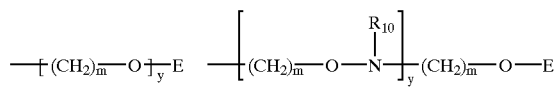

where
each m is independently from 1 to 10;
y is from 0 to 10;
E is H, a hydroxyl protecting group, $C_1$-$C_{10}$ alkyl, N($R_{10}$)($R_{11}$) or N=C($R_{10}$)($R_{11}$); substituted or unsubstituted $C_1$-$C_{10}$ alkyl, $C_2$-$C_{10}$ alkenyl, $C_2$-$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$-$C_{10}$ alkyl, $C_2$-$C_{10}$ alkenyl, $C_2$-$C_{10}$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$ are joined in a ring structure that can include at least one heteroatom selected from N and O;
or R is —$CH_2$—$CH_2$—O—$CH_2$—$CH_2$—N($R_{10}$)($R_{11}$);

reacting the compound of Formula X in the presence of an activating reagent with a compound of Formula XI:

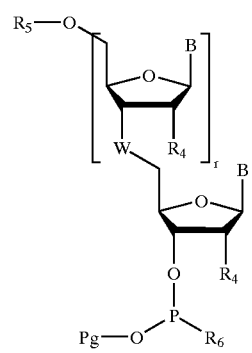

where r is 0 to about 50;
$R_5$ is a hydroxyl protecting group;
$R_6$ is —N($R_7$)$_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen;
to form a compound of Formula XII:

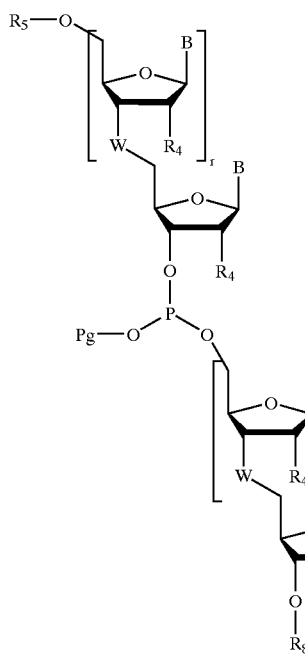

wherein said activating reagent comprises at least one pyridinium salt and one substituted imidazole.

14. The method of claim 13 wherein the pyridinium salt has the formula:

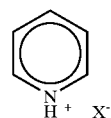

where X⁻ is trifluoroacetate, ⁻O-mesyl, ⁻O-tosyl, ⁻Br, or ⁻O-trifluorosulfonyl, hexafluorophosphate or tetrafluoroborate.

15. The method of claim 14 wherein the substituted imidazole is 1-methylimidazole.

16. The method of claim 15 wherein X⁻ is trifluoroacetate.

17. The method of claim 13 wherein $R_8$ is a linker connected to a solid support.

18. The method of claim 13 wherein $R_4$ is —O—R wherein R has the formula —[—$(CH_2)_m$—O—]$_y$—E; m is 2, y is 1; and E is $CH_3$, —$N(R_{10})(R_{11})$, or —$CH_2$—$CH_2$—$N(R_{10})(R_{11})$.

19. The method of claim 13 wherein r is 0.

20. The method of claim 13 wherein $R_6$ is diisopropylamino.

21. The method of claim 13 wherein Pg is —$CH_2CH_2CN$, —$CH_2CH$=$CHCH_2CN$, para-$CH_2C_6H_4CH_2CN$, —$(CH_2)_{2-5}N(H)COCF_3$, —$CH_2CH_2Si(C_6H_5)_2CH_3$, or —$CH_2CH_2N(CH_3)COCF_3$.

22. The method of claim 13 wherein Pg is —$CH_2CH_2CN$.

23. The method of claim 13 further comprising oxidizing or sulfurizing the compound of Formula XII to form a compound of Formula XIII:

XIII where Q is O or S.

24. The method of claim 23 further comprising a capping step.

25. The method of claim 24 wherein the capping step is performed prior to oxidation.

26. The method of claim 25 further comprising the step of cleaving the oligomeric compound to produce a further compound of formula X.

27. The method of claim 13 wherein B is devoid of exocyclic amine protection.

28. A synthetic method comprising:
providing a compound of Formula X:

X wherein:
B is a nucleobase;
$R_8$ is H, a hydroxyl protecting group, or a linker connected to a solid support;
W is an optionally protected internucleoside linkage;
q is 0 to about 50;
$R_4$ is H, F, O—R, S—R or N—$R(R_{10})$;
R is H, a protecting group, or has one of the formulas:

$$-\!\!+\!\!(CH_2)_{\overline{m}}\!-\!\!O\!-\!\!\!+_{\overline{y}}\!\!E \quad -\!\!+\!\!(CH_2)_{\overline{m}}\!-\!\!O\!-\!\!N\!\!\!\begin{array}{c}R_{10}\\|\\\phantom{N}\end{array}\!\!\!+_{\overline{y}}\!(CH_2)_{\overline{m}}\!-\!\!O\!-\!\!E$$

where
each m is independently from 1 to 10;
y is from 0 to 10;
E is H, a hydroxyl protecting group, $C_1$–$C_{10}$ alkyl, $N(R_{10})(R_{11})$ or N=$C(R_{10})(R_{11})$; substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; alkylthioalkyl, a nitrogen protecting group, or R and $R_{10}$, together, are a nitrogen protecting group or wherein R and $R_2$ are joined in a ring structure that can include at least one heteroatom selected from N and O;
or R is —$CH_2$—$CH_2$—O—$CH_2$—$CH_2$—$N(R_{10})(R_{11})$; provided that $R_{14}$ is not H or OH;
reacting the compound of Formula X in the presence of an activator with a compound of Formula XI:

XI where r is 0 to about 50;

R$_6$ is a hydroxyl protecting group;

R$_6$ is —N(R$_7$)$_2$ wherein R$_7$ is alkyl having from one to about six carbons; or R$_7$ is a heterocycloalkyl or heterocycloalkenyl ring containing from 4 to 7 atoms, and having up to 3 heteroatoms selected from nitrogen, sulfur, and oxygen;

to form a compound of Formula XII:

XII

[Chemical structure showing R$_5$—O-sugar-B with W, R$_4$ substituents, repeated r times, linked via Pg—O—P—O to another sugar-B unit with W, R$_4$, repeated q times, ending in sugar with O—R$_8$]

wherein the activator has the formula G$^+$U$^-$, where

G$^+$ is selected from the group consisting of pyridinium, imidazolium, and benzimidazolium; and U$^-$ is selected from the group consisting of hexafluorophosphate, tetrafluoroborate, triflate, hydrochloride, trifluoroacetate, dichloroacetate, $^-$O-mesyl, $^-$O-tosyl, $^-$Br, and $^-$O-trifluorosulfonyl.

29. The method of claim 28 wherein R$_8$ is a linker connected to a solid support.

30. The method of claim 29 wherein R$_4$ is —O—R wherein R has the formula —[—(CH$_2$)$_m$—O—]$_y$—E; m is 2, y is 1; and E is CH$_3$, —N(R$_{10}$)(R$_{11}$), or —CH$_2$—CH$_2$—N(R$_{10}$)(R$_{11}$).

31. The method of claim 28 wherein r is 0.

32. The method of claim 28 wherein R$_6$ is diisopropylamino.

33. The method of claim 28 wherein Pg is —CH$_2$CH$_2$CN, —CH$_2$CH=CHCH$_2$CN, para-CH$_2$C$_6$H$_4$CH$_2$CN, —(CH$_2$)$_{2-5}$N(H)COCF$_3$, —CH$_2$CH$_2$Si(C$_6$H$_5$)$_2$CH$_3$, or —CH$_2$CH$_2$N(CH$_3$)COCF$_3$.

34. The method of claim 28 wherein Pg is —CH$_2$CH$_2$CN.

35. The method of claim 28 further comprising oxidizing or sulfurizing the compound of Formula XII to form a compound of Formula XIII:

XIII

[Chemical structure showing R$_5$—O-sugar-B with W, R$_4$ substituents, repeated r times, linked via Pg—O—P(=Q)—O to another sugar-B unit with W, R$_4$, repeated q times, ending in sugar with O—R$_8$]

where Q is O or S.

36. The method of claim 35 further comprising a capping step.

37. The method of claim 36 wherein the capping step is performed prior to oxidation.

38. The method of claim 37 further comprising the step of cleaving the oligomeric compound to produce a further compound of Formula X.

39. The method of claim 28 wherein G$^+$ is pyridinium and U$^-$ is hexafluorophosphate or tetrafluoroborate.

40. The method of claim 39 wherein U$^-$ is hexafluorophosphate.

41. The method of claim 28 wherein G$^-$ is imidazolium or benzimidazolium and U$^-$ is selected from the group consisting of hexafluorophosphate, tetrafluoroborate, triflate, hydrochloride, trifluoroacetate, dichloroacetate, $^-$O-mesyl, $^-$O-tosyl, $^-$Br, and $^-$O-trifluorosulfonyl.

42. The method of claim 41 wherein G$^+$ is imidazolium or benzimidazolium and U$^-$ is selected from the group consisting of hexafluorophosphate, tetrafluoroborate, and triflate.

43. The method of claim 41 wherein G$^+$ is imidazolium or benzimidazolium and U$^-$ is selected from the group consisting of hydrochloride, trifluoroacetate, dichloroacetate, $^-$O-mesyl, $^-$O-tosyl, $^-$Br, and $^-$O-trifluorosulfonyl.

44. The method of claim 28 wherein G$^+$ is imidazolium and U$^-$ is selected from the group consisting of hexafluorophosphate, tetrafluoroborate, triflate, hydrochloride, trifluoroacetate, dichloroacetate, $^-$O-mesyl, $^-$O-tosyl, $^-$Br, and $^-$O-trifluorosulfonyl.

45. The method of claim 44 wherein U$^-$ is selected from the group consisting of hexafluorophosphate, tetrafluoroborate, and triflate.

46. The method of claim 44 wherein U$^-$ is selected from the group consisting of hydrochloride, trifluoroacetate, dichloroacetate, $^-$O-mesyl, $^-$O-tosyl, $^-$Br, and $^-$O-trifluorosulfonyl.

47. The method of claim 28 wherein G$^+$ is benzimidazolium and U$^-$ is selected from the group consisting of hexafluorophosphate, tetrafluoroborate, triflate, hydrochloride, trifluoroacetate, dichloroacetate, ⁻O-mesyl, ⁻O-tosyl, ⁻Br, and ⁻O-trifluorosulfonyl.

48. The method of claim 47 wherein U⁻ is selected from the group consisting of hexafluorophosphate, tetrafluoroborate, and triflate.

49. The method of claim 47 wherein U⁻ is selected from the group consisting of hydrochloride, trifluoroacetate, dichloroacetate, ⁻O-mesyl, ⁻O-tosyl, ⁻Br, and ⁻O-trifluorosulfonyl.

50. The method of claim 28 wherein the activator is imidazolium triflate.

51. The method of claim 28 wherein B is devoid of exocyclic amine protection.

52. The method of claim 50 wherein B is devoid of exocyclic amine protection.

53. A synthetic method comprising:
providing a compound of Formula XX:

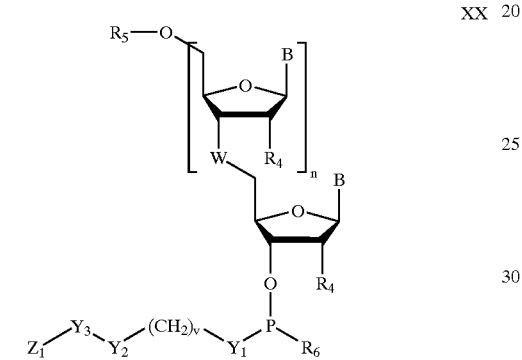

XX wherein:
$R_4$ is H, F, O—R, S—R or N—R($R_{10}$);
R is H, a protecting group, or has one of the formulas:

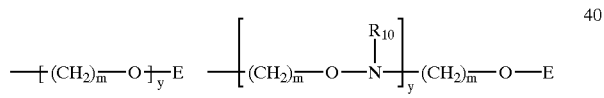

where
each m is independently from 1 to 10;
y is from 0 to 10;
E is H, a hydroxyl protecting group, $C_1$–$C_{10}$ alkyl, $N(R_{10})(R_{11})$ or $N=C(R_{10})(R_{11})$; substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; and
each $R_{10}$ or $R_{11}$ is, independently, H, substituted or unsubstituted $C_1$–$C_{10}$ alkyl, $C_2$–$C_{10}$ alkenyl, $C_2$–$C_{10}$ alkynyl, wherein the substitutions are selected from one or several halogen, cyano, carboxy, hydroxy, nitro and mercapto residues; alkylthioalkyl, a nitrogen protecting group, or $R_{10}$ and $R_{11}$, together, are a nitrogen protecting group or wherein $R_{10}$ and $R_{11}$ are joined in a ring structure that can include at least one heteroatom selected from N and O;
or R is —$CH_2$—$CH_2$—O—$CH_2$—$CH_2$—N($R_{10}$)($R_{11}$);

$R_5$ is a hydroxyl protecting group;
$Z_1$ is aryl having 6 to about 14 carbon atoms or alkyl having from one to about six carbon atoms;
$Y_1$ is O or S;
$Y_2$ is O or S;
$Y_3$ is C(=O) or S;
v is 2 to about 4;
B is a nucleobase;
$R_6$ is —N($R_7$)$_2$ wherein $R_7$ is alkyl having from one to about six carbons; or $R_7$ is a heterocycloalkyl or heterocycloalkenyl ring containing from 4 to 7 atoms, and having up to 3 heteroatoms selected from nitrogen, sulfur, and oxygen;
reacting said compound of Formula XX with a compound of Formula XXI:

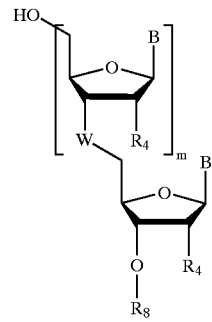

XXI wherein:
$R_8$ is H, a hydroxyl protecting group, or a linker connected to a solid support;
in the presence of an activator to form a compound of Formula XXII:

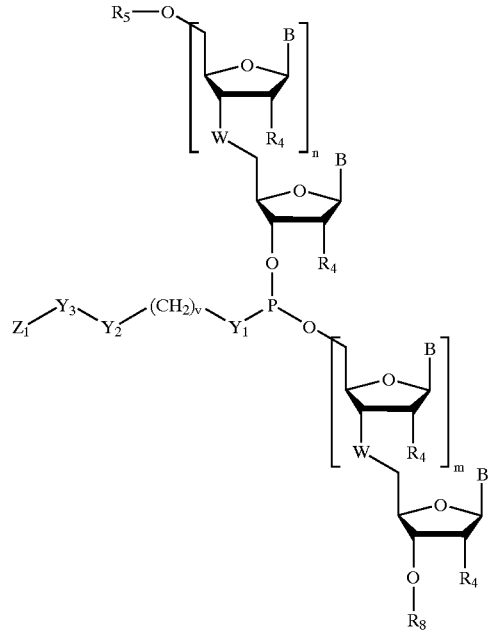

XXII wherein said activator has the formula G⁺U⁻, where:
G⁺ is selected from the group consisting of pyridinium, imidazolium, and benzimidazolium; and
U⁻ is selected from the group consisting of hexafluorophosphate, tetrafluoroborate, triflate, hydrochloride, trifluoroacetate, dichloroacetate, ⁻O-mesyl, ⁻O-tosyl, ⁻Br, and ⁻O-trifluorosulfonyl; or said activator is a substituted imidazolium triflate.

54. The method of claim 53 wherein said activator is imidazolium triflate.

55. The method of claim 54 wherein v is 2; and $Y_3$ is C (=O).

56. The method of claim 55 wherein Z is methyl, phenyl or t-butyl.

57. The method of claim 56 wherein Z is t-butyl.

58. The method of claim 55 wherein n is 0.

59. The method of claim 55 wherein $R_2$ is a linker to a solid support.

60. The method of claim 55 wherein $Y_1$ and $Y_2$ are each O.

61. The method of claim 55 wherein $Y_1$ and $Y_2$ are each S.

62. The method of claim 55 wherein $Y_1$ is O and $Y_2$ is S.

63. The method of claim 55 wherein each $R_6$ is isopropyl.

64. The method of claim 55 wherein n is 0; $R_3$ is H, $R_5$ is diisopropylamino; $Y_1$ is O; $Y_2$ is S; and Z is methyl or t-butyl.

65. The method of claim 64 wherein Z is t-butyl.

66. The method of claim 54 wherein each B is devoid of exocyclic amine protection.

67. The method of claim 54 wherein W is an optionally protected phosphodiester, phosphorothioate, phosphorodithioate, or alkyl phosphonate internucleotide linkage.

68. The method of claim 54 further comprising oxidizing or sulfurizing the compounds of Formula XXII to form a compound of Formula XXIII:

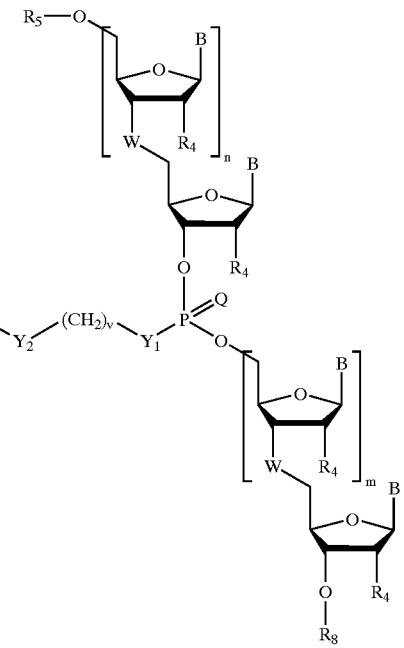

XXIII where Q is O or S.

69. The method of claim 68 further comprising a capping step.

70. The method of claim 69 wherein the capping step is performed prior to oxidation.

71. The method of claim 70 further comprising the step of cleaving the oligomeric compound to produce a further compound of Formula XXI.

* * * * *

UNITED STATES PATENT AND TRADEMARK OFFICE
CERTIFICATE OF CORRECTION

PATENT NO. : 6,642,373 B2
DATED : November 4, 2003
INVENTOR(S) : Manoharan et al.

It is certified that error appears in the above-identified patent and that said Letters Patent is hereby corrected as shown below:

Title page,
Item [75], Inventors, please delete "Muthia" and insert therefor -- Muthiah --;

Column 89,
Line 15, please delete "X-" and insert therefor -- $X^-$ --;

Column 93,
Line 2, please delete "$R_6$" and insert therefor -- $R_5$ --;

Column 94,
Line 40, please delete "$G^-$" and insert therefor -- $G^+$ --.

Signed and Sealed this

First Day of November, 2005

JON W. DUDAS
*Director of the United States Patent and Trademark Office*